US006103492A

United States Patent [19]
Yu

[11] Patent Number: 6,103,492
[45] Date of Patent: Aug. 15, 2000

[54] POLYNUCLEOTIDE ENCODING MU OPIOID RECEPTOR

[75] Inventor: Lei Yu, Indianapolis, Ind.

[73] Assignee: Indiana University, Indianapolis, Ind.

[21] Appl. No.: 08/889,108

[22] Filed: Jul. 7, 1997

Related U.S. Application Data

[63] Continuation of application No. 08/305,518, Sep. 13, 1994, abandoned, which is a continuation-in-part of application No. 08/120,601, Sep. 13, 1993, which is a continuation-in-part of application No. 08/056,886, Mar. 8, 1993, abandoned.

[51] Int. Cl.$^7$ ............................ C12P 21/06; C12P 21/04; C12N 1/20; C12N 15/74
[52] U.S. Cl. ...................... 435/69.1; 435/70.1; 435/71.1; 435/71.2; 435/325; 435/471; 435/252.3; 435/320.1; 536/23.5
[58] Field of Search .............................. 536/23.5, 24.31; 435/69.1, 252.3, 254.11, 325, 320

[56] References Cited

U.S. PATENT DOCUMENTS 5,658,783  8/1997  Grandy et al. .......................... 435/325

FOREIGN PATENT DOCUMENTS 0 612 845  8/1994  European Pat. Off. .

OTHER PUBLICATIONS

Wang, FEBS Letters, 338, 217–222, 1994.
Fukuda, FEBS Letters, 343, 42–46, 1994.
Ueda, PNAS, 85, 7013–7017, 1988.
Lin, Science, 254, 1022–1024, 1991.
Dohlman, H.G., "Model Systems for the Study of Seven–Transmembrane–Segment Receptors," *Annu. Rev. Biochem.*, 60:653–688, 1991.
Dohlman et al., "A Family of Receptors Coupled to Guanine Nucleotide Regulatory Proteins," *Biochemistry*, 26:2657–2664, 1987.
Evans et al., "Cloning of a Delta Opioid Receptor by Functional Expression," *Science*, 258:1952–1954, 1992.
Frielle, T. et al., "Structural Basis of β–adrenergic Receptor Subtype Specificity Studied with Chimeric β1/β2–adrenergic Receptors," *Proc. Natl. Acad. Sci. USA*, 85:9494–9498, 1988.
Gioannini, T.L. et al., "Evidence for the Presence of Disulfide Bridges in Opioid Receptors Essential for Ligand Binding. Possible Role in Receptor Activation," *J. Mol. Recogn.*, 2:44–48, 1989.
Kieffer et al., "The δ–opioid receptor: Isolation of a cDNA by Expression Cloning and Pharmacological Characterization," *Proc. Natl. Acad. Sci. USA*, 89:12048–12052, 1992.
Loh et al., "Molecular Characterization of Opioid Receptors," *Annu. Rev. Pharmacol. Toxicol.*, 30:123–147, 1990.
Lutz et al., "Opioid Receptors and Their Pharmacological Profiles," *J. Receptor Res.*, 12:267–286, 1992.
Mansour et al., "Anatomy of CNS Opioid Receptors," *Trends in Neurosci.*, 7:2445–2453, 1987.

Nock et al., "Autoradiography of [3H]U–69593 Binding Sites in Rat Brain: Evidence for K Opioid Receptor Subtypes," *Eur. J. Pharmacol.*, 154:27–34, 1988.
Simon, E.J., "Opioid Receptors and Endogenous Opioid Peptides," *Medicinal Res. Rev.*, 11:357–374, 1991.
Unterwald et al., "Neuroanatomical Localization of K1 and K2 Opioid Receptors in Rat and Guinea Pig Brain," *Brain Res.*, 562:57–65, 1991.
Xie et al., "Expression Cloning of cDNA Encoding a Seven–helix Receptor from Human Placenta with Affinity for Opioid Ligands," *Proc. Natl. Acad. Sci. USA*, 89:4124–4128, 1992.
Yamada et al., "Cloning and Functional Characterization of a Family of Human and Mouse Somatostatin Receptors Expressed in Brain, Gastrointestinal Tract, and Kidney," *Proc. Natl. Acad. Sci. USA*, 89:251–255, 1992.
Yasuda et al., "Cloning of a Novel Somatostatin Receptor, SSTR3, Coupled to Adenylcyclase," *J. Biol. Chem.*, 267:20422–20428, 1992.
Schofield et al., "Molecular Characterization of a New Immunoglobulin Superfamily Protein with Potential Roles in Opioid Binding and Cell Contact," *The EMBO Journal*, 8:489–495, 1989.
Probst et al., "Sequence Alignment of the G–Protein Coupled Receptor Superfamily," *DNA and Cell Biology*, 11:1–20, 1992.
Dialog Search Report, pp. 1–14, printed May 24, 1994.
Chen et al., "Molecular Cloning and Functional Expression of a μ–Opioid Receptor from Rat Brain," *Mol. Pharm.*, 44(1):8–12, 1993.
Fukuda et al., *FEBS*, 327:311, 1993.
Li et al., *PNAS*, 88:7739, 1991.
Maneckjee et al., "Characterization of a polyclonal antibody to the μ opioid receptor," *Journal of Neuroimmunology*, 17:199–208, 1988.
Mierendorf et al., "Gene Isolation by Screening Agtll Libraries with Antibodies," *Methods in Enzymology*, 152:458–469, 1987.
Sambrook et al., "Molecular Cloning," vol. 3, Chp. 16, 1987, Academic Press.
Lane et al., "Regulation of an opioid–binding protein in NG108–15 cells parallels regulation of δ–opioid receptors," *Proc. Natl. Acad. Sci. USA*, 89:11234–11238, 1992.

(List continued on next page.)

*Primary Examiner*—Gary L. Kunz
*Assistant Examiner*—Robert Landsman
*Attorney, Agent, or Firm*—Fulbright & Jaworski

[57] ABSTRACT

The invention relates generally to compositions of and methods for obtaining mu opioid receptor polypeptides. The invention relates as well to polynucleotides encoding mu opioid receptor polypeptides, the recombinant vectors carrying those sequences, the recombinant host cells including either the sequences or vectors, recombinant opioid receptor polypeptides, and antibodies immunoreactive with mu opioid receptors. The invention includes as well, methods for using the isolated, recombinant receptor polypeptide in assays designed to select and improve substances capable of interacting with mu opioid receptor polypeptides for use in diagnostic, drug design and therapeutic applications.

37 Claims, 27 Drawing Sheets

OTHER PUBLICATIONS

Lippman et al., "Opioid–binding cell adhesion molecule (OBCAM)–related clones from a rat brain cDNA library," *Gene*, 117:249–254, 1992.

Chen et al., "Molecular cloning of a rat κ opioid receptor reveals sequence similarities to the μ and δ opioid receptors," *Biochem. J.*, 295:625–628, 1993.

Li et al., "Purification of Opioid Receptor in the Presence of Sodium Ions," *Life Sciences*, 51(15):1177–1185, 1992.

Fujioka et al., "Purification and reconstitution of μ–opioid receptors in liposome," *J. Chromat.*, 597:429–433, 1992.

Chen et al., "Molecular cloning, tissue distribution and chromosomal localization of a novel member of the opioid receptor gene family," *FEBS Lett.*, 347:279–283, 1994.

Chen and Yu, "Differential Regulation by cAMP–dependent Protein Kinase and Protein Kinase C of the μ Opioid Receptor Coupling to a G Protein–activated $K^+$ Channel," *J. Biol. Chem.*, 269(11):7839–7842, 1994.

Soong et al., "Structure and Functional Expression of a Member of the Low Voltage–Activated Calcium Channel Family," *Science*, 260:1133–1136, 1993.

Carlson et al., "Thrombin and phorbol esters cause the selective phosphorylation of a G protein other than $G_i$ in human platelets," *J. Biol. Chem.*, 264:13298–13305, 1989.-

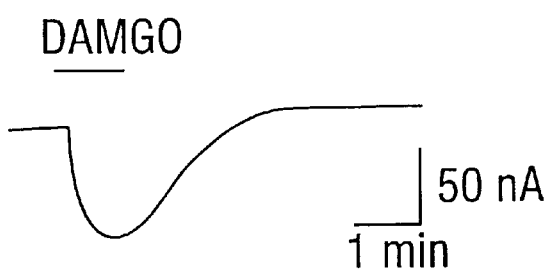
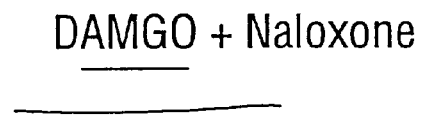
FIG. 6A
FIG. 6B
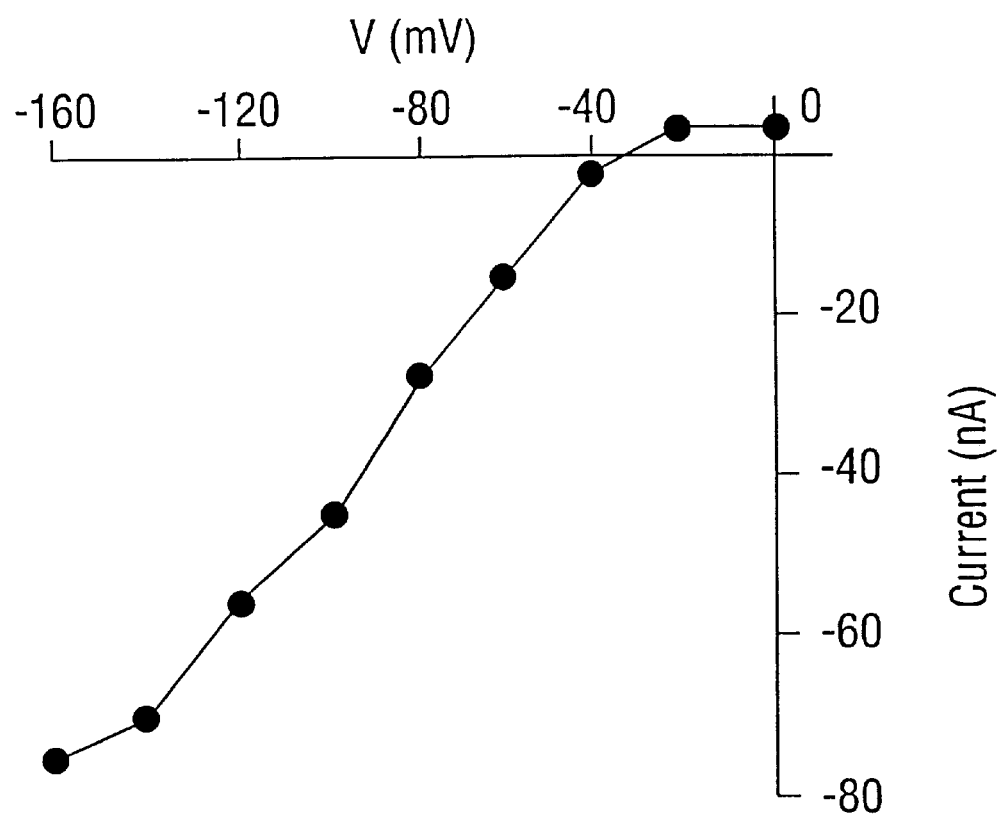
FIG. 6C

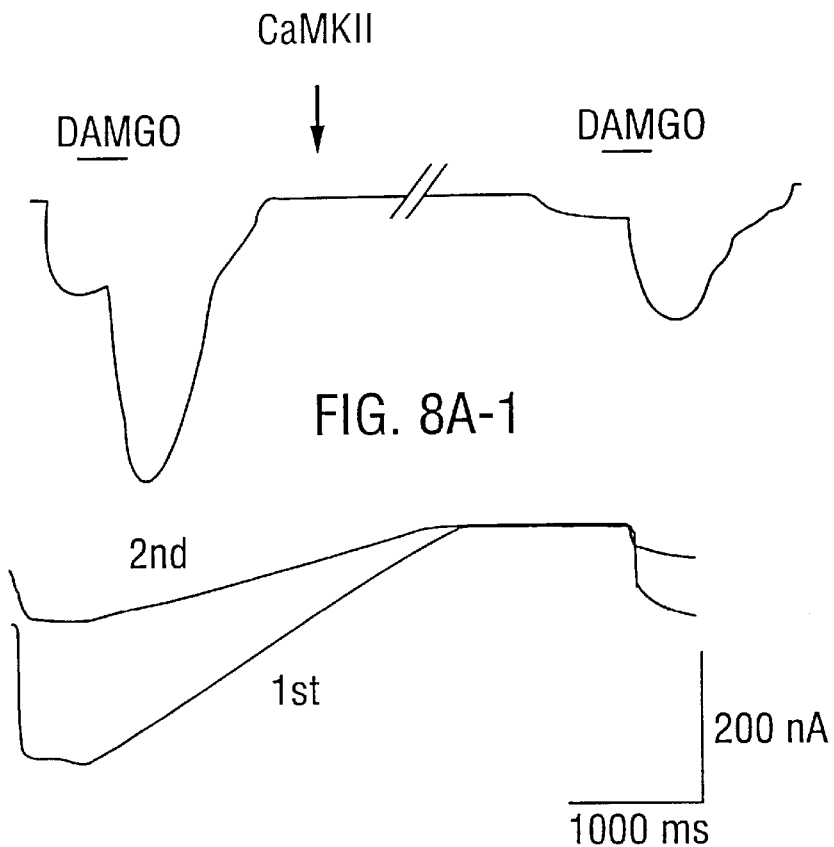
FIG. 8A-1
FIG. 8A-2
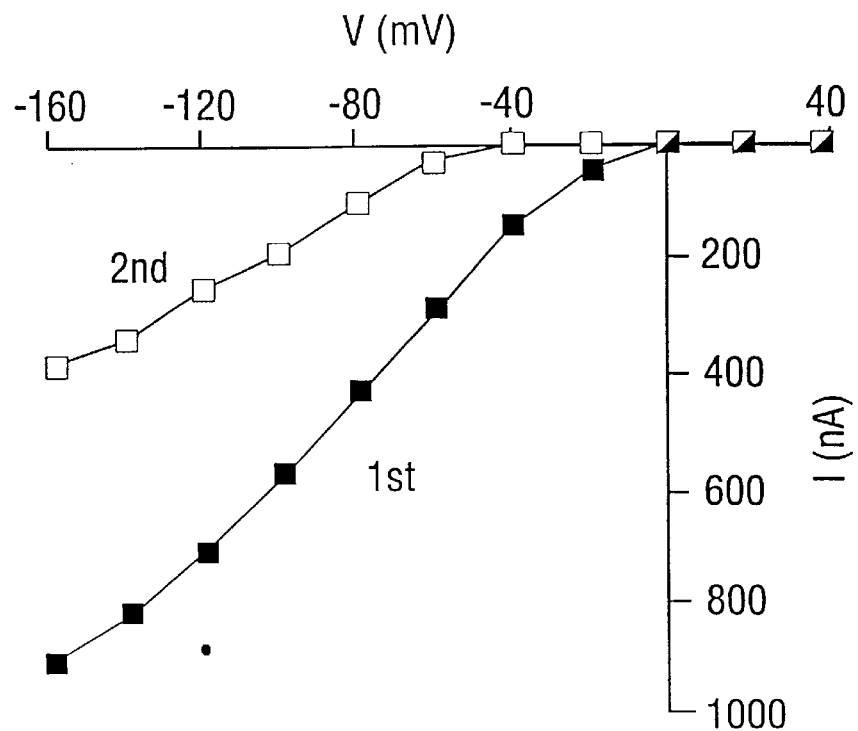
FIG. 8A-3

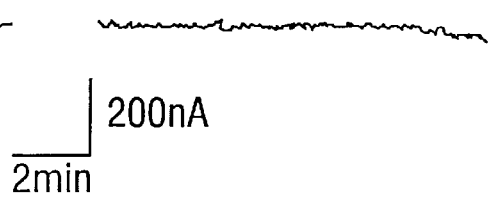
FIG. 18A-1          FIG. 18A-2
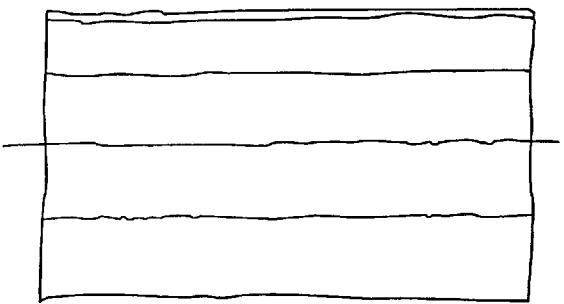
FIG. 18B-1
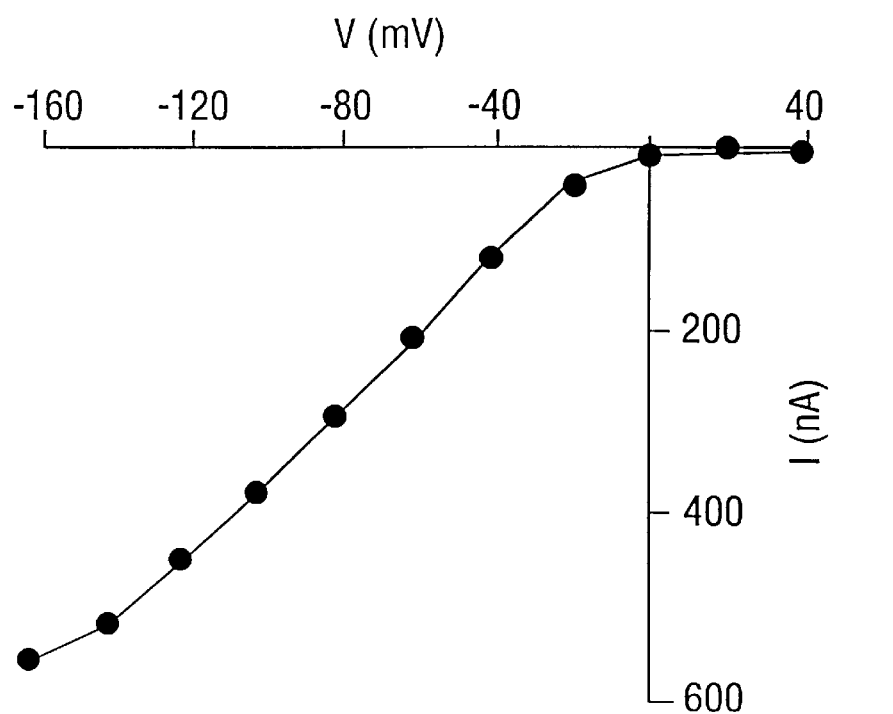
FIG. 18B-2

POLYNUCLEOTIDE ENCODING MU OPIOID RECEPTOR

The present application is a continuation of 305,518 Sep 13, 1994 abandoned which is continuation-in-part of co-pending application U.S. Ser. No. 08/120,601, filed Sep. 13, 1993. U.S. Ser. No. 08/120,601, is a continuation-in-part of U.S. Ser. No. 08/056,886, filed Mar, 8, 1993, now abandoned.

The government may own certain rights in the present invention pursuant to National Institutes of Health grants (R29NS28190 and K04NS01557).

FIELD OF THE INVENTION

This invention relates generally to compositions of and methods for obtaining mu opioid receptors. The invention relates as well to the DNA sequences encoding mu opioid receptors, the recombinant vectors carrying those sequences, the recombinant host cells including either the sequences or vectors, recombinant mu opioid receptor polypeptides and antibodies immunoreactive with mu opioid receptors. The invention includes as well methods for using the isolated, recombinant receptor polypeptides in assays designed to select among candidate substances such as agonists and antagonists of mu opioid receptors and polypeptides for use in diagnostic, drug design and therapeutic applications.

BACKGROUND OF THE INVENTION

Opioid drugs have various effects on perception of pain, consciousness, motor control, mood, and autonomic function and can also induce physical dependence (Koob et al., 1992). The endogenous opioid system plays an important role in modulating endocrine, cardiovascular, respiratory, gastrointestinal and immune functions (Olson et al., 1989). Opioids exert their actions by binding to specific membrane-associated receptors located throughout the central and peripheral nervous system (Pert et al., 1973). The endogenous ligands of these opioid receptors have been identified as a family of more than 20 opioid peptides that derive from the three precursor proteins proopiomelanocortin, proenkephalin, and prodynorphin (Hughes et al., 1975; Akil, et al., 1984). Although the opioid peptides belong to a class of molecules distinct from the opioid alkaloids, they share common structural features including a positive charge juxtaposed with an aromatic ring that is required for interaction with the receptor (Bradbury et al., 1976).

Pharmacological studies have suggested that there are numerous classes of opioid receptors, including those designated $\delta$, $\kappa$, and $\mu$ (Simon, 1991; Lutz et al., 1992). The classes differ in their affinity for various opioid ligands and in their cellular distribution. The different classes of opioid receptors are believed to serve different physiological functions (Olson et al., 1989; Simon, 1991; Lutz and Pfister, 1992). However, there is substantial overlap of function as well as of distribution. Biochemical characterization of opioid receptors from many groups reports a molecular mass of $\approx$60,000 Da for all three subtypes, suggesting that they could be related molecules (Loh et al., 1990). Moreover, the similarity between the three receptor subtypes is supported by the isolation of (i) anti-idiotypic monoclonal antibodies competing with both $\mu$ and $\delta$ ligands but not competing with $\kappa$ ligands (Gramsch et al., 1988; Coscia et al., 1991) and (ii) a monoclonal antibody raised against the purified $\mu$ receptor that interacts with both $\mu$ and $\kappa$ receptors (Bero et al., 1988).

Morphine interacts principally with $\mu$ receptors and peripheral administration of this opioid induces release of enkephalins (Bertolucci et al., 1992). The $\delta$ receptors bind with the greatest affinity to enkephalins and have a more discrete distribution in the brain than either $\mu$ or $\kappa$ receptors, with high concentrations in the basal ganglia and limbic regions. Thus, enkephalins may mediate part of the physiological response to morphine, presumably by interacting with $\delta$ receptors. Despite pharmacological and physiological heterogeneity, at least some types of opioid receptors inhibit adenylate cyclase, increase $K^+$ conductance, and inactivate $Ca^{2+}$ channels through a pertussis toxin-sensitive mechanism (Puttfarcken et al., 1988; Attali et al., 1989; Hsia et al., 1984). These results and others suggest that opioid receptors belong to the large family of cell surface receptors that signal through G proteins (Di Chiara et al., 1992; Loh et al., 1990).

Several attempts to clone cDNAs encoding opioid receptors have been reported. A cDNA encoding an opioid-binding protein (OBCAM) with $\mu$ selectivity was isolated (Schofield et al., 1989), but the predicted protein lacks transmembrane domains, presumed necessary for signal transduction. More recently, the isolation of another cDNA was reported, which was obtained by expression cloning (Xie et al., 1992). The deduced protein sequence displays seven putative transmembrane domains and is very similar to the human neuromedin K receptor. However, the affinity of opioid ligands for this receptor expressed in COS cells is two orders of magnitude below the expected value, and no subtype selectivity can be shown.

Many cell surface receptor/transmembrane systems consist of at least three membrane-bound polypeptide components: (a) a cell-surface receptor; (b) an effector, such as an ion channel or the enzyme adenylate cyclase; and (c) a guanine nucleotide-binding regulatory polypeptide or G protein, that is coupled to both the receptor and its effector.

G protein-coupled receptors mediate the actions of extracellular signals as diverse as light, odorants, peptide hormones and neurotransmitters. Such receptors have been identified in organisms as evolutionarily divergent as yeast and man. Nearly all G protein-coupled receptors bear sequence similarities with one another, and it is thought that all share a similar topological motif consisting of seven hydrophobic (and potentially $\alpha$-helical) segments that span the lipid bilayer (Dohlman et al., 1987; Dohlhman et al., 1991).

G proteins consist of three tightly associated subunits, $\alpha$, $\beta$ and $\gamma$ (1:1:1) in order of decreasing mass. Following agonist binding to the receptor, a conformational change is transmitted to the G protein, which causes the G$\alpha$-subunit to exchange a bound GDP for GTP and to dissociate from the $\beta\gamma$-subunits. The GTP-bound form of the $\alpha$-subunit is typically the effector-modulating moiety. Signal amplification results from the ability of a single receptor to activate many G protein molecules, and from the stimulation by G$\alpha$-GTP of many catalytic cycles of the effector.

The family of regulatory G proteins comprises a multiplicity of different $\alpha$-subunits (greater than twenty in man), which associate with a smaller pool of $\beta$ and $\gamma$-subunits (greater than four each) (Strothman and Simon, 1991). Thus, it is anticipated that differences in the $\alpha$-subunits probably distinguish the various G protein oligomers, although the targeting or function of the various $\alpha$-subunits might also depend on the $\beta\gamma$ subunits with which they associate (Strothman and Simon, 1991).

Improvements in cell culture and in pharmacological methods, and more recently, use of molecular cloning and gene expression techniques have led to the identification and characterization of many seven-transmembrane segment receptors, including new sub-types and sub-sub-types of previously identified receptors. The $\alpha_1$ and $\alpha_2$-adrenergic receptors once thought to each consist of single receptor species, are now known to each be encoded by at least three distinct genes (Kobilka et al., 1987; Regan et al., 1988; Cotecchia et al., 1988; Lomasney, 1990). In addition to rhodopsin in rod cells, which mediates vision in dim light, three highly similar cone pigments mediating color vision have been cloned (Nathans et al., 1986a; Nathans et al., 1986b). All of the family of G protein-coupled receptors appear to be similar to other members of the family of G protein-coupled receptors (e.g., dopaminergic, muscarinic, serotonergic, tachykinin, etc.), and each appears to share the characteristic seven-transmembrane segment topography.

When comparing the seven-transmembrane segment receptors with one another, a discernible pattern of amino acid sequence conservation is observed. Transmembrane domains are often the most similar, whereas the amino and carboxyl terminal regions and the cytoplasmic loop connecting transmembrane segments V and VI can be quite divergent (Dohlman et al., 1987).

Interaction with cytoplasmic polypeptides, such as kinases and G proteins, was predicted to involve the hydrophobic loops connecting the transmembrane domains of the receptor. The challenge, however, has been to determine which features are preserved among the seven-transmembrane segment receptors because of conservation of function, and which divergent features represent structural adaptations to new functions. A number of strategies have been used to test these ideas, including the use of recombinant DNA and gene expression techniques for the construction of substitution and deletion mutants, as well as of hybrid or chimeric receptors (Dohlman et al., 1991).

With the growing number of receptor sub-types, G-protein subunits, and effectors, characterization of ligand binding and G protein recognition properties of these receptors is an important area for investigation. It has long been known that multiple receptors can couple to a single G protein and, as in the case of epinephrine binding to $\beta_2$- and $\alpha_2$-adrenergic receptors, a single ligand can bind to multiple functionally distinct receptor sub-types. Moreover, G proteins with similar receptor and effector coupling specificities have also been identified. For example, three species of human $G_i$ have been cloned (Itoh et al., 1988), and alternate mRNA splicing has been shown to result in multiple variants of $G_s$ (Kozasa et al., 1988). Cloning and over production of the muscarinic and $\alpha_2$-adrenergic receptors led to the demonstration that a single receptor sub-type, when expressed at high levels in the cell, will couple to more than one type of G protein.

Opioid receptors are known to be sensitive to reducing agents, and the occurrence of a disulfide bridge has been postulated as essential for ligand binding (Gioannini et al., 1989). For rhodopsin, muscarinic, and β-adrenergic receptors, two conserved cysteine residues in each of the two first extracellular loops have been shown critical for stabilizing the functional protein structure and are presumed to do so by forming a disulfide bridge. Structure/function studies of opioid ligands have shown the importance of a protonated amine group for binding to the receptor with high affinity. The binding site of the receptor might, therefore, possess a critical negatively charged counterpart. Catecholamine receptors display in their sequence a conserved aspartate residue that has been shown necessary for binding the positively charged amine group of their ligands.

Given the complexity and apparent degeneracy of function of various opioid receptors, a question of fundamental importance is how, and under what circumstances do specific sub-type and sub-sub-type receptors exert their physiological effect in the presence of the appropriate stimulatory ligand. A traditional approach to answering this question has been to reconstitute the purified receptor and G protein components in vitro. Unfortunately, purification schemes have been successful for only a very limited number of receptor sub-types and their cognate G-proteins. Alternatively, heterologous expression systems can be of more general usefulness in the characterization of cloned receptors and in elucidating receptor G protein coupling specificity (Marullo et al., 1988; Payette et al., 1990; King et al., 1990).

One such system was recently developed in yeast cells, in which the genes for a mammalian $\beta_2$-adrenergic receptor and $G_s$ α-subunit were coexpressed (King et al., 1990). Expression of the $\beta_2$-adrenergic receptor to levels several hundred-fold higher than in any human tissue was attained, and ligand binding was shown to be of the appropriate affinity, specificity, and stereoselectivity. Moreover, a $\beta_2$-adrenergic receptor-mediated activation of the pheromone signal transduction pathway was demonstrated by several criteria, including imposition of growth arrest, morphological changes, and induction of a pheromone-responsive promoter (FUS1) fused to the *Escherichia coli* lac Z gene (encoding β-galactosidase) (King et al., 1990).

Finally, expression of a single receptor in the absence of other related sub-types is often impossible to achieve, even in isolated, non-recombinant mammalian cells. Thus, there has been considerable difficulty in applying the standard approaches of classical genetics or even the powerful techniques of molecular biology to the study of opioid receptors. In particular, means are needed for the identification of the DNA sequences encoding individual opioid receptors. Given such isolated, recombinant sequences, it is possible to address the heretofore intractable problems associated with design and testing of isoform-specific opioid receptor agonists and antagonists. The availability of cDNAS encoding the opioid receptors will permit detailed studies of signal-transduction mechanisms and reveal the anatomical distribution of the mRNAs of these receptors, providing information on their expression pattern in the nervous system. This information should ultimately allow better understanding of the opioid system in analgesia, and also the design of more specific therapeutic drugs.

Availability of polynucleotide sequences encoding opioid receptors, and the polypeptide sequences of the encoded receptors, will significantly increase the capability to design pharmaceutical compositions, such as analgesics, with enhanced specificity of function. In general, the availability of these polypeptide sequences will enable efficient screening of candidate compositions. The principle in operation through the screening process is straightforward: natural agonists and antagonists bind to cell-surface receptors and channels to produce physiological effects; certain other molecules bind to receptors and channels; therefore, certain other molecules may produce physiological effects and act as therapeutic pharmaceutical agents. Thus, the ability of candidate drugs to bind to opioid receptors can function as an extremely effective screening criterion for the selection of pharmaceutical compositions with a desired functional efficacy.

Prior methods for screening candidate drug compositions based on their ability to preferentially bind to cell-surface receptors has been limited to tissue-based techniques. In these techniques, animal tissues rich in the receptor type of interest are extracted and prepared; candidate drugs are then allowed to interact with the prepared tissue and those found to bind to the receptors are selected for further study. However, these tissue-based screening techniques suffer from several significant disadvantages. First, they are expensive because the source of receptor cell tissue—laboratory animals—is expensive. Second, extensive technical input is required to operate the screens. And, third, the screens may confuse the results because there are no tissues where only one receptor subtype is expressed exclusively. With traditional prior art screens you are basically looking at the wrong interactions or, at best, the proper interactions mixed in with a whole variety of unwanted interactions. An additional fundamental deficiency of animal tissue screens is that they contain animal receptors—ideal for the development of drugs for animals but of dubious value in human therapeutic agents.

A polynucleotide of the present invention, transfected into suitable host cells, can express polypeptide sequences corresponding to opioid receptors, both in large quantities and through relatively simple laboratory procedures. The result is the availability of extremely specific receptor-drug interactions free from the competitive and unwanted interactions encountered in tissue-based screens. Further expression in a microorganism where no such endogenous receptors exist (e.g. yeast cells or mutant mammalian cell lines) can be useful for screening and evaluating sub-type-selective drugs (Marullo et al., 1988; Payette et al., 1990; King et al., 1990).

BRIEF SUMMARY OF THE INVENTION

In one aspect, the present invention provides isolated and purified polynucleotides that encode a mu opioid receptor polypeptide a transcription regulatory polypeptide and/or opioid receptor like polypeptides. In a preferred embodiment, a polynucleotide of the present invention is a DNA molecule. Even more preferred, a polynucleotide of the present invention encodes a polypeptide comprising the amino acid residue sequence of SEQ ID NO: 2 or SEQ ID NO: 4, SEQ ID NO: 8 or SEQ ID NO: 17. Most preferably, an isolated and purified polynucleotide of the invention comprises the nucleotide base sequence of SEQ ID NO: 1, SEQ ID NO: 3, SEQ ID NO: 7 or SEQ ID NO: 16.

Yet another aspect of the present invention contemplates an isolated and purified polynucleotide comprising a base sequence that is identical or complementary to a segment of at least 35 contiguous bases of SEQ ID NO: 1, SEQ ID NO: 3, SEQ ID NO: 7 or SEQ ID NO: 16, wherein the polynucleotide hybridizes to a polynucleotide that encodes a mu opioid receptor polypeptide. Of course, polynucleotide segments of 15, 20, 25, 30, 35, 40, 45, 50, 55, 60, 65, 70, 80, 90, 100, 125, 150 or more contiguous bases are also expected to be of use in the invention. Preferably, an isolated and purified polynucleotide comprises a base sequence that is identical or complementary to a segment of at least 25 to 70 contiguous bases of SEQ ID NO: 1, SEQ ID NO: 3, SEQ ID NO: 7 or SEQ ID NO: 16. For example, a polynucleotide of the invention can comprise a segment of bases identical or complementary to 40 to 55 contiguous bases of the disclosed nucleotide sequences.

In still another embodiment of the present invention, there is provided an isolated and purified polynucleotide comprising a base sequence that is identical or complementary to a segment of at least 10 contiguous bases of SEQ ID NO: 1, wherein the polynucleotide of the invention hybridizes to SEQ ID NO: 1, or a complement of SEQ ID NO: 1. Of course, polynucleotide segments of 15, 20, 25, 30, 35, 40, 45, 50, 55, 60, 65, 70, 75, 80, 90, 100, 125, 150 or more contiguous bases are also expected to be of use in the invention. Preferably, the isolated and purified polynucleotide comprises a base sequence that is identical or complementary to a segment of at least 25 to 70 contiguous bases of SEQ ID NO: 1. For example, the polynucleotide of the invention can comprise a segment of bases identical or complementary to 40 to 55 contiguous bases of SEQ ID NO: 1.

Alternatively, the present invention contemplates an isolated and purified polynucleotide that comprises a base sequence that is identical or complementary to a segment of at least 10 contiguous bases of SEQ ID NO: 3, wherein the polynucleotide of the invention hybridizes to SEQ ID NO: 3, or a complement of SEQ ID NO: 3. Of course, polynucleotide segments of 15, 20, 25, 30, 35, 40, 45, 50, 55, 60, 65, 70, 80, 90, 100, 125, 150 or more contiguous bases are also expected to be of use in the invention. Preferably, the polynucleotide comprises a base sequence that is identical or complementary to a segment of at least 25 to 70 contiguous bases of SEQ ID NO: 3. For example, the polynucleotide can comprise a segment of bases identical or complementary to 40 to 55 contiguous bases of SEQ ID NO: 3.

The present invention also encompasses an isolated and purified polynucleotide that comprises a base sequence that is identical or complementary to a segment of at least 10 contiguous bases of SEQ ID NO: 7, wherein the polynucleotide of the invention hybridizes to SEQ ID NO: 7, or a complement of SEQ ID NO: 7. Of course, polynucleotide segments of 15, 20, 25, 30, 35, 40, 45, 50, 55, 60, 65, 70, 80, 90, 100, 125, 150 or more contiguous bases are also expected to be of use in the invention. Preferably, the polynucleotide comprises a base sequence that is identical or complementary to a segment of at least 25 to 70 contiguous bases of SEQ ID NO: 7. For example, the polynucleotide can comprise a segment of bases identical or complementary to 40 to 55 contiguous bases of SEQ ID NO: 7. In certain preferred embodiments, the claimed polynucleotide will include nucleotide number 150 of SEQ ID NO: 7.

The present invention also encompasses an isolated and purified polynucleotide that comprises a base sequence that is identical or complementary to a segment of at least 10 contiguous bases of SEQ ID NO: 16, wherein the polynucleotide of the invention hybridizes to SEQ ID NO: 16, or a complement of SEQ ID NO: 16. Of course, polynucleotide segments of 15, 20, 25, 30, 35, 40, 45, 50, 55, 60, 65, 70, 80, 90, 100, 125, 150 or more contiguous bases are also expected to be of use in the invention. Preferably, the polynucleotide comprises a base sequence that is identical or complementary to a segment of at least 25 to 70 contiguous bases of SEQ ID NO: 16. For example, the polynucleotide can comprise a segment of bases identical or complementary to 40 to 55 contiguous bases of SEQ ID NO: 16.

In another embodiment, the present invention contemplates an isolated and purified mu opioid receptor polypeptide, a gene transcription regulatory polypeptide. Preferably, a polypeptide of the invention is a recombinant polypeptide or an opioid receptor like polypeptide. Even more preferably, an opioid receptor polypeptide of the present invention comprises the amino acid residue sequence of SEQ ID NO: 2, SEQ ID NO: 8; a gene transcription regulatory polypeptide of the present invention comprises the amino acid residue sequence of SEQ ID NO: 4; and an opioid receptor like polypeptide of the present invention comprises the amino acid sequence of SEQ ID NO: 17.

The present invention comtemplates an isolated and purified mu opioid receptor polypeptide which has a $K_i$ for an opioid compound of between 1.0 M and 1.0 pM. Advantages are anticipated when the $K_i$ is between 10.0 nM and 0.1 nM. Preferrably, the $K_i$ is between 5.0 nM and 1.0 nM. The opioid compound is preferrably morphine, methadone, an enkephalin, an endorphin, or a dynorphin, dynorphin analog, or dynorphin metabolite. Most preferrably, the opioid compound is dynorphin A and the $K_i$ is between 2.0 nM and 1.0 nM.

In an alternative embodiment, the present invention provides an expression vector comprising a polynucleotide that encodes a polypeptide. Preferably, an expression vector of the present invention comprises a polynucleotide that encodes a polypeptide comprising the amino acid residue sequence of SEQ ID NO: 2 or SEQ ID NO: 4, SEQ ID NO: 8, or SEQ ID NO: 17. More preferably, an expression vector of the present invention comprises a polynucleotide comprising the nucleotide base sequence of SEQ ID NO: 1 or SEQ ID NO:3, SEQ ID NO: 7 or SEQ ID NO: 16. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxyl-terminal amino acid and within a transcriptional unit of the encoded polypeptide.

In yet another embodiment, the present invention provides a recombinant host cell transfected with a polynucleotide that encodes a polypeptide. Preferably, a recombinant host cell of the present invention is transfected with the polynucleotide of SEQ ID NO: 1, SEQ ID NO: 3, SEQ ID NO: 7 or SEQ ID NO: 16. Even more preferably, a host cell of the invention is a eukaryotic host cell. Still more preferably, a recombinant host cell of the present invention is a yeast cell. Alternatively, a recombinant host cell of the invention is a COS or CHO cell. In another aspect, a recombinant host cell of the present invention is a prokaryotic host cell. Preferably, a recombinant host cell of the invention is a bacterial cell of the DH5α strain of *Escherichia coli*. More preferably, a recombinant host cell comprises a polynucleotide under the transcriptional control of regulatory signals functional in the recombinant host cell, wherein the regulatory signals appropriately control expression of a mu opioid receptor polypeptide in a manner to enable all necessary transcriptional and post-transcriptional modification.

In yet another embodiment, the present invention contemplates a process of preparing a polypeptide comprising transfecting a cell with polynucleotide that encodes a polypeptide to produce a transformed host cell and maintaining the transformed host cell under biological conditions sufficient for expression of the polypeptide. Preferably, the transformed host cell is a eukaryotic cell. More preferably still, the eukaryotic cell is a COS or CHO cell. Alternatively, the host cell is a prokaryotic cell. More preferably, the prokaryotic cell is a bacterial cell of the DH5α strain of *Escherichia coli*. Even more preferably, a polynucleotide transfected into the transformed cell comprises the nucleotide base sequence of SEQ ID NO:1, SEQ ID NO:3, SEQ ID NO: 7 or SEQ ID NO: 16.

The invention provides a method of using a polynucleotide of the invention that encodes a polypeptide. This method involves preparing a vector in which a polynucleotide is positioned under the control of a promoter and introducing that vector into a recombinant cell. The recombinant cell is then cultured under conditions effective to allow expression of the encoded polypeptide. In some preferred embodiments, the encoded polypeptide will be a recombinant polypeptide.

In still another embodiment, the present invention provides an antibody immunoreactive with a claimed polypeptide. Preferably, an antibody of the invention is a monoclonal antibody. More preferably, a mu opioid receptor polypeptide comprises the amino acid residue sequence of SEQ ID NO: 2, SEQ ID NO: 4, SEQ ID NO: 8 or SEQ ID NO: 17.

In another aspect, the present invention contemplates a process of producing an antibody immunoreactive with a polypeptide of the invention comprising the steps of (a) transfecting a recombinant host cell with a polynucleotide that encodes a mu opioid receptor polypeptide; (b) culturing the host cell under conditions sufficient for expression of the polypeptide; (c) recovering the polypeptide; and (d) preparing the antibody to the polypeptide. Preferably, the host cell is transfected with the polynucleotide of SEQ ID NO: 1, SEQ ID NO: 3, SEQ ID NO: 7 or SEQ ID NO: 16. Alternatively, steps (a), (b) and (c) can be avoided by use of a synthetic polypeptide. Even more preferably, the present invention provides an antibody prepared according to the process described above.

Alternatively, the present invention provides a process of detecting a polypeptide according to the inventor, wherein the process comprises immunoreacting the polypeptide with an antibody prepared according to the process described above to form an antibody-polypeptide conjugate, and detecting the conjugate.

In yet another embodiment, the present invention contemplates a process of detecting a messenger RNA transcript that encodes a polypeptide of the invention, wherein the process comprises (a) hybridizing the messenger RNA transcript with a polynucleotide sequence that encodes the mu opioid receptor polypeptide to form a duplex; and (b) detecting the duplex. Alternatively, the present invention provides a process of detecting a DNA molecule that encodes a mu opioid receptor polypeptide, wherein the process comprises (a) hybridizing DNA molecules with a polynucleotide that encodes a mu opioid receptor polypeptide to form a duplex; and (b) detecting the duplex.

In another aspect, the present invention contemplates a diagnostic assay kit for detecting the presence of a polypeptide of the inventor in a biological sample, where the kit comprises a first container containing a first antibody capable of immunoreacting with a desired polypeptide, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label, fluorogenic label, biotin, or an enzyme.

In an alternative aspect, the present invention provides a diagnostic assay kit for detecting the presence, in biological samples, of a polynucleotide that encodes a polypeptide of the inventor, the kit comprising a first container that contains a second polynucleotide identical or complementary to a segment of at least 10 contiguous nucleotide bases of SEQ ID NO: 1, SEQ ID NO: 3, SEQ ID NO: 7 or SEQ ID NO: 16.

In another embodiment, the present invention contemplates a diagnostic assay kit for detecting the presence, in a biological sample, of an antibody immunoreactive with a polypeptide of the invention, the kit comprising a first container containing a polypeptide that immunoreacts with the antibody, with the polypeptide present in an amount sufficient to perform at least one assay.

In yet another aspect, the present invention contemplates a process of screening substances for their ability to interact with a a polypeptide of the invention comprising the steps of providing a polypeptide, obtaining a candidate substance, and testing the ability of selected substances to interact with the opioid receptor polypeptide. The interaction measured can be inter alia: the ability of the receptor to bind the candidate, the binding affinity, the intrinsic activation ability of the candidate activation of ion channels in the cell membrane, modulation of ion channels in the cell membranes, or modulation of cellular biochemical processes. These interactions can be measured by any of a number of means known in the art. By measuring these interactions, those of skill will be able to selectively modulate biochemical processes in the cells by selecting pharmacological compounds with desired characteristics.

This invention also encompasses a process for screening a substance for its properties in effecting opioid tolerance. Properties to be tested can be the receptor's ability to bind the candidate, the receptor's binding affinity for the candidate, and the candidates intrinsic activation of the receptor. Preferably, a substance to be screened is presented to a test cellular system; said system displays a physiologically measurable opioid response for quantification of changes in response indicating opioid tolerance. More preferably, a eucaryotic cell is used as test cellular system, containing mu opioid receptor. Still more preferably, the test cellular system displays measurable ionic currents upon stimulation of opioid receptor. Said measurable ionic currents may be endogenous to the test cellular system. Alternatively, ion channels may be introduced to the test cellular system to provide desired measurable response. Ion channels thus introduced may be in the form of protein or nucleic acids encoding the desired protein. The types of ion channels may include potassium channels and calcium channels. As one method of measuring opioid tolerance, the extent of response to mu opioid receptor activation may be determined to measure changes. The ability of a substance to affect such tolerance may be determined when the test cellular system is subjected to the exposure to said substance, and the results compared with the tolerance without such exposure.

The invention encompasses a method of screening substances for their ability to interact with a human mu opioid receptor comprising the steps of: obtaining a candidate substance, exposing cells expressing a reporter gene under the control of a mu opioid receptor promoter to the candidate substance, and measuring expression of the reporter gene in the presence or absence of the candidate substance. In certain embodiments, the reporter gene can encode beta-galactosidase. In another embodiment, the reporter gene can encode chloramphenicol acetyltransferase.

This invention also encompasses a method for screening individual responsiveness to opioids. Preferably, the sequence content of an individual's genetic composition is determined, and variations at the nucleic acid level among different individuals constitute polymorphisms. More preferably, the sequence content for mu opioid receptor is determined. In one embodiment of utilizing information of polymorphism, nucleic acids bearing such polymorphism may be subjected to physiological characterization of a cellular or metabolic process to determine functional impact of such polymorphism. Preferably, test of functional impact may be indicated by binding to a substance. Alternatively, test may be performed by physiological measurements including activity of adenylyl cyclase or modulation of ion channels. This method for screening individual responsiveness provides information that may be used for diagnosis of the individual's ability to respond to certain medical intervention. For example, one individual with a high affinity mu opioid receptor for dynorphin may respond favorably to treatment of dynorphin and dynorphin analogues, whereas another individual with a low affinity mu opioid receptor for dynorphin may caution a diminished response which is either undesirable or requires elevated doses of drug. This method may enable a genetic-based diagnosis approach in addition to, or instead of, traditional laboratory tests that do not determine an individual's genetic content.

BRIEF DESCRIPTION OF THE DRAWINGS

FIG. 6. Panels A, B, and C of FIG. 6 show Human μ Opioid Receptor Coupling to the G Protein-Activated $K^+$ Channel Electrophysiological analysis of oocytes injected with RNAs encoding the human μ opioid receptor and the G protein-activated $K^+$ channel. Membrane current traces were recorded at a holding potential of −80 mV. Oocytes were bathed in a high $K^+$ solution and were exposed to either (A) 1 μM DAMGO or (B) 1 μM DAMGO plus 10 μM naloxone. Inward current is downward. (C) The current-voltage relationship plotted as an I vs. V curve. DAMGO-induced membrane currents were recorded with voltage steps ranging from −160 mV to 0 mV. The DAMGO-induced net currents were derived by subtracting the currents recorded before DAMGO application from those during DAMGO application.

FIG. 7. Panels A, B, and C of FIG. 7 show Desensitization of the Human μ Opioid Receptor-$K^+$ Channel Coupling and the Effect of PKC Membrane currents were recorded in oocytes injected with both the human μ opioid receptor and the $K^+$ channel mRNAs. (A, top), a schematic diagram of the experimental protocol. The oocyte was voltage-clamped at −80 mV and superfused with 500 nM DAMGO in HK solution to elicit the $K^+$ current. After the first DAMGO stimulation, the superfusate was switched to ND96 containing 1.8 mM CaCl2 and the oocyte either received no treatment or was subjected to drug treatment or enzyme injection. The superfusate was then switched back to HK solution to record the second DAMGO-induced membrane current. (A, middle), the ramp voltage command used to record currents before and during DAMGO stimulation. From a holding potential of −80 mV, the membrane voltage was stepped to −160 mV, and ramped to +40 mV before stepping back to the holding potential. Net currents were derived by subtracting the currents before DAMGO application from those during DAMGO application. (A, bottom), the step voltage commands used to record currents before and during DAMGO application. The step command ranged from −160 mV to +40 mV, with 20 mV increments. Net currents were derived by subtracting the currents before DAMGO application from those during DAMGO application. (B), membrane currents elicited by DAMGO application before and after treatment with 100 nM phorbol 12-myristate 13-acetate (PMA) for 10–15 min. (B, top), current recorded at a holding potential of −80 mV. (B, middle and bottom), net currents from the first and second DAMGO applications are obtained from either ramped (middle) or stepped (bottom) voltage commands. (C), membrane currents recorded during DAMGO application before and after treatment with 100 nM 4α-phorbol for 10–15 min. (C, top/middle/bottom), membrane currents are recorded and displayed as in (B).

FIG. 8. Panels A and B of FIG. 8 show Effect of CaM Kinase II on the Coupling Between the Human μ Opioid Receptor and $K^+$ Channel Membrane currents were recorded in oocytes injected with both the human μ opioid receptor and the $K^+$ channel mRNAs. Experimental protocol and voltage commands are as described in FIG. 7. (A, top/middle/bottom), membrane currents recorded during DAMGO application before and after injection of activated CaM kinase II. (A, top), current recorded at a holding potential of −80 mV. (A, middle and bottom), net currents from the first and second DAMGO applications are obtained from ramped (middle) or stepped (bottom) voltage commands. (B, top/middle/bottom), membrane currents recorded during DAMGO application before and after injection of boiled CaM kinase II. Membrane currents are recorded and displayed as in the top, middle and bottom panels of A.

FIG. 18. Panels A and B of FIG. 18 show Coupling of the $\mu$ opioid receptor to the G protein-activated K$^+$ channel. Electrophysiologic analysis of oocytes injected with mRNAs for the rat $\mu$ opioid receptor and the G protein-activated K$^+$ channel. (A) Membrane current traces recorded at a holding potential of −80 mV. Oocytes were exposed to 1 $\mu$M of DAMGO (left trace) or 1 $\mu$M of DAMGO plus 10 $\mu$M of naloxone (right trace) as indicated. Inward current is downward. (B) Membrane currents recorded with voltage steps ranging from −160 mV to +40 mV were recorded before and 1 min after DAMGO superfusion. The DAMGO-induced net currents were derived by subtracting the currents before DAMGO application from those after, and are shown in the left panel. The right panel shows the I–V curve of the these currents.

DETAILED DESCRIPTION OF THE PREFERRED EMBODIMENTS

I. The Invention

Figure 1A:
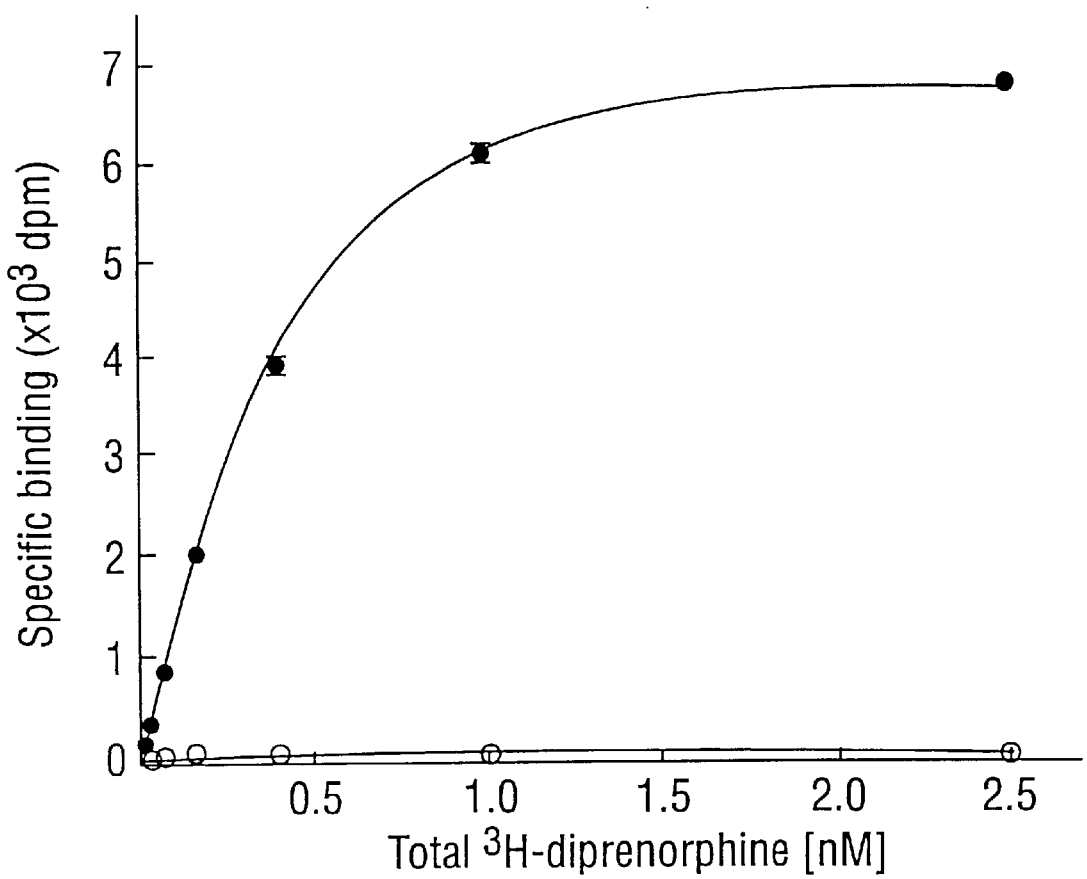
FIG. 1. Saturation Binding of [$^3$H]Diprenorphine Using COS-7 Cell Membranes [$^3$H]Diprenorphine binding was determined using membranes prepared from COS-7 cells transfected with either the rat MOR-1 cDNA plasmid (●) or the parental vector (○). Data from a representative experiment are presented and are expressed as mean±standard error. Inset, Scatchard plot analysis of the binding data from MOR-1-transfected cells.
Figure 1B:
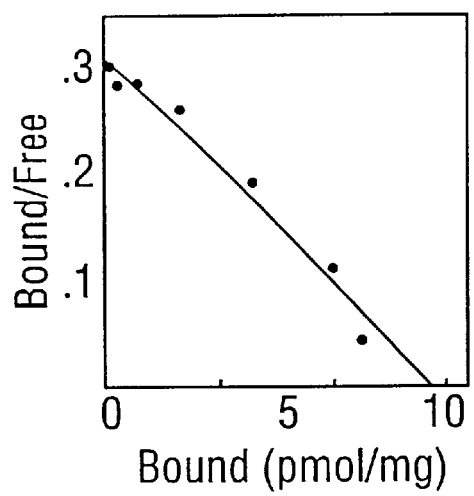

The present invention provides DNA segments, purified polypeptides, methods for obtaining antibodies, methods of cloning and using recombinant host cells necessary to obtain and use recombinant mu opioid receptors. Thus, the difficulties encountered with applying the standard approaches of classical genetics or techniques in molecular biology evident in the prior art to mu opioid receptors, have been overcome. Accordingly, the present invention concerns generally compositions and methods for the preparation and use of mu opioid receptors.

II. Polynucleotide

A. Isolated and Purified Polynucleotides that Encode Mu Opioid Receptor Polypeptides.

In one aspect, the present invention provides an isolated and purified polynucleotide that encodes a mu opioid receptor polypeptide. In a preferred embodiment, the polynucleotide of the present invention is a DNA molecule. Even more preferred, a polynucleotide of the present invention encodes a polypeptide comprising the amino acid residue sequence of SEQ ID NO: 2, SEQ ID NO: 4, SEQ ID NO: 8 or SEQ ID NO: 17. Most preferably, an isolated and purified polynucleotide of the invention comprises the nucleotide base sequence of SEQ ID NO: 1, SEQ ID NO: 3, SEQ ID NO: 7 or SEQ ID NO: 16.

As used herein, the term "polynucleotide" means a sequence of nucleotides connected by phosphodiester linkages. Polynucleotides are presented herein in the direction from the 5' to the 3' direction. A polynucleotide of the present invention can comprise from about 680 to about several hundred thousand base pairs. Preferably, a polynucleotide comprises from about 680 to about 150,000 base pairs. Preferred lengths of particular polynucleotide are set forth hereinafter.

A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U).

A polynucleotide of the present invention can be prepared using standard techniques well known to one of skill in the art. The preparation of a cDNA molecule encoding a mu opioid receptor polypeptide of the present invention is described hereinafter in Examples 1, 2, 4, and 12. A polynucleotide can also be prepared from genomic DNA libraries using lambda phage technologies.

In another aspect, the present invention provides an isolated and purified polynucleotide that encodes a mu opioid receptor polypeptide, where the polynucleotide is preparable by a process comprising the steps of constructing a library of cDNA clones from a cell that expresses the polypeptide; screening the library with a labelled cDNA probe prepared from RNA that encodes the polypeptide; and selecting a clone that hybridizes to the probe. Preferably, the polynucleotide of the invention is prepared by the above process. More preferably, the polynucleotide of the invention encodes a polypeptide that has the amino acid residue sequence of SEQ ID NO: 2, SEQ ID NO: 4, SEQ ID NO: 8 or SEQ ID NO: 17. More preferably still, the polynucleotide comprises the nucleotide sequence of SEQ ID NO: 1, SEQ ID NO: 3, SEQ ID NO: 7 or SEQ ID NO: 16.

B. Probes and Primers.

In another aspect, DNA sequence information provided by the present invention allows for the preparation of relatively short DNA (or RNA) sequences having the ability to specifically hybridize to gene sequences of the selected polynucleotide disclosed herein. In these aspects, nucleic acid probes of an appropriate length are prepared based on a consideration of a selected nucleotide sequence, e.g., a sequence such as that shown in SEQ ID NO: 1, SEQ ID NO: 3, SEQ ID NO: 7 or SEQ ID NO: 17. The ability of such nucleic acid probes to specifically hybridize to a polynucleotide encoding a mu opioid receptor lends them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a gene or polynucleotide that encodes a mu opioid receptor polypeptide from mammalian cells using PCR technology.

To provide certain of the advantages in accordance with the present invention, a preferred nucleic acid sequence employed for hybridization studies or assays includes probe molecules that are complementary to at least a 10 to 70 or so long nucleotide stretch of a polynucleotide that encodes a mu opioid receptor polypeptide, such as that shown in SEQ ID NOS: 1, 3, 7 or 16. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 25 to 40 nucleotides, 55 to 70 nucleotides, or even longer where desired. Of course, polynucleotide segments of 15, 20, 25, 30, 35, 40, 45, 50, 55, 60, 65, 70, 80, 90, 100, or more contiguous bases are also expected to be of use in the invention. Such fragments can be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction enzyme sites.

In another aspect, the present invention contemplates an isolated and purified polynucleotide comprising a base sequence that is identical or complementary to a segment of at least 10 contiguous bases of SEQ ID NO: 1, SEQ ID NO: 3, SEQ ID NO: 7 or SEQ ID NO: 16, wherein the polynucleotide hybridizes to a polynucleotide that encodes a mu opioid receptor polypeptide. Of course, polynucleotide segments of 15, 20, 25, 30, 35, 40, 45, 50, 55, 60, 65, 70, 80, 90, 100, or more contiguous bases are also expected to be of use in the invention. Preferably, the isolated and purified polynucleotide comprises a base sequence that is identical or complementary to a segment of at least 25 to 70 contiguous bases of SEQ ID NO: 1, SEQ ID NO: 3, SEQ ID NO: 7 or SEQ ID NO: 16. For example, the polynucleotide of the invention can comprise a segment of bases identical or complementary to 40 or 55 contiguous bases of the disclosed nucleotide sequences.

Accordingly, a polynucleotide probe molecule of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and/or high temperature conditions, such as provided by 0.02 M–0.15 M NaCl at temperatures of 50° C. to 70° C. Those conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate a mu opioid receptor polypeptide coding sequence from other cells, functional equivalents, or the like, less stringent hybridization conditions are typically needed to allow formation of the heteroduplex. In these circumstances, one can desire to employ conditions such as 0.15 M–0.9 M salt, at temperatures ranging from 20° C. to 70° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In still another embodiment of the present invention, there is provided an isolated and purified polynucleotide comprising a base sequence that is identical or complementary to a segment of at least 10 contiguous bases of SEQ ID NO: 1. The polynucleotide of the invention hybridizes to SEQ ID NO: 1, or a complement of SEQ ID NO: 1. Of course, polynucleotide segments of 15, 20, 25, 30, 35, 40, 45, 50, 55, 60, 65, 70, 80, 90, 100, 125, 150 or more contiguous bases are also expected to be of use in the invention. Preferably, the isolated and purified polynucleotide comprises a base sequence that is identical or complementary to a segment of at least 25 to 70 contiguous bases of SEQ ID NO: 1. For example, the polynucleotide of the invention can comprise a segment of bases identical or complementary to 40 to 55 contiguous bases of SEQ ID NO: 1.

Alternatively, the present invention contemplates an isolated and purified polynucleotide that comprises a base sequence that is identical or complementary to a segment of at least 10 contiguous bases of SEQ ID NO: 3. The polynucleotide of the invention hybridizes to SEQ ID NO: 3, or a complement of SEQ ID NO: 3. Of course, polynucleotide segments of 15, 20, 25, 30, 35, 40, 45, 50, 55, 60, 65, 70, 80, 90, 100, 125, 150 or more contiguous bases are also expected to be of use in the invention. Preferably, the polynucleotide comprises a base sequence that is identical or complementary to a segment of at least 25 to 70 contiguous bases of SEQ ID NO: 3. For example, the polynucleotide can comprise a segment of bases identical or complementary to 40 to 55 contiguous bases of SEQ ID NO: 3.

The present invention also encompasses an isolated and purified polynucleotide that comprises a base sequence that is identical or complementary to a segment of at least 10 contiguous bases of SEQ ID NO: 7. The polynucleotide of the invention hybridizes to SEQ ID NO: 7, or a complement of SEQ ID NO: 7. Of course, polynucleotide segments of 15, 20, 25, 30, 35, 40, 45, 50, 55, 60, 65, 70, 80, 90, 100, 125, 150 or more contiguous bases are also expected to be of use in the invention. Preferably, the polynucleotide comprises a base sequence that is identical or complementary to a segment of at least 25 to 70 contiguous bases of SEQ ID NO: 7. For example, the polynucleotide can comprise a segment of bases identical or complementary to 40 to 55 contiguous bases of SEQ ID NO: 7.

The present invention also encompasses an isolated and purified polynucleotide that comprises a base sequence that is identical or complementary to a segment of at least 10 contiguous bases of SEQ ID NO: 16. The polynucleotide of the invention hybridizes to SEQ ID NO: 16, or a complement of SEQ ID NO: 16. Of course, polynucleotide segments of 15, 20, 25, 30, 35, 40, 45, 50, 55, 60, 65, 70, 80, 90, 100, 125, 150 or more contiguous bases are also expected to be of use in the invention. Preferably, the polynucleotide comprises a base sequence that is identical or complementary to a segment of at least 25 to 70 contiguous bases of SEQ ID NO: 16. For example, the polynucleotide can comprise a segment of bases identical or complementary to 40 to 55 contiguous bases of SEQ ID NO: 16.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C contents, type of target nucleic acid, source of nucleic acid, size of hybridization probe). Following washing of the matrix to remove non-specifically bound probe molecules, specific hybridization is detected, or even quantified, by means of the label.

III. Mu Opioid Receptor Polypeptide and Gene Transcription Regulatory Polypeptide In one embodiment, the present invention contemplates an isolated and purified mu opioid receptor polypeptide. Preferably, a mu opioid receptor polypeptide of the invention is a recombinant polypeptide. Even more preferably, a mu opioid receptor polypeptides of the present invention comprises the amino acid residue sequence of SEQ ID NO: 2 or SEQ ID NO: 8. A mu opioid receptor polypeptide preferably comprises less than about 500 amino acid residues and, more preferably no more than about 400 amino acid residues.

In another embodiment, the present invention contemplates an isolated and purified gene transcription regulatory polypeptide. Preferably, a gene transcription regulatory polypeptide of the invention is a recombinant polypeptide. Even more preferably, gene transcription regulatory polypeptides of the present invention comprises the amino acid residue sequence of SEQ ID NO:4. A gene transcription regulatory polypeptide preferably comprises less than about 500 amino acid residues and, more preferably less than about 400 amino acid residues.

Polypeptides are disclosed herein as amino acid residue sequences. Those sequences are written left to right in the direction from the amino to the carboxyl terminus. In accordance with standard nomenclature, amino acid residue sequences are denominated by either a single letter or a three letter code as indicated below.

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having like opioid receptor characteristics. For example, certain amino acids can be substituted for other amino acids in a sequence without appreciable loss of receptor activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte and Doolittle, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below). The present invention thus contemplates functional or biological equivalents of a mu opioid receptor polypeptide as set forth above.

TABLE 1

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by (Adelman et al., 1983). As will be appreciated, the technique typically employs a phage vector which can exist in both a single stranded and double stranded form. Typical vectors useful in site-directed mutagenesis include vectors such as the M13 phage (Messing et al., 1981). These phage are commercially available and their use is generally known to those of skill in the art.

In general, site-directed mutagenesis in accordance herewith is performed by first obtaining a single-stranded vector which includes within its sequence a DNA sequence which encodes all or a portion of the mu opioid receptor polypeptide sequence selected. An oligonucleotide primer bearing the desired mutated sequence is prepared, generally synthetically, for example, by the method of (Crea et al., 1978). This primer is then annealed to the singled-stranded vector, and extended by the use of enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutation. Commercially available kits come with all the reagents necessary, except the oligonucleotide primers.

Amino acid residues can be added to or deleted from the mu opioid receptor polypeptide through the use of standard molecular biological techniques without altering the functionality of the receptor. For example, portions of the mu opioid receptor can be removed to create truncated opioid receptors. The truncated receptor retains the properties of mu opioid receptors such as ligand binding and the ability to interact with other proteins (G proteins, adenylyl cyclase, for example). Functional truncated proteins have been reported for phosphodiesterases, ion channels, and membrane transporters. As used herein, truncated receptors are receptors in which amino acids have been removed from the wild type receptor to create a shorter receptor or portions thereof. As used herein, chimeric receptors are receptors in which amino acids have been added to the receptor. A chimeric receptor can be shorter, longer or the same length as the wild type receptor.

The functional activity of truncated and chimeric receptors have been demonstrated in a number of receptor systems. In particular, truncated and chimeric adrenergic receptors, which are structurally similar to the opioid receptors, have been shown to retain functional properties of the wild type adrenergic receptor (Frielle et al., 1980; Kobilka et al., 1988).

Most of the long carboxyl terminus of the avian $\beta$-adrenergic receptor can be deleted or proteolytically removed without altering the ligand-binding properties or regulatory properties of the receptor. The ligand binding properties of five truncated $\beta$-adrenergic receptors for both agonists and antagonists were found to be similar to those of the wild type receptor. Furthermore, truncated adrenergic receptors also stimulated adenylyl cyclase activity. In fact, truncated $\beta$-adrenergic receptors, in the presence of agonists, showed a greater stimulation of adenylyl cyclase activity than the stimulation achieved by the wild type receptor. (Parker et al., 1991).

Similar results were obtained for the $\alpha$-adrenergic receptor. A truncated $\alpha$-adrenergic receptor activated phosphatidyl inositol hydrolysis as effectively as wild type $\alpha$-adrenergic receptor. (Cotecchia et al., 1989).

Functional chimeric receptors have also been created by a number of investigators. Functional chimeric adrenergic receptors were created by splicing together sections of the $\alpha_2$ and $\beta_2$ adrenergic receptors. (Kobilka et al., 1988). Functional chimeras have also been generated for the following receptors: between $\beta_1$ and $\beta_2$ receptors, (Frielle et al., 1988; Marullo et al., 1990); between m2 and m3 muscarinic receptors, (Wess et al., 1990); between m1 muscarinic and $\beta$ adrenergic receptors, (Wong et al., (1990); between $D_2$ dopamine and m1 muscarinic receptors, (England et al., 1991); between luteinizing hormone and $\beta$ adrenergic receptors, (Moyle et al., 1991); between $NK_1$ and $NK_3$ substance P receptors, (Gether et al., 1993); and platelet-derived growth factor and epidermal growth factor receptors, (Seedorf et al., 1991).

Chimeric mu opioid receptors can be created by splicing sections of a second receptor to a mu receptor. The two receptors can be similar to each other. Thus, for the creation of chimeric mu opioid receptors, other opioid receptors, such as sigma, delta, and kappa opioid receptors, are ideal sources for nucleotide sequences. For example, a transmembrane domain in the mu opioid receptor can be substituted with an analogous transmembrane domain from sigma, delta or kappa opioid receptor. It is contemplated that the nucleotide source of the second receptor is not limited to opioid receptors. Chimeric receptors can be created from mu opioid receptor and other similar receptors such as acetylcholine, adenosine, adrenergic, angiotensin, bombesin, bradykinin, cannabinoid, dopamine, endothelin, histamine, interleukin, luteinizing hormone, neuromedin K, neuropeptide Y, odorant, prostaglandin, parathyroid hormone, serotonin, somatostatin, substance K, substance P, thrombin, thromboxane A2, thyrotropin releasing hormone and vasopressin receptors.

A mu opioid receptor polypeptide of the present invention is understood not to be limited to a particular source. As disclosed herein, the techniques and compositions of the present invention provide, for example, the identification and isolation of mu opioid receptors from rodent sources. Thus, the invention provides for the general detection and isolation of the genus of mu opioid receptor polypeptides from a variety of sources. It is believed that a number of species of the family of mu opioid receptor polypeptides are amenable to detection and isolation using the compositions and methods of the present inventions.

A polypeptide of the present invention is prepared by standard techniques well known to those skilled in the art. Such techniques include, but are not limited to, isolation and purification from tissues known to contain that polypeptide, and expression from cloned DNA that encodes such a polypeptide using transformed cells (See Examples 1 and 2, hereinafter).

Opioid receptor polypeptides are found in virtually all mammals including human. The sequence of a mouse delta opioid receptor has been previously described (Kieffer et al., 1992; Evans et al., 1992). As is the case with other receptors, there is likely little variation between the structure and function of an opioid receptor in different species. Where there is a difference between species, identification of those differences is well within the skill of an artisan. Thus, the present invention contemplates a mu opioid receptor polypeptide from any mammal. A preferred mammal is a rodent or a human.

Regulation of gene expression in a cell is accomplished through many different mechanisms. A well known mechanism of gene expression regulation is through the use of a zinc finger motif in a transcription regulatory polypeptide. The zinc finger domain found in many transcription factors binds to DNA to regulate transcription. Zinc finger domains are nucleic acid-binding protein structures first identified in the Xenopus transcription factor TFIIIA. These domains have since been found in numerous nucleic acid-binding proteins. (Klug and Rhodes, 1987; Evans and Hollenberg, 1988; Payre and Vincent, 1988; Miller et al., 1985; Berg, 1988).

A zinc finger domain is composed of 25 to 30 amino acid residues. There are two cysteine or histidine residues at both extremities of the domain, which are most probably involved in the tetrahedral coordination of a zinc atom. Each zinc finger likely binds to the major groove of B-DNA so as to interact with ~5 successive base pairs; that is, with about a half-turn of B-DNA. A zinc finger protein thus can bind to DNA in which the protein binds along one face of the DNA with successive zinc fingers bound in the major groove on alternate sides of the double helix. Zinc fingers likely form structural "scaffolds" that match the double helix's three dimensional contour. Base sequence specificity is presumably provided by the particular sequence of each zinc finger's variable residues. (Klug and Rhodes, 1987). A schematic representation of a zinc finger domain as shown below:

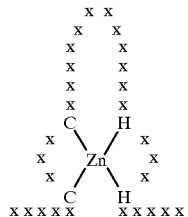

Zinc fingers have been identified in many transcription factors including Sp1, estrogen, and glucocorticoid receptors, several Drosophila developmental regulators, and the Xenopus Xfin protein, as well as in the *E. coli* UvrA protein and certain retroviral nucleic acid binding proteins.

Xenopus transcription factor IIIA (TFIIIA) is a regulatory protein which contains nine zinc fingers. The 344-residue TFIIIA contains 9 similar, tandemly repeated, ~30-residue units, each of which contains two invariant cysteine residues, two invariant histidine residues, and several conserved hydrophobic residues. Each of these units binds a $Zn^{2+}$ ion. X-ray absorption measurements indicate that the $Zn^{2+}$ ion is tetrahedrally coordinated to the invariant cysteine and histidine residues. Sequence analysis of a number of transcription regulators has revealed that the zinc finger motif occurs between about 2 to 40 times in a transcription regulator.

Two major classes of zinc fingers are characterized according to the number and positions of the histidine and cysteine residues involved in the zinc atom coordination. In the first class, called C2H2, the first pair of zinc coordinating residues are cysteines, while the second pair are histidines. Transcription factor TFIIIA is the prototype example for this class of zinc fingers. A number of experimental reports have demonstrated the zinc-dependent DNA or RNA binding property of some members of this class. The other class of zinc fingers, called C4, groups together many different regulatory proteins that happen to have several cysteines within a short stretch of sequence. The steroid hormone receptors are an example of proteins belonging to this class.

Some of the proteins which are known to include C2H2-type zinc fingers are listed below. The number of zinc finger regions found in each of these proteins have been indicated between brackets; a '+' symbol indicates that only partial sequence data is available and that additional finger domains may be present.

Xenopus: transcription factor TFIIIA (9), Xfin (37), XlcOF10 (7), XlcOF22 (12).

Drosophila: Glass (5), Hunchback (6), Kruppel (5), Kruppel-H (4+), Snail(5), Serependity locus beta (6), delta (7), and h-1 (8), Suppressor of hairy wing su(Hw) (12), Tramtrack (2).

Yeast: transcriptional activator ADR1 (2), transcriptional factor SWI5 (3).

*Aspergillus nidulans*: developmental protein brlA (2).

Mammalian: transcription factor Sp1 (3), ZfX (13), ZfY (13), Zfp-35 (18), EGR1/Krox24 (3), EGR2/Krox20 (3), Evi-1 (10), GLI1 (5), GLI2 (4+),GLI3 (3+), KR1 (9+), KR2 (9), KR3 (15+), KR4 (14+), KR5 (11+), HF.10 (10), HF.12 (6+).

Sequence analysis of rat mu opioid receptor reveals that in an alternate reading frame, the cDNA of the mu opioid receptor (SEQUENCE ID NO: 1) codes for a polypeptide which contains a zinc finger motif (SEQUENCE ID NO: 3 and SEQUENCE ID NO: 4). The zinc finger containing polypeptide comprises 298 amino acids encoded by nucleotides 339 to 1235. The zinc finger containing polypeptide is smaller by 100 amino acids than the mu opioid receptor. SEQUENCE ID NO: 3 shows the alternate reading frame of a mu opioid receptor that encodes the transcription regulatory polypeptide. In particular, there is a zinc finger motif, of the C2H2 class, located between amino acid residues 155 and 178 of this protein. This motif fits the consensus pattern of C-x(2,4)-C-x(12)-H-x(3,5)-H for the C2H2 class, with 4 amino acid residues each in between the two cysteines at the amino end of the motif and the two histidines at the carboxyl end of the motif. The C2H2 zinc finger motif has been found in many proteins, including mammalian transcription factor Sp1 as discussed above.

It is likely that the zinc finger polypeptide of the mu opioid receptor is involved in the autoregulation of the expression of the mu opioid receptor. The polynucleotide that encodes the zinc finger polypeptide and the gene transcription regulatory polypeptide is useful in controlling the expression of the mu opioid receptor. An antibody immunoreactive with the gene transcription regulatory polypeptide can be used to regulate the expression of the mu opioid receptor. Alternatively, anti-sense mRNA can be used to regulate the expression of the mu opioid receptor.

In another embodiment, the polynucleotide that encodes the gene transcription regulatory polypeptide can be used to identify other polynucleotides that encode a mu opioid receptor or a transcription regulatory polypeptide.

IV. Expression Vectors

The present invention provides expression vectors comprising polynucleotide that encode mu opioid receptor polypeptides, or a polynucleotide that encodes a gene transcription regulatory polypeptide. Preferably, expression vectors of the present invention comprise polynucleotides that encode polypeptides comprising the amino acid residue sequence of SEQ ID NO: 2, SEQ ID NO: 4, SEQ ID NO: 8 or SEQ ID NO: 17. More preferably, expression vectors of the present invention comprise polynucleotides comprising the nucleotide base sequence of SEQ ID NO: 1, SEQ ID NO: 3, SEQ ID NO: 7 or SEQ ID NO: 16. Even more preferably, expression vectors of the invention comprise polynucleotides operatively linked to an enhancer-promoter. More preferably still, expression vectors of the invention comprise a polynucleotide operatively linked to a prokaryotic promoter. Alternatively, expression vectors of the present invention comprise a polynucleotide operatively linked to an enhancer-promoter that is a eukaryotic promoter. Expression vectors further comprise a polyadenylation signal that is positioned 3' of the carboxyl-terminal amino acid and within a transcriptional unit of the encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (RNA). Transcription-terminating regions are well known in the art. A preferred transcription-terminating region is derived from a bovine growth hormone gene.

An expression vector comprises a polynucleotide that encodes a mu opioid receptor polypeptide. Such a polypeptide is meant to include a sequence of nucleotide bases encoding a mu opioid receptor polypeptide sufficient in length to distinguish said segment from a polynucleotide segment encoding a non-opioid receptor polypeptide. A polypeptide of the invention can also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed herein using a mutagenic procedure such as site-directed mutagenesis.

Preferably, expression vectors of the present invention comprise polynucleotides that encode polypeptides comprising the amino acid residue sequence of SEQ ID NO: 2, SEQ ID NO: 4, SEQ ID NO: 8 or SEQ ID NO: 17. An expression vector can include a mu opioid receptor polypeptide coding region itself of any of the mu opioid receptor polypeptides noted above or it can contain coding regions bearing selected alterations or modifications in the basic coding region of such a mu opioid receptor polypeptide. Alternatively, such vectors or fragments can code larger polypeptides or polypeptides which nevertheless include the basic coding region. In any event, it should be appreciated that due to codon redundancy as well as biological functional equivalence, this aspect of the invention is not limited to the particular DNA molecules corresponding to the polypeptide sequences noted above.

Exemplary vectors include the mammalian expression vectors of the pCMV family including pCMV6b and pCMV6c (Chiron Corp., Emeryville, Calif.) and pRc/CMV (Invitrogen, San Diego, Calif.). In certain cases, and specifically in the case of these individual mammalian expression vectors, the resulting constructs can require co-transfection with a vector containing a selectable marker such as pSV2neo. Via co-transfection into a dihydrofolate reductase-deficient Chinese hamster ovary cell line, such as DG44, clones expressing opioid polypeptides by virtue of DNA incorporated into such expression vectors can be detected.

A DNA molecule of the present invention can be incorporated into a vector using a number of techniques which are well known in the art. For instance, the vector pUC18 has been demonstrated to be of particular value. Likewise, the related vectors M13mp18 and M13mp19 can be used in certain embodiments of the invention, in particular, in performing dideoxy sequencing.

An expression vector of the present invention is useful both as a means for preparing quantities of the mu opioid receptor polypeptide-encoding DNA itself, and as a means for preparing the encoded polypeptides. It is contemplated that where mu opioid receptor polypeptides of the invention are made by recombinant means, one can employ either prokaryotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukaryotic mu opioid receptor polypeptides are anticipated using the teaching of the disclosed invention, one likely expresses such sequences in eukaryotic hosts. However, even where the DNA segment encodes a eukaryotic mu opioid receptor polypeptide, it is contemplated that prokaryotic expression can have some additional applicability. Therefore, the invention can be used in combination with vectors which can shuttle between the eukaryotic and prokaryotic cells. Such a system is described herein which allows the use of bacterial host cells as well as eukaryotic host cells.

Where expression of recombinant polypeptide of the present invention is desired and a eukaryotic host is contemplated, it is most desirable to employ a vector, such as a plasmid, that incorporates a eukaryotic origin of replication. Additionally, for the purposes of expression in eukaryotic systems, one desires to position the opioid receptor encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the mu opioid receptor polypeptide, an appropriate polyadenylation site.

The pRc/CMV vector (available from Invitrogen) is an exemplary vector for expressing a mu opioid receptor or a gene transcription regulatory polypeptide in mammalian cells, particularly COS and CHO cells. A polypeptide of the present invention under the control of a CMV promoter can be efficiently expressed in mammalian cells. A detailed description of using and expressing a mu opioid receptor in the vector pRc/CMV is provided in examples 2 and 3 of the present application.

pCMV vectors is another exemplary vector. The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region of each plasmid. The pCMV4 vector differs from these 4 plasmids in containing a translation enhancer in the sequence prior to the polylinker. While they are not directly derived from the pCMV1–5 series of vectors, the functionally similar pCMV6b and c vectors are available from the Chiron Corp. of Emeryville, Calif. and are identical except for the orientation of the polylinker region which is reversed in one relative to the other.

The universal components of the pCMV plasmids are as follows. The vector backbone is pTZ18R (Pharmacia), and contains a bacteriophage f1 origin of replication for production of single stranded DNA and an ampicillin-resistance gene. The CMV region consists of nucleotides −760 to +3 of the powerful promoter-regulatory region of the human cytomegalovirus (Towne stain) major immediate early gene (Thomsen et al., 1984; Boshart et al., 1985). The human growth hormone fragment (hGH) contains transcription termination and poly-adenylation signals representing sequences 1533 to 2157 of this gene (Seeburg, 1982). There is an Alu middle repetitive DNA sequence in this fragment. Finally, the SV40 origin of replication and early region promoter-enhancer derived from the pcD-X plasmid (HindIII to PstI fragment) described in (Okayama et al., 1983). The promoter in this fragment is oriented such that transcription proceeds away from the CMV/hGH expression cassette.

The pCMV plasmids are distinguishable from each other by differences in the polylinker region and by the presence or absence of the translation enhancer. The starting pCMV1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from the CMV promoter was added C. The sequence acts as a translational enhancer by decreasing the requirements for initiation factors in polypeptide synthesis (Jobling et al., 1987; Browning et al., 1988). To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, $G_s$ alpha polypeptide, polypeptide phosphatase, synaptophysin, synapsin, insulin receptor, influenza hemagglutinin, androgen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites in pCMV that can cause spurious translation initiation. This codon should be avoided if possible in expression plasmids. A paper describing the construction and use of the parenteral pCMV1 and pCMV4 vectors has been published (Anderson et al., 1989b). cl V. Transfected Cells In yet another embodiment, the present invention provides recombinant host cells transformed or transfected with a polynucleotide that encodes a mu opioid receptor polypeptide or transcription regulatory polypeptide, as well as transgenic cells derived from those transformed or transfected cells. Preferably, recombinant host cells of the present invention are transfected with polynucleotide of SEQ ID NO: 1 or SEQ ID NO: 3 or SEQ ID NO: 7. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook, Fritsch and Maniatis, 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (Stratford-Perricaudet et al., 1992).

A transfected cell can be prokaryotic or eukaryotic. Preferably, the host cells of the invention are eukaryotic host cells. More preferably, the recombinant host cells of the invention are COS cells. Where it is of interest to produce a human mu opioid receptor polypeptides, cultured mammalian or human cells are of particular interest.

In another aspect, the recombinant host cells of the present invention are prokaryotic host cells. Preferably, the recombinant host cells of the invention are bacterial cells of the DH5α strain of *Escherichia coli*. In general, prokaryotes are preferred for the initial cloning of DNA sequences and constructing the vectors useful in the invention. For example, *E. coli* K12 strains can be particularly useful. Other microbial strains which can be used include *E. coli* B, and *E. coli* X1776 (ATCC No. 31537). These examples are, of course, intended to be illustrative rather than limiting.

Prokaryotes can also be used for expression. The aforementioned strains, as well as *E. coli* W3110 (F-, lambda-, prototrophic, ATCC No. 273325), bacilli such as *Bacillus subtilis*, or other enterobacteriaceae such as *Salmonella typhimurium* or *Serratus marcescens*, and various Pseudomonas species can be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang et al., 1978; Itakura et al., 1977; Goeddel et al., 1979; Goeddel et al., 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to introduce functional promoters into plasmid vectors (Siebwenlist et al., 1980).

In addition to prokaryotes, eukaryotic microbes, such as yeast can also be used. *Saccharomyces cerevisiae* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoter sequences in yeast vectors include the promoters for 3-phosphoglycerate kinase (Hitzeman et al., 1980) or other glycolytic enzymes (Hess et al., 1968; Holland et al., 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-1, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication can be provided with by construction of the vector to include an exogenous origin, such as can be derived from SV40 or other viral (e.g., Polyoma, Adeno, VSV, BPV, CMV) source, or can be provided by the host cell chromosomal replication mechanism. If the vector is integrated into the host cell chromosome, the latter is often sufficient.

VI. Preparing a Recombinant Mu Opioid Receptor Polypeptide or Transcription Regulatory Polypeptide In yet another embodiment, the present invention contemplates a process of preparing a mu opioid receptor polypeptide comprising transfecting cells with a polynucleotide that encodes a mu opioid receptor polypeptide to produce transformed host cells; and maintaining the transformed host cells under biological conditions sufficient for expression of the polypeptide. Preferably, the transformed host cells are eukaryotic cells. More preferably still, the eukaryotic cells are COS cells. Alternatively, the host cells are prokaryotic cells. More preferably, the prokaryotic cells are bacterial cells of the DH5α strain of *Escherichia coli*. Even more preferably, the polynucleotide transfected into the transformed cells comprise the nucleotide base sequence of SEQ ID NO: 1, SEQ ID NO: 3, SEQ ID NO: 7 or SEQ ID NO: 16. Most preferably, transfection is accomplished using a hereinbefore disclosed expression vector.

In yet another embodiment, the present invention contemplates a process of preparing a gene transcript comprising transfecting cells with a polynucleotide that encodes a gene transcription regulatory polypeptide to produce transformed host cells; and maintaining the transformed host cells under biological conditions sufficient for expression of the polypeptide. Preferably, the transformed host cells are eukaryotic cells. More preferably still, the eukaryotic cells are COS cells. Alternatively, the host cells are prokaryotic cells. More preferably, the prokaryotic cells are bacterial cells of the DH5α strain of *Escherichia coli*. Even more preferably, the polynucleotide transfected into the transformed cells comprise the nucleotide base sequence of SEQ ID NO: 3. Most preferably transfection is accomplished using a hereinbefore disclosed expression vector.

A host cell used in the process is capable of expressing a functional, recombinant mu opioid receptor polypeptide. A preferred host cell is a Chinese hamster ovary cell. However, a variety of cells are amenable to a process of the invention, for instance, yeasts cells, human cell lines, and other eukaryotic cell lines known well to those of the art.

Following transfection, the cell is maintained under culture conditions for a period of time sufficient for expression of a mu opioid receptor polypeptide. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C., more preferably from about 30° C. to about 40° C. and, even more preferably about 37° C.

pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well known in the art.

Transfected cells are maintained for a period of time sufficient for expression of a mu opioid receptor polypeptide. A suitable time depends inter alia upon the cell type used and is readily determinable by a skilled artisan. Typically, maintenance time is from about 2 to about 14 days.

A recombinant mu opioid receptor polypeptide or gene transcription regulatory polypeptide is recovered or collected either from the transfected cells or the medium in which those cells are cultured. Recovery comprises isolating and purifying the recombinant polypeptide. Isolation and purification techniques for polypeptides are well known in the art and include such procedures as precipitation, filtration, chromatography, electrophoresis and the like.

VII. Antibodies

In still another embodiment, the present invention provides antibodies immunoreactive with a polypeptide of the present invention. Preferably, the antibodies of the invention are monoclonal antibodies. More preferably, the polypeptide comprises the amino acid residue sequence of SEQ ID NO: 2, SEQ ID NO: 4, SEQ ID NO: 8 or SEQ ID NO: 17. Means for preparing and characterizing antibodies are well known in the art (Harlow and Lane, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobenzoyl-N-hydroxysuccinimide ester, carbodiimide and bis-biazotized benzidine.

As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

Researchers at the University of Minnesota, using information on the mu opioid receptor sequence of the present invention, have generated polyclonal antibodies immunoreactive with a mu opioid receptor polypeptide by synthesizing a 15-amino acid peptide corresponding to the mu opioid receptor C terminal end (peptide sequence: NHQLENLEAETAPLP); conjugating with glutaraldehyde to a carrier protein; immunizing rabbits; and collecting serum from immunized animals. It is well known in the art that variations in a polypeptide occur as a result of sequence polymorphisms in the polynucleotide encoding the polypeptide. For example, polynucleotide polymorphisms due to differences among individual members of the same species or between different species may exist, and such polymorphisms may result in variations in the polypeptide encoded by the polynucleotide. Also, polynucleotide variations due to alternative splicing may exist, and such variations may result in corresponding variations in the polypeptide encoded by the polynucleotide. Considering these situations, the present invention contemplates an embodiment for generating multiple antibodies based on sequence variations and polymorphisms. Such antibodies may be used to detect various forms of the polypeptide.

In another aspect, the present invention contemplates a process of producing an antibody immunoreactive with a mu opioid receptor polypeptide comprising the steps of (a) transfecting recombinant host cells with polynucleotide that encodes a mu opioid receptor polypeptide; (b) culturing the host cells under conditions sufficient for expression of the polypeptide; (c) recovering the polypeptide; and (d) preparing the antibodies to the polypeptide. Preferably, the host cell is transfected with the polynucleotide of SEQ ID NO: 1, SEQ ID NO: 3, SEQ ID NO: 7 or SEQ ID NO: 16. Even more preferably, the present invention provides antibodies prepared according to the process described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microliter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 $\mu$g of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immuno-specific reaction with the bound antibody. The polypeptide or polynucleotide is then easily removed from the substrate and purified.

VIII. Pharmaceutical Compositions

In a preferred embodiment, the present invention provides pharmaceutical compositions comprising a mu opioid receptor polypeptide or a gene transcription regulatory polypeptide and a physiologically acceptable carrier. More preferably, a pharmaceutical composition comprises a mu opioid receptor polypeptide having the amino acid residue sequence of SEQ ID NO: 2, SEQ ID NO: 4, SEQ ID NO: 8 or SEQ ID NO: 17. Even more preferably, a pharmaceutical composition of the invention comprises a polynucleotide that encodes a mu opioid receptor polypeptide and a physiologically acceptable carrier. Still more preferably, a pharmaceutical composition of the present invention comprises the amino acid residue sequence of SEQ ID NO: 2, SEQ ID NO: 4, SEQ ID NO: 8 or SEQ ID NO: 17. Alternatively, a pharmaceutical composition comprises the nucleotide sequence of SEQ ID NO: 1, SEQ ID NO: 3, SEQ ID NO: 7 or SEQ ID NO: 16.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art (Gabizon, et al., 1990; Ferruti, et al., 1986; Ranade 1989).

A transfected cell can also serve as a carrier. By way of example, a liver cell can be removed from an organism, transfected with a polynucleotide of the present invention using methods set forth above and then the transfected cell returned to the organism (e.g. injected intravascularly).

IX. A Process of Detecting Polynucleotide and the Polypeptides Encoded

Alternatively, the present invention provides a process of detecting a polypeptide of the present invention, wherein the process comprises immunoreacting the polypeptide with antibodies prepared according to a process described above to form an antibody-polypeptide conjugate and detecting the conjugates.

In yet another embodiment, the present invention contemplates a process of detecting a messenger RNA transcript that encodes a mu opioid receptor polypeptide or a gene transcription regulatory polypeptide, wherein the process comprises (a) hybridizing the messenger RNA transcript with a polynucleotide sequence that encodes the polypeptide to form a duplex; and (b) detecting the duplex. Alternatively, the present invention provides a process of detecting a DNA molecule that encodes a mu opioid receptor polypeptide, wherein the process comprises (a) hybridizing DNA molecules with a polynucleotide that encodes a mu opioid receptor polypeptide to form a duplex; and (b) detecting the duplex.

X. Screening Assays

In yet another aspect, the present invention contemplates a process of screening substances for their ability to interact with a mu opioid receptor polypeptide or a gene transcription regulatory polypeptide, the process comprising the steps of providing a polypeptide of the present invention and testing the ability of selected substances to interact with that polypeptide.

Utilizing the methods and compositions of the present invention, screening assays for the testing of candidate substances such as agonists and antagonists of mu opioid receptors can be derived. A candidate substance is a substance which can interact with or modulate, by binding or other intramolecular interaction, a mu opioid receptor polypeptide or a gene transcription regulatory polypeptide. In some instances, such a candidate substance is an agonist of the receptor and in other instances can exhibit antagonistic attributes when interacting with the receptor polypeptide. In other instances, such substances have mixed agonistic and antagonistic properties or can modulate the receptor in other ways. Alternatively, such substances can promote or inhibit transcription of a mu opioid receptor.

Recombinant receptor expression systems of the present invention possess definite advantages over tissue-based systems. The methods of the present invention make it possible to produce large quantities of mu opioid receptors for use in screening assays. More important, however, is the relative purity of the receptor polypeptides provided by the present invention. A relatively pure polypeptide preparation for assaying a protein-protein interaction makes it possible to use elutive methods without invoking competing, and unwanted, side-reactions.

Cloned expression systems such as those of the present invention are also useful where there is difficulty in obtaining tissue that satisfactorily expresses a particular receptor. Cost is another very real advantage, at least with regard to the microbial expression systems of the present invention. For antagonists in a primary screen, microorganism expression systems of the present invention are inexpensive in comparison to prior art tissue-screening methods.

Traditionally, screening assays employed the use of crude receptor preparations. Typically, animal tissue slices thought to be rich in the receptor of interest were the source of the receptor. Alternatively, investigators homogenized the tissue and used the crude homogenate as a receptor source. A major difficulty with this approach is that there are no tissue types where only one receptor type is expressed. The data obtained therefore could not be definitively correlated with a particular receptor. With the recent cloning of receptor sub-types and sub-sub-types, this difficulty is highlighted. A second fundamental difficulty with the traditional approach is the unavailability of human tissue for screening potential drugs. The traditional approach almost invariably utilized animal receptors. With the cloning of human receptors, there is a need for screening assays which utilize human receptors.

With the availability of cloned receptors, recombinant receptor screening systems have several advantages over tissue based systems. A major advantage is that the investigator can now control the type of receptor that is utilized in a screening assay. Specific receptor sub-types and sub-sub-types can be preferentially expressed and its interaction with a ligand can be identified. Other advantages include the availability of large amounts of receptor, the availability of rare receptors previously unavailable in tissue samples, and the lack of expenses associated with the maintenance of live animals.

Screening assays of the present invention generally involve determining the ability of a candidate substance to bind to the receptor and to affect the activity of the receptor, such as the screening of candidate substances to identify those that inhibit or otherwise modify the receptor's function. Typically, this method includes preparing recombinant receptor polypeptide, followed by testing the recombinant polypeptide or cells expressing the polypeptide with a candidate substance to determine the ability of the substance to affect its physiological function. In preferred embodiments, the invention relates to the screening of candidate substances to identify those that affect the enzymatic activity of the human receptor, and thus can be suitable for use in humans.

As is well known in the art, a screening assay provides a receptor under conditions suitable for the binding of an agent to the receptor. These conditions include but are not limited to pH, temperature, tonicity, the presence of relevant co-factors, and relevant modifications to the polypeptide such as glycosylation, palmytoilation, or prenylation. It is contemplated that the receptor can be expressed and utilized in a prokaryotic or eukaryotic cell. The host cell expressing the receptor can be used whole or the receptor can be isolated from the host cell. The receptor can be membrane bound in the membrane of the host cell or it can be free in the cytosol of the host cell. The host cell can also be fractionated into sub-cellular fractions where the receptor can be found. For example, cells expressing the receptor can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of co-factors can be required for the proper functioning of the receptor. Typical co-factors include sodium, potassium, calcium, magnesium, and chloride. In addition, small, non-peptide molecules, known as prosthetic groups can be required. Other biological conditions needed for receptor function are well known in the art.

It is well known in the art that proteins can be reconstituted in artificial membranes, vesicles or liposomes. (Danboldt et al., 1990). The present invention contemplates that the receptor can be incorporated into artificial membranes, vesicles or liposomes. The reconstituted receptor can be utilized in screening assays.

It is further contemplated that the receptor of the present invention can be coupled to a solid support. The solid support can be agarose beads, polyacrylamide beads, polyacrylic beads or other solid matrices capable of being coupled to proteins. Well known coupling agents include cyanogen bromide, carbonyldiimidazole, tosyl chloride, and glutaraldehyde.

It is further contemplated that secondary polypeptides which can function in conjunction with the receptor of the present invention can be provided. For example, the receptor of the present invention exerts its physiological effects in conjunction with a G-protein and an effector polypeptide.

In a typical screening assay for identifying candidate substances, one employs the same recombinant expression host as the starting source for obtaining the receptor polypeptide, generally prepared in the form of a crude homogenate. Recombinant cells expressing the receptor are washed and homogenized to prepare a crude polypeptide homogenate in a desirable buffer such as disclosed herein. In a typical assay, an amount of polypeptide from the cell homogenate, is placed into a small volume of an appropriate assay buffer at an appropriate pH. Candidate substances, such as agonists and antagonists, are added to the admixture in convenient concentrations and the interaction between the candidate substance and the receptor polypeptide is monitored.

Where one uses an appropriate known substrate for the receptor, one can, in the foregoing manner, obtain a baseline activity for the recombinantly produced receptor. Then, to test for inhibitors or modifiers of the receptor function, one can incorporate into the admixture a candidate substance whose effect on the receptor is unknown. By comparing reactions which are carried out in the presence or absence of the candidate substance, one can then obtain information regarding the effect of the candidate substance on the normal function of the receptor.

Accordingly, it is proposed that this aspect of the present invention provides those of skill in the art with methodology that allows for the identification of candidate substances having the ability to modify the action of opioid receptor polypeptides in one or more manners.

In one embodiment, such an assay is designed to be capable of discriminating those candidate substances with the desirable properties of opioids but which lack the undesirable properties of opioids. In another embodiment, screening assays for testing candidate substances such as agonists and antagonists of mu opioid receptors are used to identify such candidate substances having selective ability to interact with one or more of the opioid receptor polypeptides but which polypeptides are without a substantially overlapping activity with other opioid receptors.

Additionally, screening assays for the testing of candidate substances are designed to allow the investigation of structure activity relationships of opioids with the mu receptors, e.g., study of binding of naturally occurring hormones or other substances capable of interacting or otherwise modulating with the mu receptor versus studies of the activity caused by the binding of such molecules to the mu receptor. In certain embodiments, the polypeptides of the invention are crystallized in order to carry out x-ray crystallographic studies as a means of evaluating interactions with candidate substances or other molecules with the opioid receptor polypeptide. For instance, the purified recombinant polypeptides of the invention, when crystallized in a suitable form, are amenable to detection of intra-molecular interactions by x-ray crystallography.

An important aspect of the invention is the use of recombinantly produced mu opioid receptor polypeptide in screening assays for the identification of substances which can inhibit or otherwise modify or alter the function of the receptor. The use of recombinantly produced receptor is of particular benefit because the naturally occurring receptor is present in only small quantities and has proven difficult to purify. Moreover, this provides a ready source of receptor, which has heretofore been unavailable.

As described above, receptors in the presence of agonists can exert their physiological effects through a secondary molecule. A screening assay of the invention, in preferred embodiments, conveniently employs a mu opioid receptor polypeptide directly from the recombinant host in which it is produced. This is achieved most preferably by simply expressing the selected polypeptide within the recombinant host, typically a eukaryotic host, followed by preparing a crude homogenate which includes the polypeptide. A portion of the crude homogenate is then admixed with an appropriate effector of the mu receptor along with the candidate substance to be tested. By comparing the binding of the selected effector to the receptor in the presence or absence of the candidate substance, one can obtain information regarding the physiological properties of the candidate substance.

The receptor can be expressed in a prokaryotic or a eukaryotic cell. Receptors have been expressed in E. coli (Bertin et al., 1992), in yeast (King et al., 1990) and in mammalian cells (Bouvier et al., 1988).

A cell expressing a receptor can be used whole to screen agents. For example, cells expressing the receptor of the present invention can be exposed to radiolabeled agent and the amount of binding of the radiolabeled agent to the cell can be determined.

The cell expressing the receptor can be fractionated into sub-cellular components which contain the receptor of the present invention. Methods for purifying sub-cellular fractions are well known in the art. Sub-cellular fractions include but are not limited to the cytoplasm, cellular membrane, other membranous fractions such as the endoplasmic reticulum, golgi bodies, vesicles and the nucleus. Receptors isolated as sub-cellular fractions can be associated with cellular membranes. For example, if cellular membrane vesicles are isolated from the cell expressing the receptor, the receptor molecule can be membrane bound. It is further contemplated that the receptor of the present invention can be purified from a cell that expresses the receptor. Methods of purification are well known in the art. The purified receptor can be used in screening assays.

In that most such screening assays in accordance with the invention are designed to identify agents useful in mimicking the desirable aspects of opioids while eliminating the undesirable aspects of the hormone, preferred assays employ opioids as the normal agonist.

There are believed to be a wide variety of embodiments that can be employed to determine the effect of the candidate substance on a mu receptor polypeptide of the invention, and the invention is not intended to be limited to any one such method. However, it is generally desirable to employ a system wherein one can measure the ability of the receptor polypeptide to bind to and or be modified by the effector employed in the presence of a particular substance.

The detection of an interaction between an agent and a receptor can be accomplished through techniques well known in the art. These techniques include but are not limited to centrifugation, chromatography, electrophoresis and spectroscopy. The use of isotopically labelled reagents in conjunction with these techniques or alone is also contemplated. Commonly used radioactive isotopes include $^3$H, $^{14}$C, $^{22}$Na, $^{32}$P, $^{35}$S, $^{45}$Ca, $^{60}$Co, $^{125}$I, and $^{131}$I. Commonly used stable isotopes include $^2$H, $^{13}$C, $^{15}$N, $^{18}$O.

For example, if an agent can bind to the receptor of the present invention, the binding can be detected by using radiolabeled agent or radiolabeled receptor. Briefly, if radiolabeled agent or radiolabeled receptor is utilized, the agent-receptor complex can be detected by liquid scintillation or by exposure to X-Ray film.

The interaction of an agent and a receptor can also be detected by the use of atomic force microscopy (AFM). Three dimensional images of biological materials (e.g. proteins, nucleic acids and membranes) under physiological conditions can be obtained with nanometer resolution through AFM. AFM has been used to image a number of biological specimens. (Edstrom et al., 1990; Drake et al., 1989; Butt et al., 1990; Hoh et al., 1991; Weisenhorn et al., 1990; Henderson et al., 1992; Hansma et al., 1992; Durbin and Carlson, 1992; Lal et al., 1993).

AFM operates by measuring the atomic force between the tip of an AFM probe and the top surface of the sample being imaged. The probe used for AFM is an integral part of a micro-fabricated cantilever, often made of $Si_3N_4$. AFM senses height of the sample surface and controls the vertical position of the sample by tracking the deflection of the cantilever. The position of the cantilever is monitored via laser beam reflection off the cantilever to an optical position sensor. The signal is used in a feedback mechanism to control the height of the sample. This feedback mechanism allows the AFM to scan over the sample surface at a constant deflection, hence a constant force. Because the atomic force is a function of inter-atomic distance, the height position of the probe represents the sample surface contour. The vertical features of the sample are thus recorded as the probe is moved over the surface in a horizontal raster scan, and the image of the sample surface can be displayed in real time during imaging and analyzed at a later time.

Recently, the cloned nicotinic acetylcholine receptor expressed in Xenopus oocytes was imaged by AFM by the present inventor (Lal and Yu, 1993). The AFM image revealed that the acetylcholine receptor was roughly 13 nm, traversing the lipid bilayer and protruding a few nanometers out of the plasma membrane and into the cytoplasm. The AFM image also showed that the acetylcholine receptors clustered together in the lipid bilayer. The average distance between individual receptors in Xenopus oocytes was roughly 9–11 nm.

The interaction of an agonist or an antagonist with a mu opioid receptor can be imaged by AFM. The characterization of intermolecular arrangements and interactions, such as ligand-receptor, antibody-receptor, antibody-transcription regulatory peptide can be achieved by AFM.

When an agent modifies the receptor, the modified receptor can also be detected by differences in mobility between the modified receptor and the unmodified receptor through the use of chromatography, electrophoresis or centrifugation. When the technique utilized is centrifugation, differences in mobility are known as the sedimentation coefficient. The modification can also be detected by differences between the spectroscopic properties of the modified and unmodified receptor. As a specific example, if an agent covalently modifies a receptor, the difference in retention times between modified and unmodified receptor on a high pressure liquid chromatography (HPLC) column can easily be detected.

As a specific example, where an agent covalently modifies a receptor, the spectroscopic differences between modified and unmodified receptor in the nuclear magnetic resonance (NMR) spectra can be detected. Alternatively, one can focus on the agent and detect the differences in the spectroscopic properties or the difference in mobility between the free agent and the agent after modification of the receptor.

Where a secondary polypeptide is provided, the agent-receptor-secondary polypeptide complex or the receptor-secondary polypeptide complex can be detected. Differences in mobility or differences in spectroscopic properties as described above can be detected.

It is further contemplated that where a secondary polypeptide is provided the enzymatic activity of the effector polypeptide can be detected. For example, many receptors exert physiological effects through the stimulation or inhibition of adenylyl cyclase. The enzymatic activity of adenylyl cyclase in the presence of an agent can be detected.

The interaction of an agent and a receptor can be detected by providing a reporter gene. Well known reporter genes include β-galactosidase (β-Gal), chloramphenicol transferase (CAT) and luciferase. The reporter gene is expressed by the host and the enzymatic reaction of the reporter gene product can be detected.

In preferred assays, an admixture containing the polypeptide, effector and candidate substance is allowed to incubate for a selected amount of time, and the resultant incubated mixture subjected to a separation means to separate the unbound effector remaining in the admixture from any effector/receptor complex so produced. Then, one simply measures the amount of each (e.g., versus a control to which no candidate substance has been added). This measurement can be made at various time points where velocity data is desired. From this, one can determine the ability of the candidate substance to alter or modify the function of the receptor.

Numerous techniques are known for separating the effector from effector/receptor complex, and all such methods are intended to fall within the scope of the invention. Use of thin layer chromatographic methods (TLC), HPLC, spectrophotometric, gas chromatographic/mass spectrophotometric or NMR analyses. It is contemplated that any such technique can be employed so long as it is capable of differentiating between the effector and complex, and can be used to determine enzymatic function such as by identifying or quantifying the substrate and product.

The effector/receptor complex itself can also be the subject of techniques such as x-ray crystallography. Where a candidate substance replaces the opioid molecule as the drug's mode of action, studies designed to monitor the replacement and its effect on the receptor will be of particular benefit.

A. Screening Assays for Mu Opioid Receptor Polypeptides.

The present invention provides a process of screening a biological sample for the presence of a mu opioid receptor polypeptide. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the mu opioid receptor polypeptide whose presence is being assayed. Typically, exposure is accomplished by forming an admixture in a liquid medium that contains both the antibody and the candidate opioid receptor polypeptide. Either the antibody or the sample with the opioid receptor polypeptide can be affixed to a solid support (e.g., a column or a microliter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 M solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the opioid receptor polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$ M, exposure time is from about 10 minutes to about 200 minutes.

The presence of mu opioid receptor polypeptide in the sample is detected by detecting the formation and presence of antibody-mu opioid receptor polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Means for affixing indicators to antibodies are well known in the art. Commercial kits are available.

B. Screening Assay for Anti-mu Opioid Receptor Antibody.

In another aspect, the present invention provides a process of screening a biological sample for the presence of antibodies immunoreactive with a mu opioid receptor polypeptide (i.e., an anti-mu opioid receptor antibody). In accordance with such a process, a biological sample is exposed to a mu opioid receptor polypeptide under biological conditions and for a period of time sufficient for antibody-polypeptide conjugate formation and the formed conjugates are detected.

C. Screening Assay for a Polynucleotide that Encodes a Mu Opioid Receptor Polypeptide.

A DNA molecule and, particularly a probe molecule, can be used for hybridizing as oligonucleotide probes to a DNA source suspected of possessing a mu opioid receptor polypeptide encoding polynucleotide or gene. The probing is usually accomplished by hybridizing the oligonucleotide to a DNA source suspected of possessing such a receptor gene. In some cases, the probes constitute only a single probe, and in others, the probes constitute a collection of probes based on a certain amino acid sequence or sequences of the opioid receptor polypeptide and account in their diversity for the redundancy inherent in the genetic code.

A suitable source of DNA for probing in this manner is capable of expressing mu opioid receptor polypeptides and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/ or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the opioid receptor family and related polypeptides from a DNA library potentially containing such sequences; (3) primers for hybridizing to related sequences for the purpose of amplifying those sequences; (4) primers for altering the native opioid receptor DNA sequences; as well as other techniques which rely on the similarity of the DNA sequences to those of the opioid receptor DNA segments herein disclosed.

As set forth above, in certain aspects, DNA sequence information provided by the invention allows for the preparation of relatively short DNA (or RNA) sequences (e.g., probes) that specifically hybridize to encoding sequences of the selected opioid receptor gene. In these aspects, nucleic acid probes of an appropriate length are prepared based on a consideration of the selected opioid receptor sequence (e.g., a sequence such as that shown in SEQ ID NOS: 1, 3, 7 or 16. The ability of such nucleic acid probes to specifically hybridize to mu opioid receptor encoding sequences lend them particular utility in a variety of embodiments. Most importantly, the probes can be used in a variety of assays for detecting the presence of complementary sequences in a given sample. However, uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of the mu opioid receptor encoding sequence, such as that shown in SEQ ID NOS. 1, 3, 7 or 16. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Of course, polynucleotide segments of 15, 20, 25, 30, 35, 40, 45, 50, 55, 60, 65, 70, 80, 90, 100, or more contiguous bases are also expected to be of use in the invention. Such fragments can be readily prepared by, for example, directly synthesizing the fragment by chemical means, by application of nucleic acid reproduction technology, such as the PCR technology of U.S. Pat. No. 4,603,102, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M NaCl at temperatures of 50° C. to 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate opioid receptor coding sequences from related species, functional equivalents, or the like, less stringent hybridization conditions are typically needed to allow formation of the heteroduplex. Under such circumstances, one employs conditions such as 0.15M–0.9M salt, at temperatures ranging from 20° C. to 70° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove non-specifically bound probe molecules, specific hybridization is detected, or even quantified, by means of the label.

D. Screening For Agonists and Antagonists

Mu receptors are one of the major subtypes of opioid receptors. Therefore, highly selective mu opioid receptor agonists are clinically useful.

Development of highly selective, clinically useful mu opioid receptor agonists is facilitated by understanding the specific sites within the mu receptor necessary for agonist binding. The recent cloning of the rodent mu opioid receptor cDNA has opened up the possibility to investigate the structural domains of this receptor subtype that are responsible for its functioning.

XI. Assay Kits

In another aspect, the present invention contemplates diagnostic assay kits for detecting the presence of mu opioid receptor polypeptides in biological samples, where the kits comprise a first container containing a first antibody capable of immunoreacting with mu opioid receptor polypeptides, with the first antibody present in an amount sufficient to perform at least one assay. Preferably, assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also contemplates a diagnostic kit for screening agents. Such a kit comprises a mu opioid receptor of the present invention. The kit can further contain reagents for detecting an interaction between an agent and a receptor of the present invention. The provided reagent can be radiolabeled. The kit can contain a known radiolabeled agent capable of binding or interacting with a receptor of the present invention.

It is further contemplated that the kit can contain a secondary polypeptide. The secondary polypeptide can be a G-protein. The secondary polypeptide can also be an effector protein. When a secondary polypeptide is included in a kit, reagents for detecting an interaction between the receptor and the secondary polypeptide can be provided. As a specific example, an antibody capable of detecting a receptor/G-protein complex can be provided. As another specific example, an antibody capable of detecting a G-protein/effector complex can be provided. Reagents for the detection of the effector can be provided. For example, if the effector provided is adenylyl cyclase, reagents for detecting the activity of adenylyl cyclase can be provided. The identity of such agents is within the knowledge of those skilled in the relevant art.

In an alternative aspect, the present invention provides diagnostic assay kits for detecting the presence, in biological samples, of a polynucleotide that encodes a mu opioid receptor polypeptides, the kits comprising a first container that contains a second polynucleotide identical or complementary to a segment of at least 10 contiguous nucleotide bases of SEQ ID NO: 1, SEQ ID NO: 3, SEQ ID NO: 7 or SEQ ID NO: 16.

In another embodiment, the present invention contemplates diagnostic assay kits for detecting the presence, in a biological sample, of antibodies immunoreactive with mu opioid receptor polypeptides, the kits comprising a first container containing a mu opioid receptor polypeptide that immunoreacts with the antibodies, with the polypeptides present in an amount sufficient to perform at least one assay. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

In another embodiment, the present invention contemplates diagnostic assay kits for determining genetic variation in mu opioid receptor gene, the kits comprising a first container for analyzing segments of the mu opioid receptor gene. Sequence information is compared to the known database such as that in a microcomputer or on a printed paper, and individual characteristics are noted. Such characteristics are then compared with medical database information regarding the predicted responsiveness of such an individual to a certain medical intervention such as administration of an opioid drug, and the prescribed dosage can be adjusted to suit the desired response profile of an individual with such a genetic content. This method may enable a genetic-based diagnosis approach in addition to, or instead of, traditional laboratory tests that do not determine an individual's genetic content.

EXAMPLES

Examples are included to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

Example I: Isolation of cDNA Clones

Low stringency hybridization was utilized for isolating opioid receptors related to the mouse δ-opioid receptor (Evan et al., 1992; Kieffer et al., 1992) because all three types of opioid receptors share sequence homology, share overlapping pharmacology, couple to G proteins, and have a common effect on $Ca^{2+}$ and $K^+$ channels (Pastrenak G. W. 1988). Oligodeoxynucleotides were synthesized based on the mouse δ-opioid receptor sequence (Evan et al., 1992; Kieffer et al., 1992) and were used to amplify, by PCR, a sequence fragment from a rat brain cDNA library (Snutch et al., 1990).

Two primers, ATCTTCACCCTCACCATGATG (SEQ ID NO: 5) and CGGTCCTTCTCCTTGGAACC (SEQ ID NO: 6), were synthesized from the sequence of the mouse δ-opioid receptor (Evans et al., 1992; Kieffer et al., 1992), corresponding to the third transmembrane domain and the third cytoplasmic loop, respectively. PCR was performed using purified DNA from a rat brain cDNA library (Snutch et al., 1990), in an air Thermo-cycler (Idaho Technology) under modified conditions (94° for 10 sec, 56° for 20 sec, and 72° for 40 sec, for 40 cycles). A 356 bp fragment was purified and subcloned into pBLUESCRIPT SK(+) vector. Sequence analysis of the resulting 356 bp PCR product revealed complete identity with the corresponding portion of the δ-opioid receptor (Evans et al., 1992), showing a conserved relationship between the δ-opioid receptors from these two species.

The 356-bp fragment was then used to screen a rat brain cDNA library under low stringency conditions (6×SSPE (1.08 M NaCl, 60 mM $NaH_2PO_4$, 6 mM EDTA, pH 7.4), 5×Denhardt solution, 0.5% sodium dodecyl sulfate, 100 μg/ml salmon sperm DNA, at 50°). The final wash was carried out in 0.5×standard saline citrate (7 mM NaCl, 7.5 mM sodium citrate), 0.1% sodium dodecyl sulfate, at 50°. Phagemids were rescued from positive λ clones by infection with helper phage. Two independent isolates were used for sequence determination by shotgun cloning into pBLUE-SCRIPT SK(+). Subsequent sequencing of both strands from each isolate showed these two clones to be identical. Potential post-translational modification sites were identified by using the PCGENE program. Comparison of the sequence with other receptors was performed by using the BLAST program (National Institutes of Health).

Figures 1, 5A:
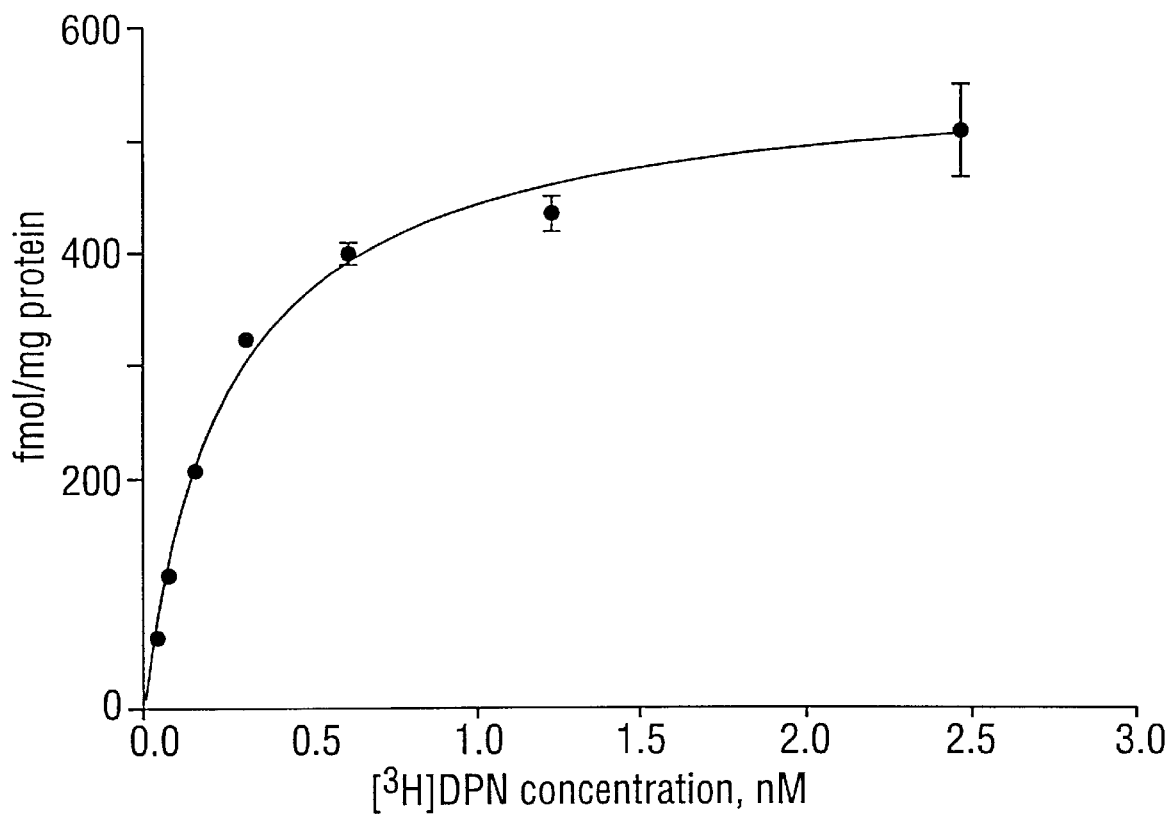
Figures 2, 5A:
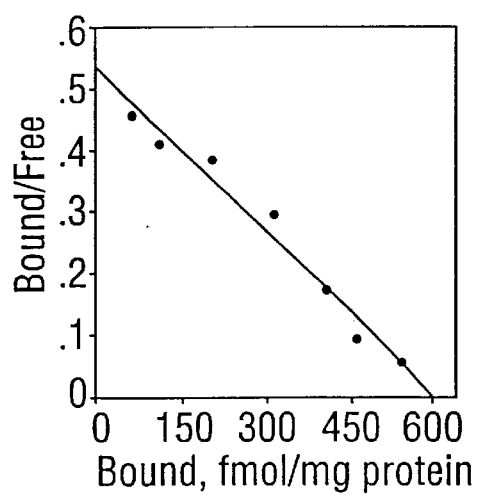

Sequence analysis revealed that one cDNA clone contained an open reading frame of 1194 bp, encoding a protein of 398 amino acids. Hydropathy analysis of the deduced protein indicated seven hydrophobic domains, typical of G protein-coupled receptors (Collins et al., 1991). This protein, termed MOR-1, SEQ ID NO: 1, shows high levels of homology with the mouse δ-opioid receptor DOR-1 (Evans et al., 1992) (64%) and rat somatostatin receptors (Meyerhof et al., 1991; Kluxen et al., 1992) (44%). MOR-1 also displays moderate homology (30–32%) with several G protein-coupled receptors, including the angiotensin II receptor, the interleukin-8 receptor, the N-formyl peptide receptor, and the C—C chemokine receptor. The sequence homology is lower (≧25%) between MOR-1 and other G protein-coupled receptors, such as the adrenergic and muscarinic receptors (Collins et al., 1991). At the amino acid sequence level, SEQ ID NO: 2, MOR-1 contains several sites that are conserved among other G protein-coupled receptors (Collins et al., 1991). Aspartic acid residues thought to interact with the protonated amine group of various ligands appear in putative transmembrane domains II and III, and two conserved cysteine residues believed to be involved in disulfide bonding occur in the first and second extracellular loop domains (Dixon et al., 1988). Both of these features are conserved between MOR-1 and the δ-opioid receptor (FIG. 1). In addition, MOR-1 displays a cysteine residue in the carboxyl-terminal region that is conserved among many G protein-coupled receptors which likely serves as a target for palmitoylation (Collins et al., 1991). There are also multiple sites in the second and third intracellular loops as well as the carboxyl-terminal region that can undergo phosphorylation via protein kinase A and protein kinase C. Compared with the mouse δ-opioid receptor, MOR-1 contains five instead of two asparagine residues in the amino-terminal region that match the consensus sequence for N-linked glycosylation. These glycosylation sites are important in the modulation of receptor expression and function (Sumikawa and Miledi, 1989).

Example II: Expression of Rat Mu-Opioid Receptor

A 1.4-kilobase HindIII fragment encompassing the open reading frame from the cDNA encoding MOR-1 was cloned downstream of the human cytomegalovirus promoter in the mammalian expression vector pRc/CMV (Invitrogen). COS-7 cells grown in Dulbecco's modified Eagle's medium (Sigma D-5648) supplemented with 10% fetal bovine serum and 2 mM glutamine were transfected with supercoiled DNA by either electroporation or $CaPO_4$ co-precipitation (Graham and Van Der Eb, 1973). Electroporation was performed in 0.4 cm cuvettes at 200 V, using $3\times10^6$ cells in a total volume of 0.5 ml containing growth medium, 40 μg of expression plasmid, and 200 μg of sheared salmon sperm DNA. Cells were harvested 48–72 hr after electroporation transfection.

The plasmid was transiently transfected into COS-7 cells to express MOR-1, and membranes from these cells were prepared. Cells were harvested by scraping into phosphate-buffered saline, pH 7.2, and centrifuged. Cell pellets were resuspended in lysis buffer (20 mM Tris-HCl, pH 7.4, 5 mM EDTA, 1 mM phenylmethylsulfonyl fluoride) and lysed with a Dounce homogenizer fitted with a tight pestle. The suspension was centrifuged for 10 min at 1000×g, and the supernatant was removed to a fresh tube. The pellet was resuspended in lysis buffer and centrifuged as described above. The supernatants were then combined and centrifuged for 20 min at 35,000×g. Membranes were washed in 50 mM Tris-HCl, PH 7.4, and centrifuged for 20 min at 35,000×g. The membrane pellets were then suspended in 50 mM Tris-HCl, PH 7.4. Protein concentrations were determined by the method of Bradford (Bradford, 1976).

Binding studies of membrane aliquots (15–50 μg/reaction) from the transfected COS-7 cells were carried out in 50 mM Tris-HCl, pH 7.4, 0.2% bovine serum albumin, at 4° for 90 min. A range of 0.01–2.5 nM [$^3$H] diprenorphine was used in the saturation assay and 0.25 nM was used for the displacement experiment. The reactions were terminated by vacuum filtration through Whatman GF/B filters which were pretreated with 1% polyethylenimine. Nonspecific binding was determined using 5 μM naloxone.

Saturation binding of membranes was performed using [$^3$H]diprenorphine (Magnan et al., 1982), a nonselective opioid antagonist with high affinity for all three types of opioid receptors (FIG. 1). Membranes of COS cells transfected with the MOR-1 plasmid displayed [$^3$H] diprenorphine binding with a dissociation constant ($K_d$) value of 0.3±0.09 nM (mean±standard error, five experiments). This is one tenth the $K_d$ value (3.8 nm) reported for the cloned mouse δ-opioid receptor (Evans et al., 1992).

Various ligands which displace [$^3$H]diprenorphine binding were used to characterize the pharmacological features of MOR-1. The inhibition constant $K_i$ values were obtained from three binding experiments for each ligand and are listed in Table 2.

The μ-selective agonist [D-Ala$^2$, N-Me-Phe$^4$, Gly-ol$^5$]-enkephalin (DAGO) displaced diprenorphine binding with high affinity ($K_i$=2.8 nM), whereas the δ-selective agonist [D-Pen$^{2,5}$]-enkephalin (DPDPE) and the κ-selective agonist U-50488 showed low affinities, with $K_i$ values in the micromolar range (Pasternak et al., 1980). [D-Ala$^2$, D-Leu$^5$]-enkephalin (DADLE) and [D-Ser$^2$, Leu$^5$, Thr$^6$]-enkephalin (DSLET), two predominantly δ agonists that have previously been shown to interact with μ receptors (Barrett and Vaught, 1983; Itzhak and Pasternak, 1987), showed binding to MOR-1 with moderate affinities ($K_i$=55 and 314 nM, respectively). The rank order of potency for these opioid agonists is DAGO>DADLE>DSLET>U-50488>DPDPE which is the pharmacological profile of μ receptors. Displacement of diprenorphine binding to MOR-1 was performed with three μ-selective antagonists, β-FNA, naloxonazine, and cyprodime (Ward et al., 1985; Nishimura et al., 1984; Curciani et al., 1987; Schmidhammer et al., 1990). All three ligands exhibited high potency in displacing diprenorphine binding to MOR-1 with $K_i$ values in the nanomolar range (Table 1). The order of potency for opioid agonists and the nanomolar affinity for μ-selective antagonists indicates that MOR-1 is a μ-opioid receptor.

TABLE 2

| Ligand | $K_i$ values (nM) |
| --- | --- |
| Agonists | |
| (DAGO) (DAMGO) | 2.8 ± 0.2 |
| (DADLE) | 55 ± 17 |
| (DSLET) | 314 ± 35 |
| U-50488 | 1,551 ± 307 |
| (DPDPE) | 7,297 ± 1,092 |
| Antagonists and Somatostatins | |
| Naloxone | 1.0 ± 0.6 |
| β-funaltrexamine (β-FNA) | 1.3 ± 0.1 |
| Naloxonazine | 2.4 ± 0.9 |
| Cyprodime | 9.1 ± 2.8 |
| Cyclic somatostatin | 10,944 ± 6,777 (IC$_{50}$) |
| Somatostatin-1-14 | 730,000 (IC$_{50}$) |

Figure 2A:
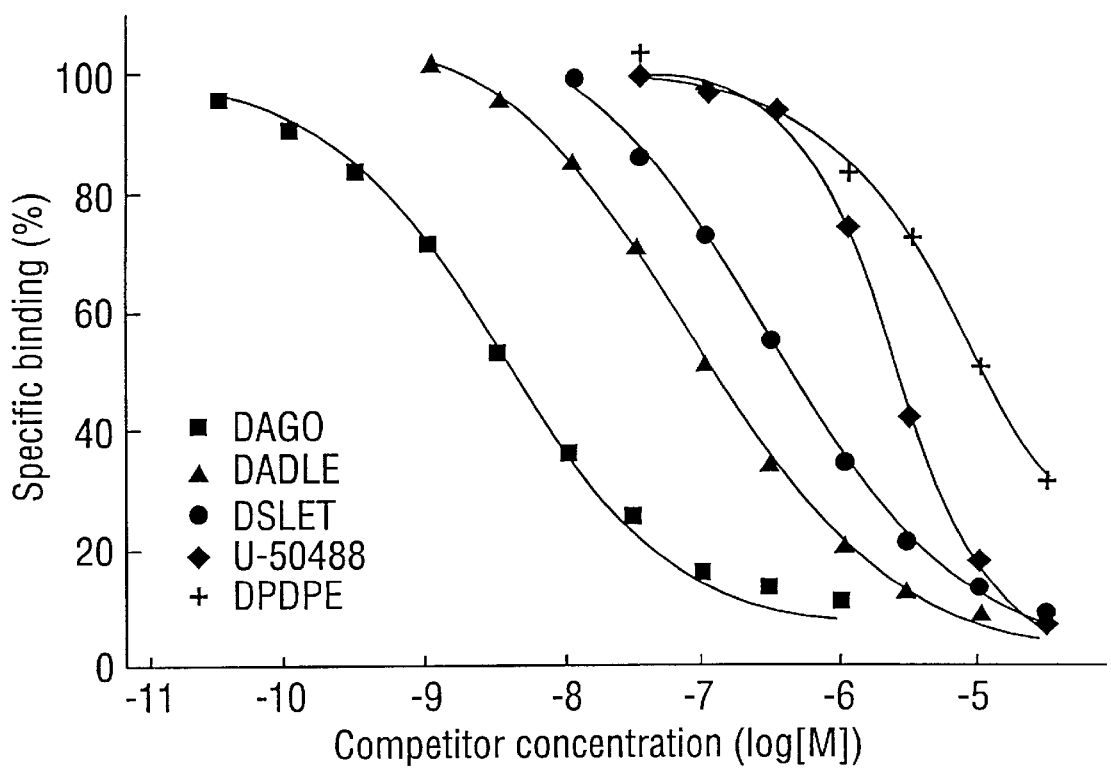
FIG. 2. Panels A and B of FIG. 2 show displacement of [$^3$H]Diprenorphine Binding with Unlabeled Ligands as Competitors Data from a representative experiment are presented for each ligand. A, using opioid agonists as competitors; B, using opioid antagonists and somatostatins as competitors.
Figure 2B:
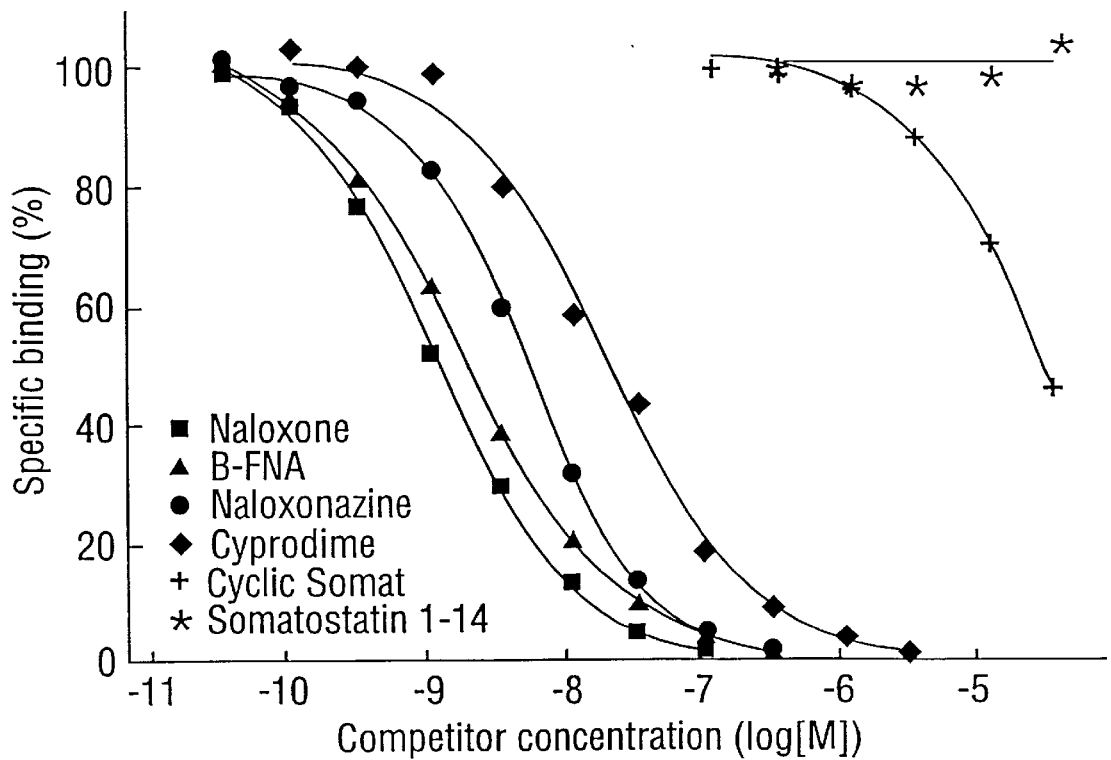

The sequence homology between rat μ-opioid receptor encoded by MOR-1 cDNA and the somatostatin receptors is noteworthy. Many somatostatin analogues, especially those of the cyclic form, have been shown to interact with μ-opioid receptors, and some of them have been used as μ-selective antagonists (Gulya et al., 1986). Displacement binding experiments were performed using two somatostatin ligands, somatostatin-1-14 and cyclic somatostatin. Somatostatin-1-14 did not displace [$^3$H]diprenorphine binding to the rat μ receptor encoded by the MOR-1 cDNA, at concentrations as high as 30 μM, whereas cyclic somatostatin competed with diprenorphine binding with an IC$_{50}$ value in the micromolar range (FIGS. 2A and 2B; Table 1).

Figure 3:
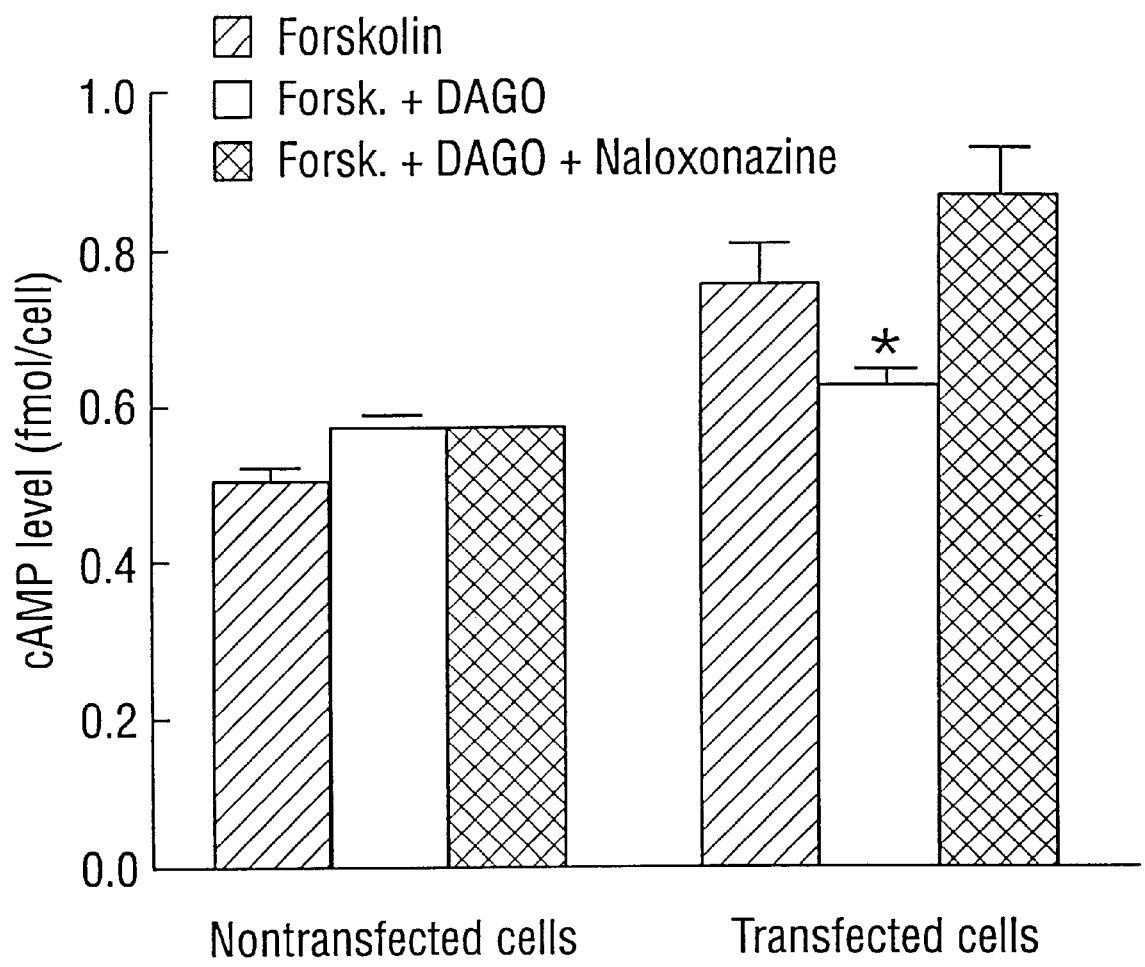
FIG. 3. Functional Coupling of MOR-1 to Adenylyl Cyclase Parental COS-7 cells (Nontransfected cells) or COS-7 cells expressing MOR-1 (Transfected cells) were stimulated with forskolin (Forsk.) to elevate adenylyl cyclase activity above basal levels. The $\mu$-selective ligands were included during forskolin treatment as indicated. Cellular cAMP levels were determined. Data are expressed as mean±standard error (four experiments). *, Data are significantly different from the control group (transfected cells treated with forskolin only).

All three classes of opioid receptors are coupled to adenylyl cyclase (Childers, 1993; Cox, 1993; Sharma et al., 1975). cAMP levels were determined in COS-7 cells after exposure to μ-selective ligands to examine whether the μ receptor is coupled to intracellular signaling pathways. COS-7 cells transiently expressing the MOR-1 plasmid cDNA were harvested 48 hrs after transfection and were resuspended in growth medium. Cells were treated with 10 μM forskolin in the presence of 1 mM 3-isobutyl-1-methylxanthine at 37° for 10 min. DAGO (100 nM) and naloxonazine (10 μM) were included during forskolin treatment where indicated. Cells were pelleted and then solubilized in 0.1 N HCl. After extraction with water-saturated ether, the supernatants were lyophilized. cAMP was assayed using a commercially available radioimmunoassay kit (DuPont/NEN). Results are shown in FIG. 3. In nontransfected COS-7 cells, treatment with these ligands did not cause significant changes in the intracellular cAMP levels. In transfected cells expressing the μ receptor, the μ-specific agonist DAGO reduced cAMP levels significantly (18.1±2.5% reduction from control, p<0.05). This inhibitory effect on adenylyl cyclase activity by DAGO was blocked by the μ-selective antagonist naloxonazine. It has been reported that μ-opioid receptors exert an inhibitory effect on adenylyl cyclase activity (Frey and Kebabian, 1984) and that activation of μ receptors in a human neuroblastoma cell line reduces intracellular cAMP levels by approximately 20% (Yu et al., 1986). These data are consistent with these reports and shows that the μ-opioid receptor encoded by MOR-1 is functionally coupled to the inhibition of adenylyl cyclase.

Example III: Stable Transfection of Mammalian Cells

Stably transfected cultured mammalian cells were generated by transfecting chinese hamster ovary cells (CHO) with the vector pRc/CMV which contained a cDNA coding for a mu opioid receptor. CHO cells from the American Type Culture Collection were plated at a density of 5×10$^4$ cells/100 mm plate one day before transfection. The CHO cells were incubated at 37° C. in a humidified chamber with 5% $CO_2$, in DME (Sigma), supplemented with 2 mM glutamine and 10% fetal bovine serum. The culture medium was changed 4–6 hours before transfection. The plasmid DNA was transfected into cells using the calcium phosphate precipitation method (Graham and Van Der Eb, 1973). After the $CaPO_4$ precipitation, the plates were incubated in a 3% $CO_2$, humidified chamber at 37° C. After 15–24 hr at 3% $CO_2$, the cells were washed with Hank's balanced salt solution, fresh culture medium was added, and the cells were transferred to a 5% $CO_2$, humidified incubator at 37° C. After 24 hr at 5% $CO_2$, selection for neomycin resistance was initiated by replacing the culture medium with medium containing 500 μg/ml of G418 (Sigma). G418 is a neomycin analogue that is permeable to mammalian cell membranes. The selection medium was changed every 2–3 days until drug-resistant colonies formed (2–3 weeks). Individual colonies were picked and replated after trypsin dissociation. A second round of selection was performed to isolate clonal derivatives. G418 resistant colonies were then allowed to grow in G418 medium until the plates were confluent. Aliquots of cells G418 resistant cells were frozen in liquid nitrogen for long-term storage of the transfected cells.

The expression of the mu opioid receptor in stably transfected CHO cells was demonstrated by saturation binding studies using a range of 0.2–20 mM $^3$H-DAGO. Membranes from G418 resistant CHO cells were prepared as described in Example II above. The $B_{MAX}$ of $^3$H-DAGO binding to membranes from stably transfected CHO cells was 660 nmole/mg protein, and the $K_D$ is ~1 nM for $^3$H-DAGO. These values are comparable to the values obtained for $^3$H-DAGO binding to mu opioid receptors obtained from transient transfections of COS-7 cells.

As expected for stable transfectants, different clonal derivatives gave different levels of receptor expression. For example, clones #15 and #18 had 1 and 3 picomoles of the receptor per milligrams of membrane protein, respectively as determined by ligand binding.

Functional characteristics of the expressed mu opioid receptor in stable transfection were also determined by assaying the GTPase activity of G proteins (Koshi and Klee, 1981). Upon stimulation by 10 μM DAMGO, the GTPase activity was increased by 30%, indicating that the G proteins were activated by the mu opioid receptor. This effect of DAMGO was blocked by naloxone.

Example IV: Human Mu Opioid Receptor: Augmentation of Functional Desensitization by Both Calcium/Calmodulin-Dependent Protein Kinase and Protein Kinase C The inventor has isolated a cDNA for the human μ opioid receptor. This cDNA contains an open reading frame capable of encoding a protein of 400 amino acids with 94% sequence similarity to the rat μ opioid receptor. Transient expression of this cDNA in COS-7 cells produced high affinity binding to μ-selective agonists and antagonists, providing evidence that the protein encoded by this cDNA has the pharmacological profile of a μ opioid receptor. This receptor demonstrated functional coupling to a recently cloned G protein-activated $K^+$ channel. When both proteins were expressed in Xenopus oocytes, upon repeated stimulation of the μ opioid receptor, functional desensitization developed, as the $K^+$ current induced by the second μ receptor activation is reduced compared to that by the first μ receptor activation. The extent of desensitization is augmented by both the protein kinase C and the multi-functional calcium/calmodulin-dependent protein kinase.

The μ opioid receptor is the physiological target of such potent analgesics as morphine, and fentanyl, as well as the endogenous opioid peptides, β-endorphin, enkephalins and dynorphins; and the μ opioid receptor has been implicated in the cellular mechanisms involved with analgesia (Wood and Iyengar, 1988). Opioid narcotics with high liability of abuse include morphine, methadone, and fentanyl, and they are all selective ligands at the μ receptor. In addition, heroin (diacetylmorphine) is a semi-synthetic derivative or morphine. It crosses the blood-brain barrier much more readily than morphine, due to its increased hydrophobicity. Once in the brain, heroin is rapidly hydrolyzed to morphine, which acts at the μ opioid receptor and results in an euphoric effect, thus conferring the reinforcing properties of the drug and contributing to the development of addiction. Because of the high affinity of these opioid narcotics at the μ receptor, it is considered the main cellular mediator in the development of tolerance (Loh et al., 1988), and opioid addiction (Di Chiara and North, 1992).

The activation of all three opioid receptor types can inhibit adenylyl cyclase and modulate membrane conductances of $Ca^{2+}$ and $K^+$ (Childers, 1993; North, 1993). The increase in $K^+$ conductance and the decrease in $Ca^{2+}$ conductance both serve to reduce membrane excitability and may account for the analgesic properties of the opioids (North, 1993). Electrophysiological recordings from neurons located in the locus ceruleus (Miyake et al., 1989; Alreja and Aghajanian, 1993) and hippocampus (Wimpey and Chavkin, 1991) indicate that μ opioid receptor stimulation causes membrane hyperpolarization via an inwardly rectifying $K^+$ conductance. The effect of the receptors upon the ion channels requires GTP but no diffusible cytosolic molecules. The inhibition of adenylyl cyclase, however, implicates a more complex mode involving opioid regulation of cellular mechanisms, which includes controlling the levels of gene expression as well as modulating the activity of cellular phosphatases and kinases (Di Chiara and North, 1992; Guitart and Nestler, 1993).

Analgesia and the development of opioid tolerance, dependence, and addiction have been the subject of extensive studies (Collin and Cesselin, 1991). Several schemes, including receptor-mediated modulation of membrane conductance, have been proposed for the acute and chronic actions of opioids in the central nervous system (Johnson and Fleming, 1989). One scheme involves protein phosphorylation by various kinases as a possible way to regulate opioid-induced cellular processes. The molecular mechanism of such regulation, however, has not been clearly delineated. In this experiment, the expression of the human μ opioid receptor and a G protein-activated $K^+$ channel in Xenopus oocytes is described, and the role of protein kinases in modulating the μ receptor-$K^+$ channel coupling is examined. These results demonstrate that protein kinases do modulate desensitization of the μ opioid receptor-mediated $K^+$ channel activity. Since it has been suggested that opioid tolerance is associated with an impairment of the interactions between the opioid receptor and those molecules which transduce its effects (Collin and Cesselin, 1991), the mechanisms described here for kinase modulation of μ receptor-mediated intracellular signalling may contribute to the physiological basis of opioid tolerance, dependence, and addiction.

A. Experimental Procedures

Isolation of the Human μ Opioid Receptor cDNA: The open reading frame-containing fragment of the rat μ opioid receptor cDNA was used to screen a λgt11 human cDNA library prepared from caudate nucleus mRNA (Clontech) under conditions of low stringency (6×SSPE (1.08 M NaCl, 60 mM $NaH_2PO_4$, 6 mM EDTA, pH 7.4), 5×Denhardt's solution (0.1% each of Ficoll 400, polyvinylpyrrolidone, bovine serum albumin), 0.5% sodium dodecyl sulfate, 100 μg/ml salmon sperm DNA, at 48° C.). The final wash was performed in 1×standard saline citrate (150 mM NaCl, 15 mM sodium citrate) 0.1% sodium dodecyl sulfate, at 50° C. Positive λ clones were plaque-purified and subcloned into pBluescript KS(+). End-terminal sequencing of subclones identified potential opioid-like cDNAs. One was chosen for complete sequence determination of both strands. Potential post-translational modification sites were identified by using the PCGENE analysis program. Alignment of receptor sequences was performed with the GCG "PILEUP" program from the Genetics Computer Group software package (Devereux et al., 1984).

RNA Blot Analysis: A blot from Clontech, containing 2 μg of polyadenylated RNA in each lane, was prehybridized, hybridized and washed according to the manufacturer's specifications. Briefly, the blot was prehybridized for 6 hours at 42° C. in a solution containing 5×SSPE, 10×Denhardt's solution, 100 μg/ml denatured, sheared salmon sperm DNA, 50% formamide, and 2% sodium dodecyl sulfate. The cDNA probe (25 ng) was labeled using random hexamer priming (Pharmacia). Hybridization was performed for 18 hours at 42° C. with the addition of probe to a density of $2×10^6$ cpm/ml of prehybridization solution.

Final wash conditions were 0.1×standard saline citrate and 0.1% sodium dodecyl sulfate at 50° C. for 40 min. The blot was exposed to Kodak XAR film for autoradiography.

Receptor Expression in COS-7 Cells: The cDNA containing the open reading frame of the receptor was cloned downstream of the human cytomegalovirus promoter in the mammalian expression vector, pcDNA3 (Invitrogen). COS-7 cells were grown in Dulbecco's modified Eagle's medium (Sigma D-5648) supplemented with 10% fetal bovine serum and 2 mM L-glutamine and were electroporated with supercoiled DNA in 0.4 cm cuvettes at 250 V, using 3×10$^6$ cells in a total volume of 0.5 ml containing growth medium, 40 μg of expression plasmid, and 200 μg of sheared salmon sperm DNA. Cells were harvested 48–72 hours after electroporation. Cells were harvested by scraping into phosphate-buffered saline, pH 7.2, and centrifuged. Cell pellets were resuspended in ice-cold lysis buffer (20 mM Tris-HCl, pH 7.4, 5 mM EDTA, 1 mM phenylmethylsulfonyl fluoride) and lysed with a Dounce homogenizer. The homogenate was saved. The pellet was resuspended in lysis buffer and centrifuged as described before. Supernatants were combined and centrifuged for 10 min at 35,000×g. Membrane pellets were washed in 50 mM Tris-HCl, pH 7.4, centrifuged again, and resuspended in 50 mM Tris-HCl, pH 7.4. Protein concentrations were determined by the method of Bradford (Bradford, 1976).

Binding Analysis: Binding assays were performed essentially as described (Chen et al., 1993a). Binding mixtures containing at least 10 μg membrane protein were incubated at room temperature for 90 min in 50 mM Tris-HCl, pH 7.4 containing 0.2% bovine serum albumin, various concentrations of unlabeled ligands, and [$^3$H]diprenorphine ([$^3$H]DPN) or [$^3$H]DAMGO, in a final volume of 200 μl. Reactions were terminated by quickly adding 3 ml of ice-cold binding buffer (50 mM Tris-HCl, pH 7.4) followed by vacuum filtration onto Whatman GF/B glass fiber filters, presoaked for 3 hours in 0.2% polyethylenimine to minimize non-specific binding. Filters were washed two times each with 3 ml of ice-cold binding buffer before placed in vials containing 10 ml liquid scintillation cocktail (CytoScint). Radioactivity was determined using a Beckman LS-5801 scintillation counter. Non-specific binding was defined as the radioactivity bound in the presence of 10 μM unlabeled naloxone. Saturation analyses were performed as above with increasing concentrations of [$^3$H]DPN (0.01 to 2.5 nM) or [$^3$H]DAMGO (0.05 to 5 nM).

Data for all saturation binding experiments were analyzed by using the linear/non-linear regression analysis program, EBDA/LIGAND (Munson, 1983) to obtain estimates of equilibrium dissociation constant ($K_d$), Hill slope ($n_H$), and binding site density ($B_{max}$) values. Competition curves were obtained with 1.3 nM [$^3$H]DAMGO incubated with concentrations of the indicated competitors from 0.01 nM to 5 μM. IC$_{50}$ values were determined through non-linear regression using InPlot, which utilizes the Cheng-Prusoff equation to determine the $K_i$ values (Cheng and Prusoff, 1973).

Oocyte Expression of the Receptor and the G Protein-Activated K$^+$ Channel: The cloning of the G protein-activated inwardly rectifying K$^+$ channel has been described (Dascal et al., 1993; Kubo et al., 1993). The cDNAs encoding the G protein-activated K$^+$ channel were obtained from Drs. Lily Jan and Henry Lester. Synthetic mRNAs for the human μ opioid receptor and the G protein-activated K$^+$ channel were transcribed in vitro as described (Chen and Yu, 1994). RNA yield was calculated from incorporation of the radioactive precursor, [α-$^{32}$P]UTP.

Oocytes were isolated using standard methods (Gurdon and Wickens, 1983). Ovarian lobes were surgically removed from mature *Xenopus laevis* females and individual oocytes were isolated by digestion with 2 mg/ml collagenase in OR-2 (82.5 mM NaCl, 2 mM KCl, 1 mM MgCl$_2$, 5 mM HEPES, pH 7.5) for 1–2 hours at room temperature. Stage V and VI oocytes were injected with a total of 50 nl containing 0.1 ng of each mRNA and incubated for 2–3 days at 20° C. in ND96 (96 mM NaCl, 2 mM KCl, 1 mM MgCl$_2$ and 1.5 mM CaCl$_2$) supplemented with 10 μg/ml gentamycin and 5% fetal bovine serum.

Electrophysiology: Oocytes were voltage-clamped using a two-microelectrode voltage-clamp and the data were analyzed with pCLAMP software (Axon Instruments). The electrodes were filled with 3 M KCl and had tip resistances of 0.5–10 MΩ. Oocytes were superfused with either a high K$^+$ solution, HK (96 mM KCl, 2 mM NaCl, 1 mM MgCl$_2$ and 1.5 mM CaCl$_2$) or ND96 containing the appropriate agonist or kinase modulator. Phorbol 12-myristate 13-acetate (PMA), a protein kinase C activator, and 4α-phorbol, an inactive phorbol ester, were diluted to final concentrations of 100 nM in ND96 for oocyte superfusion. CaM kinase II was purified from rat brain as described (Schulman, 1984). The holoenzyme was activated to become Ca$^{2+}$/calmodulin-independent by autophosphorylation as described (Waldmann et al., 1990) with the following modifications: CaM kinase II (75 nM) was incubated with 1 μM calmodulin, 100 μM ATP, 0.1 mM CaCl$_2$, 2 mM DTT, 40 mM HEPES, pH 7.4 at 4° C. for 20 min. EGTA was added to a final concentration of 0.12 mM. Aliquots of autophosphorylated CaM kinase II were stored at −70° C. until used. Oocytes were injected with 50 nl of the reaction mixture (2 fmols of CaM kinase II per cell). Analysis of variance and Student's t test were used to compare the treatment groups.

B. Results

Isolation and Characterization of cDNA Encoding the Human μ Opioid Receptor: To clone the human μ opioid receptor, a cDNA library constructed from human caudate nucleus mRNA was screened under reduced stringency with the rat μ opioid receptor cDNA (Chen et al., 1993a), and the cDNA inserts from positive clones were subcloned into pBluescript. Complete sequence analysis of one cDNA, SEQ ID NO: 7, revealed an open reading frame of 1200 bp, predicting a protein of 400 amino acids. Hydropathy analysis of the deduced protein indicated the presence of seven hydrophobic domains, typical of G protein-coupled receptors (Collins et al., 1991). The sequence of this protein, SEQ ID NO: 8, displays 94% similarity to the rat μ opioid receptor (Chen et al., 1993a; Wang et al., 1993; Fukuda et al., 1993; Thompson et al., 1993), suggesting that it is the human homologue of the μ opioid receptor. It also displays 62% and 58% similarities to the murine δ (Kieffer et al., 1992; Evans et al., 1992; Fukada et al., 1993) and κ (Yasuda et al., 1993; Chen et al., 1993b; Li et al., 1993; Meng et al., 1993; Minami et al., 1993) opioid receptors, respectively.

The regions of greatest divergence among the different types of opioid receptors include the N- and C-termini, the fourth and sixth transmembrane domains and the second and third extracellular loops. Several potential sites for post-translational modification are present. The N-terminus contains five potential N-linked glycosylation sites which remain conserved between the human and rat μ opioid receptors. Aspartic acid residues which occur in other G protein-coupled receptors and have been shown to interact with the protonated amine group of various ligands (Dohlman et al., 1991) are also present in the putative transmembrane domains TM2 and TM3 of the μ receptor, and two conserved cysteine residues believed to be involved in disulfide bonding (Dixon et al., 1988) occur in the first and second extracellular loops. There are also potential phosphorylation sites for protein kinase A (PKA) and protein kinase C (PKC), as well as the multi-functional calcium/calmodulin-dependent protein kinase (type II $Ca^{2+}$/calmodulin-dependent kinase, CaM kinase). One of these sites, conserved among all opioid receptor types, occurs in the third intracellular loop. This region between TM5 and TM6 is often referred to as the G protein loop because of its importance in G protein coupling (Dohlman et al., 1991). The conservation of this site suggests that phosphorylation may play a role in modulating signal transduction of all the opioid receptors. There is also a cysteine residue in the C-terminus that is conserved among many G protein-coupled receptors and that may serve as a target for palmitoylation (Collins et al., 1991).

Figure 4:
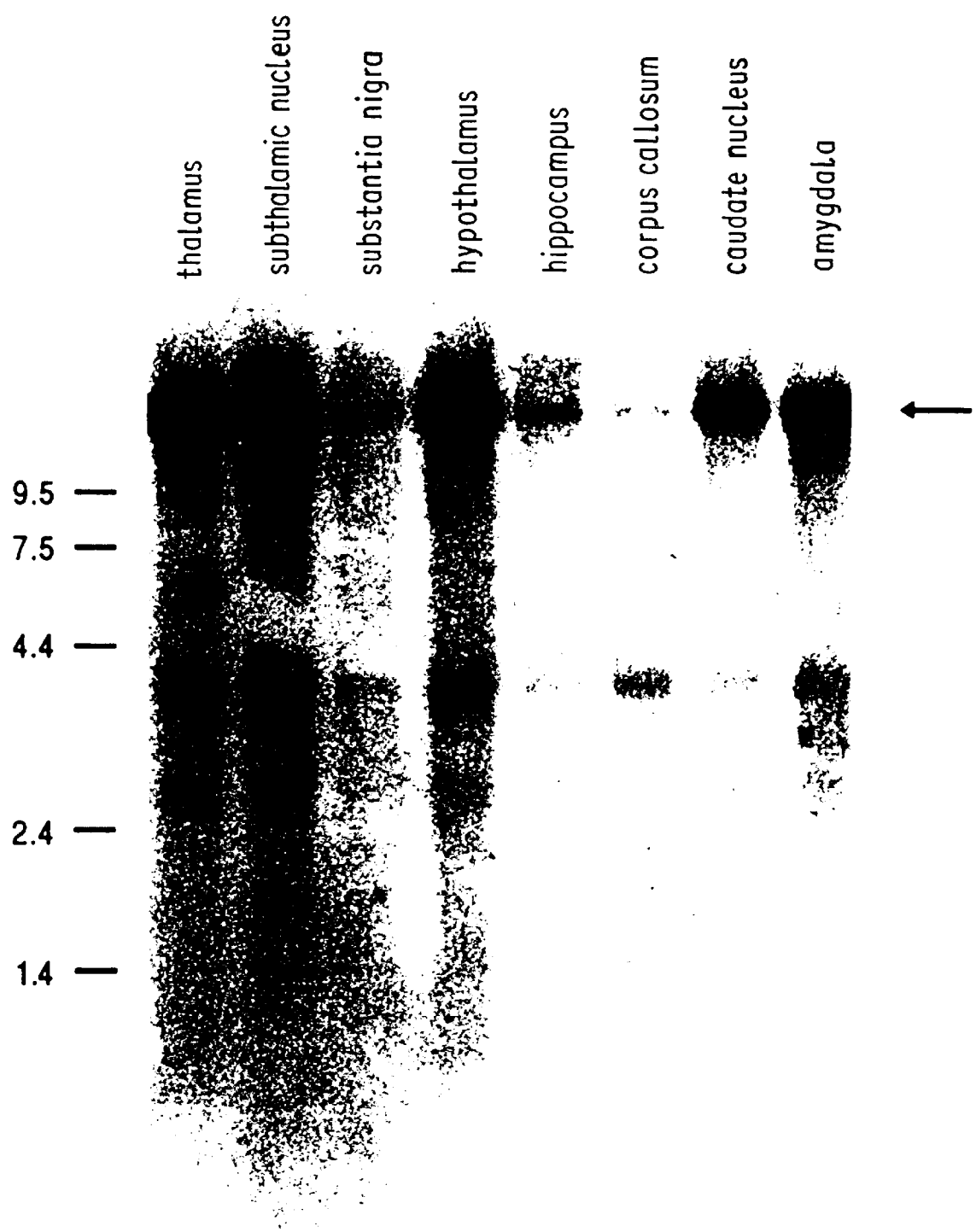
FIG. 4. Expression of the Human $\mu$ Opioid Receptor in Human Brain RNA blot analysis of the $\mu$ opioid receptor message in various regions of the human brain. The size markers are indicated on the left. The predominant 14 kb band is marked by an arrow.

Expression of the Receptor mRNA in Human Brain: To estimate the relative abundance of the $\mu$ opioid receptor mRNA, a blot containing polyadenylated RNA from various regions of the human brain was hybridized with a probe containing the open reading frame of this cDNA (FIG. 4). The predominant mRNA is approximately 14 kb, similar in size to those reported for the rat $\mu$ opioid receptor (Fukuda et al., 1993; Thompson et al., 1993, Delfs et al., 1994). This message is abundant in the thalamus, hypothalamus, and subthalamic nucleus where $\mu$ opioid receptors are believed to modulate nociception. Somewhat lower levels of message are observed in the caudate nucleus and amygdala which harbor synapses between cortical neurons and motor nuclei located in the brainstem and spinal cord. These basal ganglia as well as the subthalamic nucleus which serves as a "way station" for this extrapyramidal tract may allow for opioid-mediated integration of somatosensory input and motor output. The substantia nigra, corpus callosum, and hippocampus express the $\mu$ receptor mRNA in lower abundance than that seen in the other brain subregions. Recent in situ hybridization studies in rat brain (Thompson et al., 1993; Delfs et al., 1994) have provided cellular resolution of $\mu$ opioid receptor message expression and corroborate these results of the subregion RNA analysis.

Pharmacological Characterization of the Receptor: The cDNA containing the open reading frame was subcloned into a mammalian expression vector containing the human cytomegalovirus promoter. This construct was transiently expressed in COS-7 cells, and saturation binding of [$^3$H] diprenorphine to the membranes was performed. As shown in FIG. 5A, a saturable binding was observed with a dissociation constant ($K_d$) of 0.23±0.01 nM (n=3) and a $B_{max}$ of 549±26 fmol/mg of membrane protein. Hill coefficients (0.97±0.01) did not suggest the presence of any cooperative binding effects. The equilibrium binding parameters for [$^3$H]DAMGO, a $\mu$-selective agonist, were 1.6±0.15 nM for the $K_d$ and 381±25 fmol/mg membrane protein for $B_{max}$.

Figure 5B:
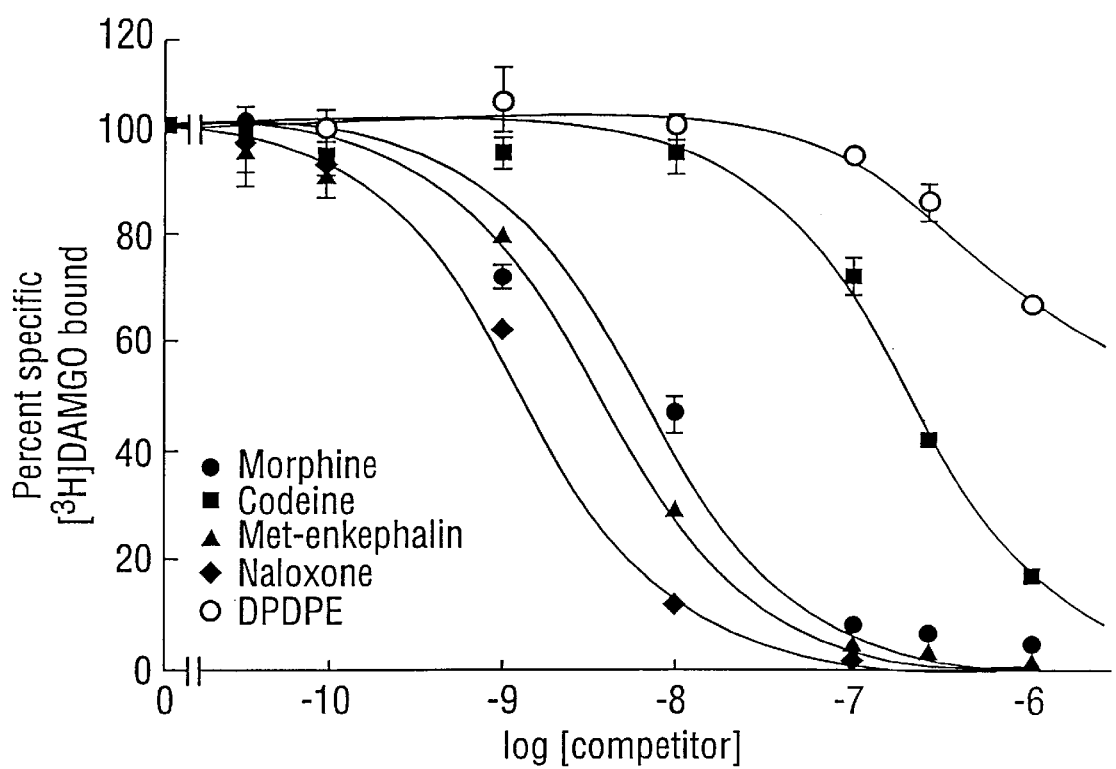
FIG. 5. Panels A and B of FIG. 5 show Saturation and Displacement Binding of Labeled Ligands Using Cell Membranes Transiently Expressing the Human $\mu$ Opioid Receptor (A) Saturation binding of [$^3$H]diprenorphine (DPN) was determined using membranes prepared from cDNA- transfected COS-7 cells. Data for all saturation binding experiments were analyzed using the linear/non-linear regression analysis program EBDA/LIGAND (Munson, 1983) to obtain estimates of $K_d$ and $B_{max}$ values. Data represent mean±SEM of 3 separate experiments performed in duplicate. Inset: Saturation binding plotted in Scatchard coordinates (representative curve shown). (B) Displacement of [$^3$H]DAMGO binding with unlabeled ligands as competitors. Displacement of [$^3$H]DAMGO binding was performed using 1.3 nM [$^3$H]DAMGO and unlabeled competitors with concentrations ranging from 0.01 nM to 5 $\mu$M. Data represent mean±SEM of 3 separate experiments performed in duplicate.

To characterize the pharmacological profile of this receptor, competitive displacement experiments were performed with various opioid ligands. Representative binding isotherms are shown in FIG. 5B, and $IC_{50}$ and $K_i$ values are summarized in Table 3. The $\mu$-selective agonist, DAMGO, displaced [$^3$H]DAMGO binding with high affinity ($K_i$=0.9 nM). Two other opioid ligands, DPDPE and U-50,488, which are selective for $\delta$ and $\kappa$ receptors, respectively, displayed low affinity binding with $K_i$ values above the mM range. Displacement of [$^3$H]DAMGO from membranes expressing the human $\mu$ opioid receptor was also performed using opioid antagonists. Cyprodime and naloxonazine, both $\mu$-selective antagonists, bound with $K_i$ values in the nM range. Naloxone, a non-selective opioid antagonist, bound with an affinity nearly equal to that of DAMGO. The rank order affinity for these ligands (Table 2) and the high affinity for $\mu$-selective ligands indicate that this cDNA encodes a $\mu$ opioid receptor.

Table 3. IC50 and Ki Values of Various Opioid Receptor Ligands for the Cloned Human $\mu$ Receptor.

| Competitor | $IC_{50}$ (nM) | $K_i$ (nM) |
| --- | --- | --- |
| β-endorphin | 3.4 ± 0.5 | 1.8 ± 0.3 |
| CHB | 25.6 ± 9.5 | 14.1 ± 5.3 |
| Codeine | 235.3 ± 14.5 | 128.0 ± 8.7 |
| DAMGO | 1.7 ± 0.4 | 0.9 ± 0.2 |
| DPDPE | >1000 | >1000 |
| Dynorphin A | 3.0 ± 0.5 | 1.6 ± 0.3 |
| Fentanyl | 4.8 ± 0.8 | 2.6 ± 0.4 |
| Leu-enkephalin | 17.7 ± 7.4 | 9.5 ± 4.0 |
| Met-enkephalin | 4.1 ± 0.1 | 2.2 ± 0.1 |
| Methadone | 6.9 ± 0.1 | 3.7 ± 0.03 |
| Morphine | 6.6 ± 0.5 | 3.6 ± 0.3 |
| Naloxonazine | 1.8 ± 0.2 | 1.0 ± 0.1 |
| Naloxone | 1.5 ± 0.2 | 0.8 ± 0.1 |
| U-50,488 | >1000 | >1000 |

Competition curves were obtained with 1.3 nM [$^3$H] DAMGO incubated with concentrations of the indicated competitors ranging from 0.01 nM to 5 $\mu$M (200 $\mu$l final volume). $IC_{50}$ values were determined using non-linear regression. $K_i$ values were calculated using the Cheng-Prusoff equation (Cheng and Prusoff, 1973). Values shown are mean±SEM of 3 experiments performed in duplicate. Abbreviations: CHB, cyprodime HBr; DAMGO, [D-Ala$^2$, N-Me-Phe$^4$,Gly-ol$^5$]-enkephalin; DPDPE, [D-Pen$^{2,5}$] enkephalin.

Competitive displacement binding was also done with several therapeutic opioid ligands. Morphine, methadone and fentanyl, archetypal drugs that bind the $\mu$ opioid receptor, all displayed nM affinity. Codeine, showed lower affinity with $K_i$ values in the high nM range. Several endogenous opioid peptides were also tested. Met-enkephalin, β-endorphin, and dynorphin A all displayed high affinities comparable to that observed for DAMGO, suggesting that they may act at this receptor in vivo.

Functional Coupling to a G Protein-activated K$^+$ Channel: Activation of opioid receptors has been known to affect membrane permeability to potassium (North, 1993). Stimulation of the $\mu$ opioid receptor hyperpolarizes cellular membranes by increasing the K$^+$ conductance through an inwardly rectifying channel (North et al., 1987; Wimpey and Chavkin, 1991). The recent cloning of an inwardly rectifying K$^+$ channel (Dascal et al., 1993; Kubo et al., 1993) was shown to be expressed in the brain, and the inventor was interested in testing whether the human $\mu$ opioid receptor coupled to this G protein-activated K$^+$ channel. Messenger RNAs encoding both proteins (Chen and Yu, 1994) were generated by in vitro transcription and injected into Xenopus oocytes. Coupling of the receptor to the K$^+$ channel was assessed by two-electrode voltage clamp. When the receptor was activated by superfusing the oocytes with DAMGO, an inward current was observed (FIG. 6A). This is a K$^+$ current through the inwardly rectifying K$^+$ channel, since the current varies in amplitude with the concentration of K$^+$ in the extracellular solution and is blocked by the K$^+$ channel blocker Ba$^{2+}$ (100 $\mu$M). Oocytes injected with the receptor mRNA alone do not produce the current upon DAMGO stimulation. This K$^+$ current is induced by activation of the $\mu$ opioid receptor, since the current produced by exposure to DAMGO was completely blocked by the opioid antagonist naloxone (FIG. 6B). The current-voltage relationship of this K$^+$ channel was characteristic of an inward rectifier. With progressive hyperpolarization, the magnitude of current increases (FIG. 6C). However, as the membrane is depolarized, current flow decreases until there is little to none at a membrane potential of 0 mV. Thus, the human $\mu$ opioid receptor is capable of coupling to the G protein-activated K$^+$ channel.

Figures 1, 7A:
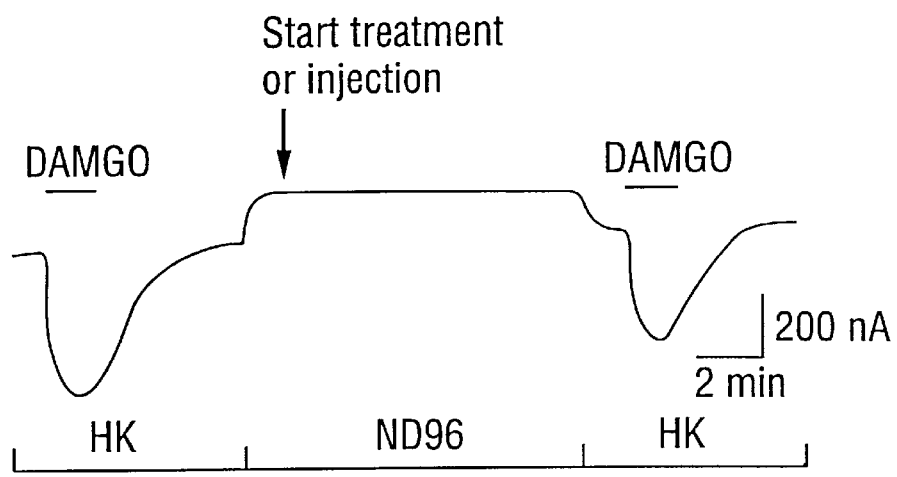
Figures 2, 7A:
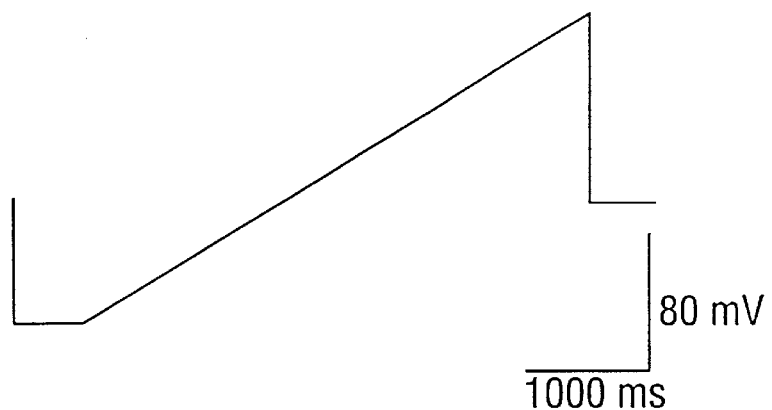
Figures 3, 7A:
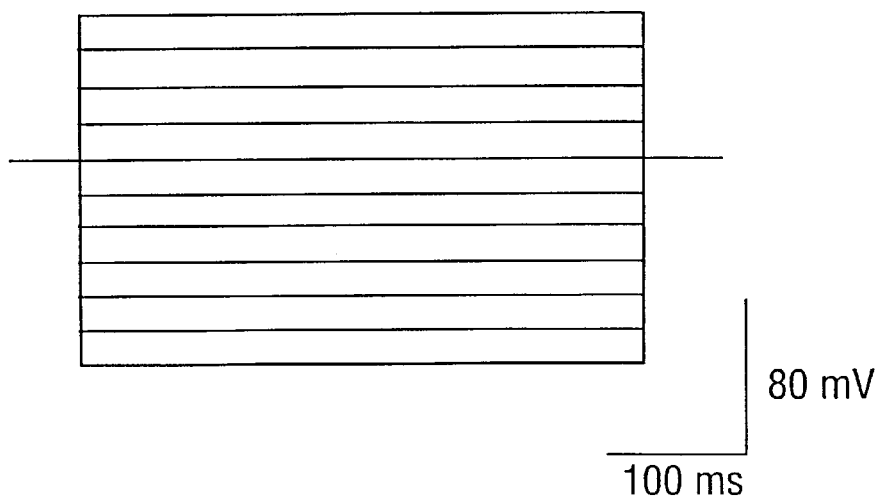

Repeated Agonist Stimulation Desensitizes Receptor-Channel Coupling: Prolonged exposure to opioids are known to produce tolerance (Di Chiara and North, 1992). At the cellular level, tolerance is manifested as a diminished response to opioids (Johnson and Fleming, 1989). Since the opioid narcotics with abuse liability, such as morphine, methadone and fentanyl, have high affinity at the $\mu$ opioid receptor (Table 3), the inventor was interested in examining whether the intracellular signaling by the $\mu$ opioid receptor displays tolerance. Using the receptor-K$^+$ channel coupling as an assay, oocytes were subjected to repeated agonist stimulation to determine whether functional desensitization of the $\mu$ receptor-K$^+$ channel coupling occurs. For this purpose, a protocol of repeated agonist application was used (FIG. 7A, top), and "desensitization" was operationally defined as a reduction in the second response compared to the first response. Current traces at −80 mV were recorded for each stimulation with DAMGO to evaluate the extent of desensitization. In addition, currents over the entire voltage range between −160 mV and +40 mV were recorded using either a ramp (FIG. 7A, middle) or stepped voltage commands (FIG. 7A, bottom). Repeated stimulation of the $\mu$ receptor resulted in a moderate and consistent desensitization as observed by a reduction in the second response. The second response was reduced to 83%+8% (n=4) relative to the first (FIG. 9), and this reduction was proportional across the entire voltage range.

Figures 1, 7B:
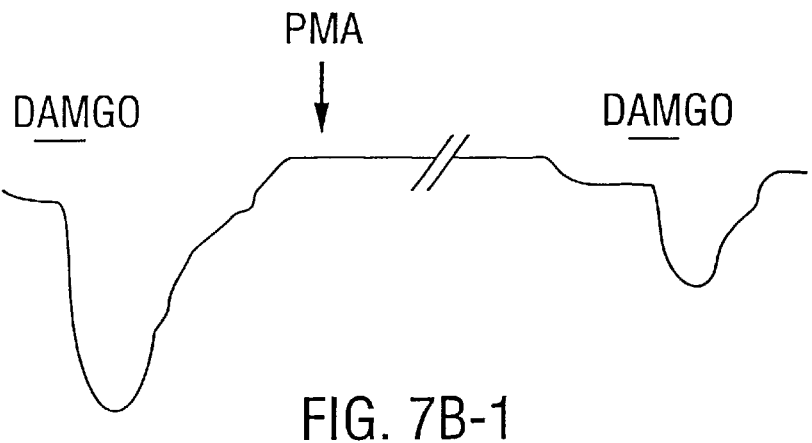
Figures 2, 7B:
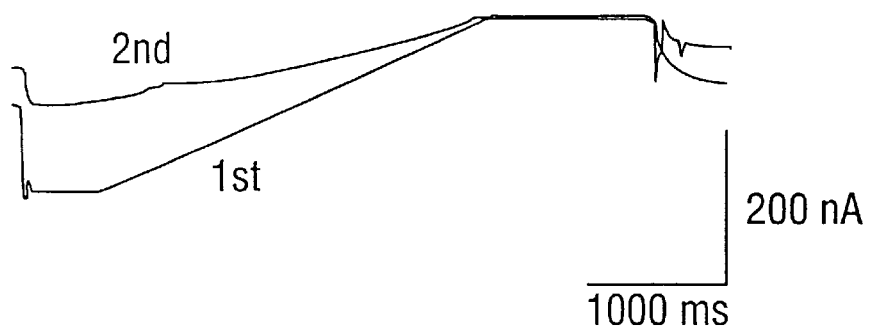
Figures 3, 7B:
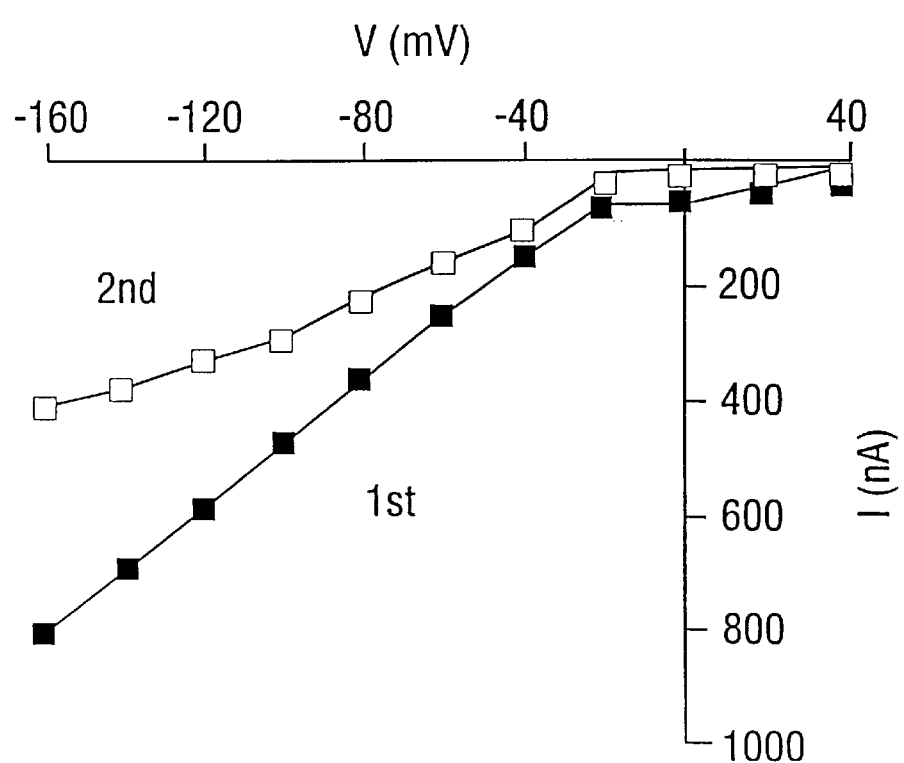
Figures 1, 7C:
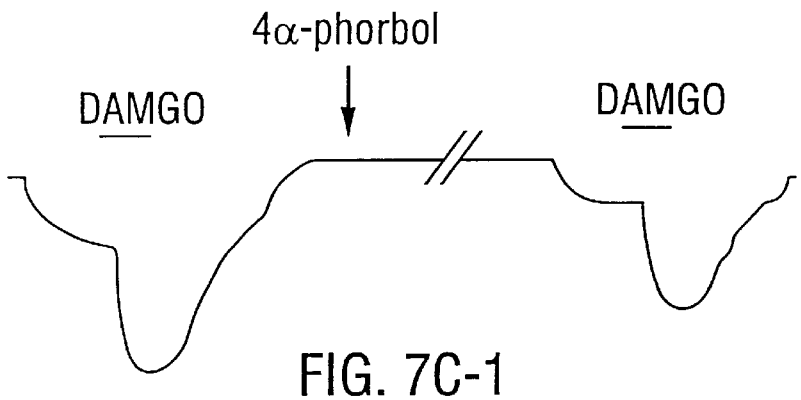
Figures 2, 7C:
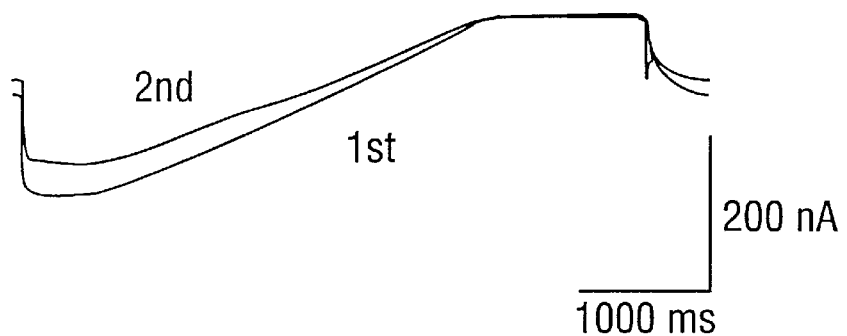
Figures 3, 7C:
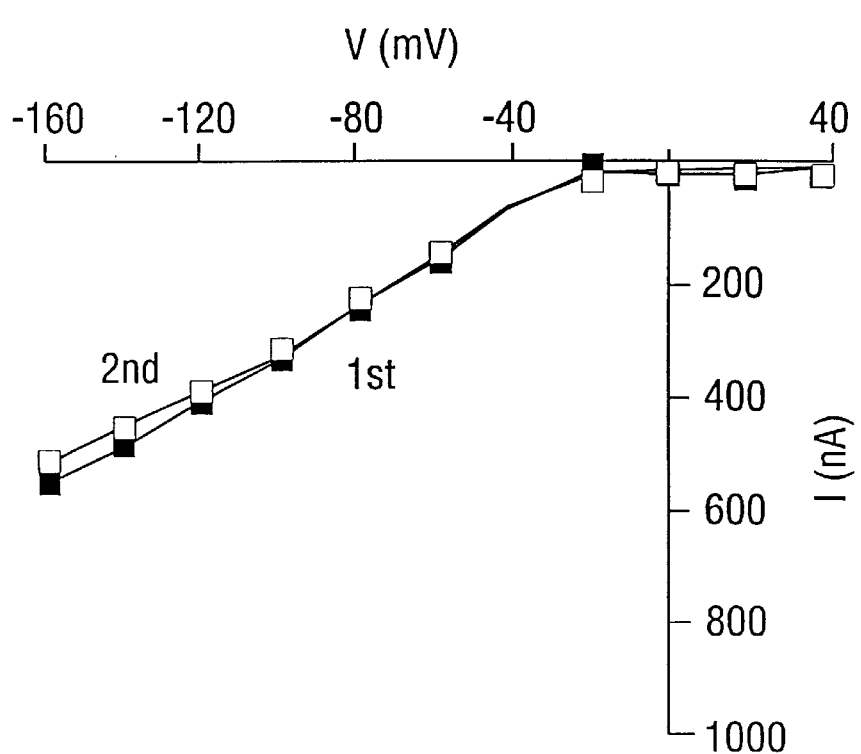
Figure 9:
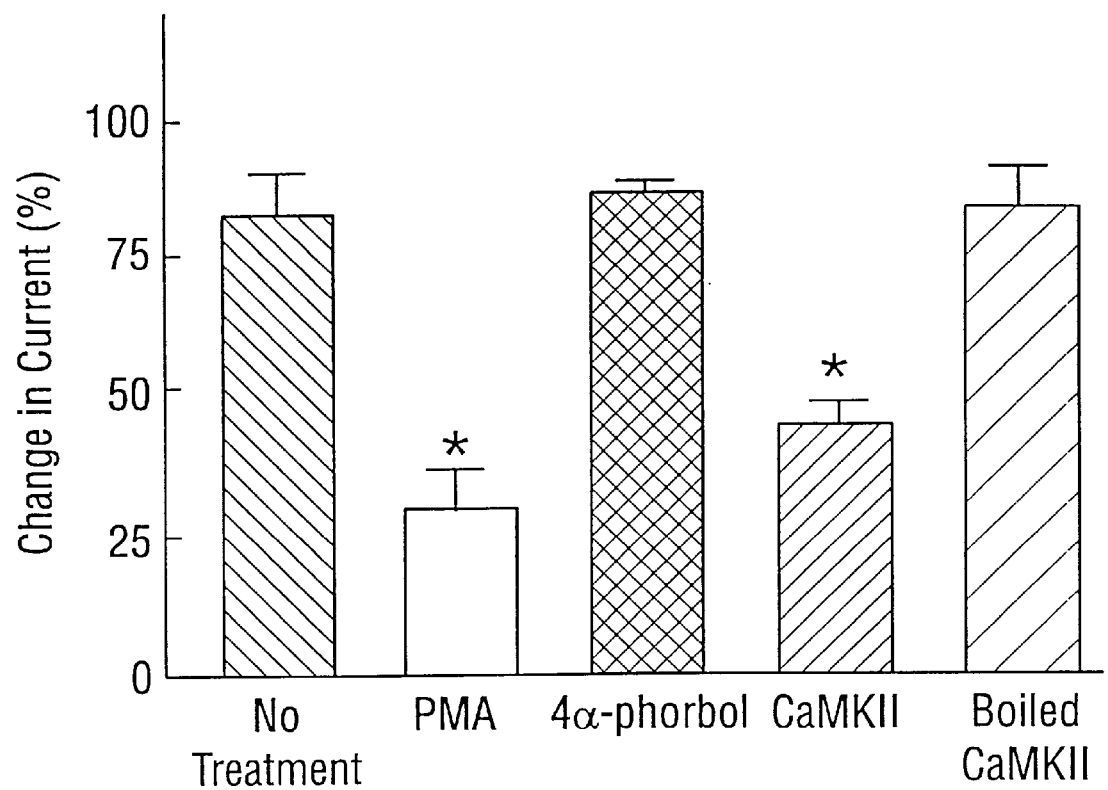
FIG. 9. Desensitization of the Human μ Opioid Receptor-induced $K^+$ Current and Modulation by PKC and CaM Kinase II Oocytes were injected with both the human μ opioid receptor and the inwardly rectifying $K^+$ channel mRNAs. Membrane currents were recorded at a holding potential of −80 mV during DAMGO application and recording of peak currents. Data are expressed as the percentage of the peak current induced by the second DAMGO stimulation over that of the first stimulation and are presented as mean±SEM. Treatment is labeled on the bottom of each data group. Analysis of variance and posthoc test results: * indicates $p<0.05$ as compared to untreated group.

Protein Kinases Augment Desensitization of Receptor-Channel Coupling: Previous studies had shown that activation of protein kinase C (PKC) was capable of attenuating opioid receptor activity in neuroblastoma cells (Louie et al., 1990) as well as affecting ion conductances using acutely dissociated neurons in culture (Doerner et al., 1988). A study was conducted to observe whether stimulation of PKC affects the coupling of the human $\mu$ opioid receptor to the K$^+$ channel. Using the protocol described above (FIG. 7A, top), Xenopus oocytes were superfused for 10–15 minutes after the initial DAMGO stimulation with phorbol 12-myristate 13-acetate (PMA), a PKC activating phorbol ester. Oocytes were again stimulated with DAMGO. Comparison between the peak current responses to DAMGO before and after PMA treatment reveals the extent of desensitization (FIG. 7B, top). PMA reduced the second response to 29%+7% (n=4) relative to the first (FIG. 9) at the holding potential of −80 mV. Current responses were also obtained using a ramp voltage command. Representative current traces from before and after PMA treatment are superimposed (FIG. 7B, middle). Currents produced by stepped voltage commands were measured and the reduction in response was shown to be proportionally uniform across the voltage range (FIG. 7B, bottom). Thus, activation of PKC potentiated the desensitization of the $\mu$-opioid receptor-activated K$^+$ current. To control for possible non-specific effects caused by application of a phorbol ester to the cellular membrane, oocytes were treated with 4α-phorbol, a phorbol ester that does not activate PKC (Blumberg et al., 1984). Recordings of peak current amplitude show that the 4α-phorbol does not potentiate desensitization (87%+2%, n=4) beyond that observed with no treatment (FIG. 7C, top, and FIG. 9). Membrane currents from ramp (FIG. 7C, middle) and stepped voltage commands (FIG. 7C, bottom) before and after 4α-phorbol treatment exhibited moderate desensitization comparable to that with no treatment, demonstrating that the inactive form of the phorbol ester does not potentiate desensitization. Therefore, these results indicate that potentiation of the desensitization by PMA reflects the activation of PKC.

Figures 1, 8B:
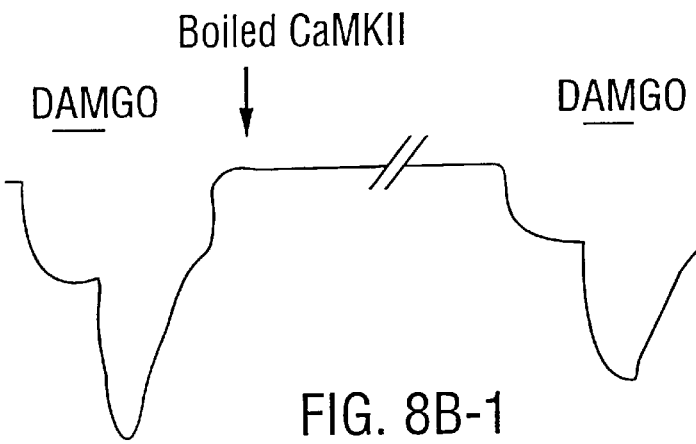

Physiologically, PKC is activated by diacylglycerol (DAG), a second messenger of the phosphatidylinositol pathway. This signaling pathway also generates another second messenger, inositol 1,4,5-trisphosphate (IP3), which triggers an increase in intracellular calcium and results in the activation of the multi-functional Ca$^{2+}$/calmodulin-dependent protein kinase (type II Ca$^{2+}$/calmodulin-dependent protein kinase, CaM kinase II) (Schulman and Hanson, 1993). A study was conducted to test whether CaM kinase II could modulate the $\mu$ opioid receptor-mediated K$^+$ current. Using the protocol described above, oocytes were injected with the activated form of CaM kinase II between the first and second stimulations with DAMGO, and the effect on the receptor-induced K$^+$ current was evaluated. Injection of activated CaM kinase II reduced the second response to 44%+4% (n=8) compared to the first (FIG. 8A, top, and FIG. 9). CaM kinase II clearly enhanced the desensitization, causing a two-fold decrease in the second response relative to uninjected oocytes. This reduction in the second response was proportional across the entire voltage range (FIG. 8A, middle and bottom). As a negative control, the same CaM kinase II solution was placed in a boiling water bath for 5 minutes and chilled on ice before injection into the oocytes. Boiled CaM kinase II did not potentiate desensitization (84%+8%, n=8) beyond that observed with uninjected controls (FIG. 8B, top, and FIG. 9). Currents measured during the ramp or stepped voltage commands were similar both before and after injection of boiled CaM kinase II (FIG. 8B, middle and bottom). Activated CaM kinase II can therefore potentiate the desensitization of the $\mu$ opioid receptor-activated K$^+$ current.

C. Discussion

The $\mu$ opioid receptor mediates the effects of such potent analgesics as morphine, codeine, methadone and fentanyl. To explore the molecular basis of opioid actions and the possible mechanisms involved in tolerance development, a cDNA clone encoding the human $\mu$ opioid receptor was isolated. The deduced protein sequence of this receptor is very similar to that of its homologue from the rat brain (Chen et al., 1993a). Although the N-terminus of the human $\mu$ opioid receptor contains two additional amino acids not found in the rat homologue, the protein sequences are so similar that only two conservative amino acid substitutions occur in the region between TM1 and TM7, the core region of G protein-coupled receptors that are involved in ligand binding and signal transduction. Such structural conservation between the human and rat $\mu$ opioid receptors would imply a functional conservation. Pharmacologically, they display very similar binding profiles for $\mu$-selective and non-selective ligands. Binding studies using brain homogenate have shown that opioid narcotics that have high liability of abuse, such as morphine, fentanyl, and methadone, all bind to the $\mu$ opioid receptor rather selectively (Pasternak, 1993). Using the murine cDNA clones to express the $\mu$, $\delta$, and $\kappa$ opioid receptors, these opioid narcotics showed highly selective binding at the $\mu$ receptor (Raynor et al., 1994). With the human $\mu$ opioid receptor, nM affinities of the receptor for these compounds have also been observed (Table 3). Also, IC$_{50}$ values for DAMGO, naloxone, morphine, and diprenorphine using human brain preparations (Pilapil et al., 1987; Pfeiffer et al., 1982) are in excellent agreement with those reported here. Since these ligands possess both powerful analgesic effects and abuse potential, the μ opioid receptor may be indeed the physiological mediator of the nociceptive and addictive properties of these narcotics. Another human μ opioid receptor, designated hμOR1, was reported (Wang et al., 1994) that differs from the receptor the inventor cloned by one amino acid in the N-terminus. The binding profiles are almost identical except for that of dynorphin A (1-17). The inventor observed a $K_i$ value of 1.6±0.3 nM whereas the clone isolated by Wang et al. gives a $K_i$ value of 284±110 nM (Wang et al., 1994) a difference of over 100-fold. Dynorphin A has the highest affinity at the K opioid receptor (Goldstein, 1987), and is thus considered a κ agonist (Chavkin et al., 1982). However, while it binds at the κ receptors with subnanomolar affinity, it does display reasonably good binding at the μ opioid receptors, with affinity values in the nanomolar range (Goldstein, 1987; Pasternak, 1993). Thus, the μ receptor may also interact with dynorphin A under physiological conditions. Detailed studies of dynorphin A binding in the human brain are very limited. There are some reports, however, on the comparative studies using rodent and bovine brain membranes (Pasternak, 1993). For example, using guinea pig brain membranes, it has been shown that dynorphin A (1-17) can displace radiolabeled PL-17, a μ-selective ligand, with a 5 nM affinity (Kawasaki et al., 1990). In another study, dynorphin A (1-17) was found to displace radiolabeled DAMGO with 3 nM affinity (Vaughn and Taylor, 1989).

A major effect of the μ opioid receptor in brain is the decrease of neuronal membrane excitability. One of the mechanisms for this effect is an increase in $K^+$ conductance, accomplished by the opening of an inward rectifier, resulting in outward $K^+$ currents and hyperpolarization of the cell membrane (North, 1986; Chavkin, 1988; North, 1993). With the cloning of an inwardly rectifying $K^+$ channel that can be activated by a number of neurotransmitter receptors (Dascal et al., 1993; Kubo et al., 1993), it became possible to examine whether the μ opioid receptor could also activate this channel. The inventor has shown that the μ opioid receptor from both rat (Chen and Yu, 1994) and human (FIG. 6) can activate this channel, causing an increase in $K^+$ conductance. The receptor-channel coupling is clearly mediated through heterotrimeric GTP-binding proteins (G proteins), since a non-hydrolyzable GTP analogue, can enhance the μ receptor-activated $K^+$ current and pertussis toxin treatment can decrease it (Chen and Yu, 1994). Thus, the data suggest that the μ receptor-channel coupling may be the basis for the μ receptor-induced increase in $K^+$ conductance.

Receptor-mediated signaling processes often display desensitization, operationally defined as a decrease in the cellular response to further agonist stimulation upon continual or repeated exposure to agonist (Benovic et al., 1988). This may serve as a physiological mechanism to prevent over-stimulation of the neuron. The μ opioid receptor is the physiological target of morphine and fentanyl, analgesics used in the clinical management of pain. Prolonged use of morphine and related opioids can lead to the development of tolerance, necessitating dosage increases to achieve the same degree of its initial physiological effect. At the cellular level, tolerance manifests itself as a desensitized responsiveness to repeated opioid applications, and it has been hypothesized that several of the intermediates in the μ receptor signaling pathway are involved (Nestler et al., 1993). In the neurons of the rat locus ceruleus, desensitization was observed as a reduction in membrane hyperpolarization upon continued application of $Met^5$-enkephalin. A decrease in $K^+$ conductance was shown to be responsible for the observed effect (Harris and Williams, 1991). In oocytes expressing the human μ opioid receptor and the inwardly rectifying $K^+$ channel, a protocol to evaluate desensitization by measuring the $K^+$ currents evoked by sequential activation of the receptor with a μ-selective agonist was employed (FIG. 7A). Comparison of the maximum $K^+$ currents thus indicates the extent of desensitization between the first stimulus and second stimulus caused by activation of the receptor. Using this paradigm, desensitization occurred consistently, as observed in a reduction of the $K^+$ current to ~80% of the initial response evoked by receptor activation (FIG. 9). Thus, desensitization of receptor-channel coupling appears to be a normal process when studied in oocytes, suggesting that such a phenomenon may exist as an adaptive process in neurons to modulate the responsiveness of the μ receptor-mediated increase in $K^+$ conductance.

Figures 2, 8B:
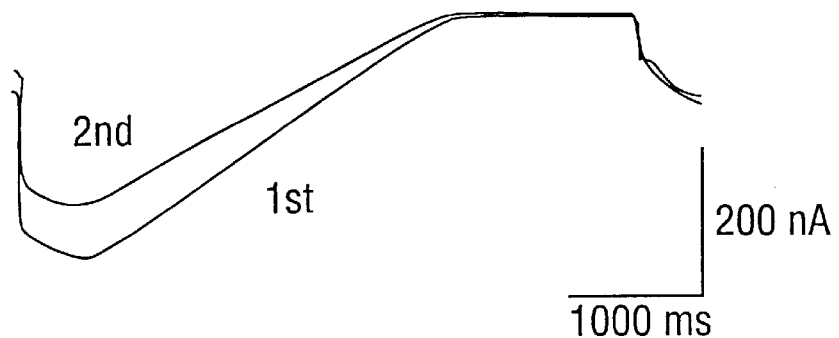
Figures 3, 8B:
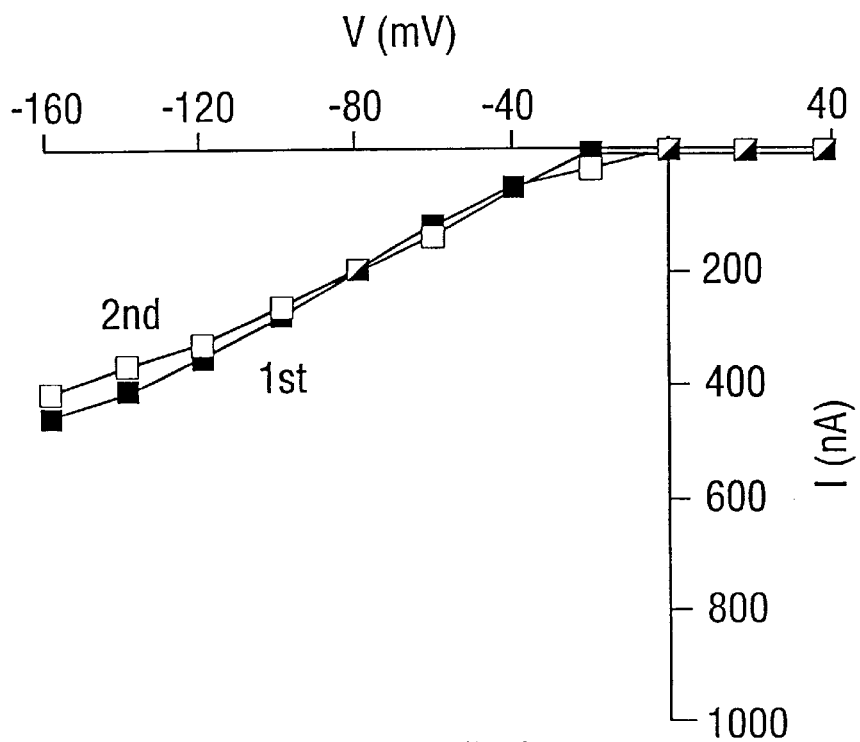

Desensitization of receptor-channel coupling may involve several mechanisms at the cellular level. For acute desensitization such as that studied here with a time-scale of less than 30 minutes, new protein synthesis or receptor turnover are unlikely to account for the majority of the observed effects. Covalent modification through kinase-mediated phosphorylation, on the other hand, appears to play an essential role. Previous studies had suggested that opioid receptor activity was subject to control by agents that stimulate PKC activity (Louie et al., 1990; Attali et al., 1991). The inventor demonstrated that both PKC and CaM kinase II potentiate desensitization (FIGS. 7 and 8). Activation of PKC by the phorbol ester PMA, and injection of the type II CaM kinase activated by autophosphorylation resulted in potentiation of desensitization (FIG. 9). In contrast, treatment with the inactive 4α-phorbol ester or injection of boiled CaM kinase II did not enhance desensitization beyond that observed in oocytes that had been untreated (FIG. 9), suggesting that the potentiation effect is specific to the active form of these kinases. When activated individually, PKC and CaM kinase (Shearman et al., 1989; Akasu and Tokimasa, 1992) have been shown to decrease $K^+$ conductance in neurons which supports these observations in Xenopus oocytes. Processes that elevate the activity of these cellular kinases, therefore, may play an important role in regulating the extent of the μ receptor-$K^+$ channel coupling.

Figure 10:
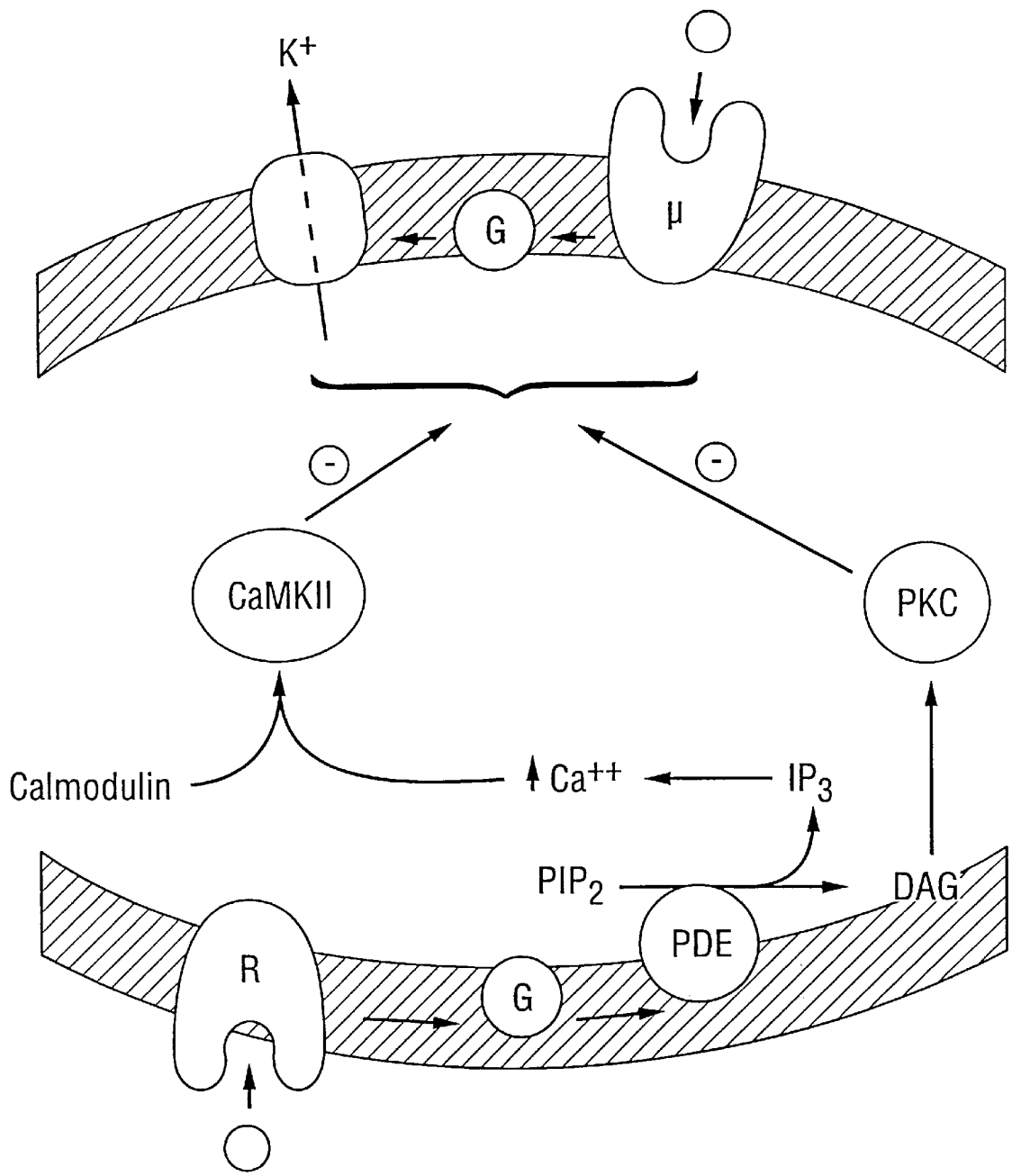
FIG. 10. Diagram Depicting the Coupling Between the μ Opioid Receptor and the G Protein-Activated $K^+$ Channel and the Effects of Protein Kinases The human μ opioid receptor and another type of surface receptor shown in the cell membrane depicted as μ and R, respectively. Open circles represent receptor ligands. Potassium channel shown with ionic efflux. Abbreviations for intracellular proteins: G, guanine nucleotide binding protein; AC, adenylyl cyclase; PKA, cAMP-dependent protein kinase; PKC, protein kinase C; CaMKII, multi-functional $Ca^{2+}$/calmodulin-dependent protein kinase; PDE, phosphodiesterase involved in PIP2 hydrolysis. Abbreviations for intracellular molecules: DAG, diacylglycerol; PIP2, phosphatidylinositol 4,5-bisphosphate; IP3, inositol 1,4,5-trisphosphate; ATP, adenosine triphosphate; cAMP, adenosine 3', 5'-cyclic monophosphate. Arrows pointing from second messenger molecules to proteins indicate a stimulatory influence. Arrows between proteins indicate either a stimulatory (+) or inhibitory (−) effect on interactions. Upward arrow adjacent to $Ca^{++}$ indicates an increase in intracellular calcium.
Figure 11A:
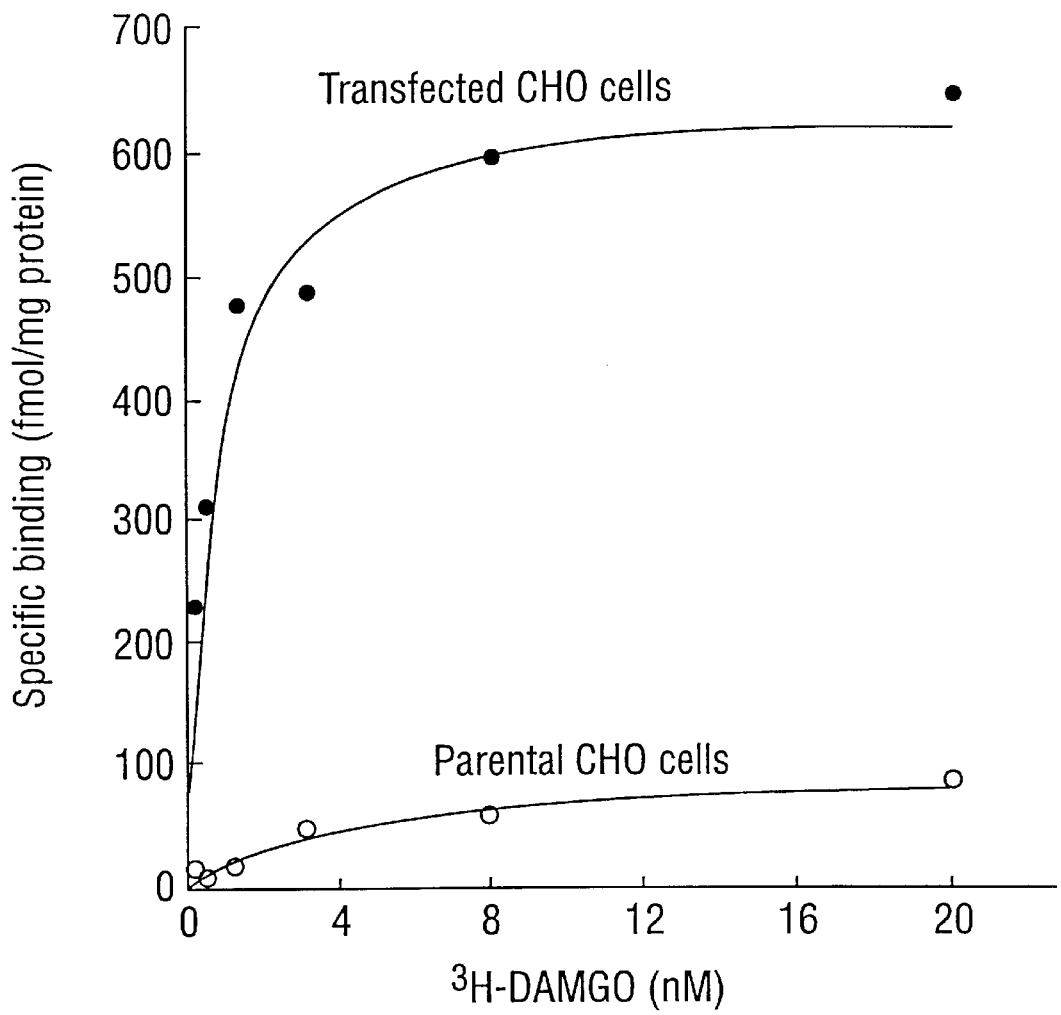
FIG. 11. Saturation binding of the transfected and the parental Chinese hamster ovary (CHO) cells. [$^3$H]DAMGO binding was performed using the membrane prepared from the transfected (●) or the nontransfected parental CHO cells (o). The data are representative of two saturation binding assays. Duplicate measurements were performed for each [$^3$H]DAMGO concentration used. The smooth lines represent the rectangular hyperbola fitting to the data. Inset: the Scatchard plot analysis of the data for the transfected cells.
Figure 11B:
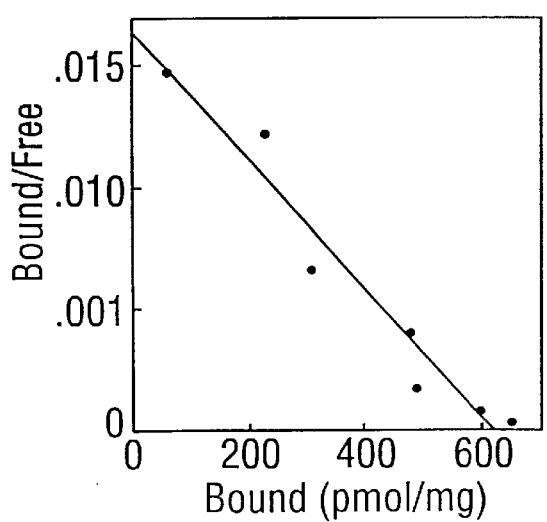
Figure 12:
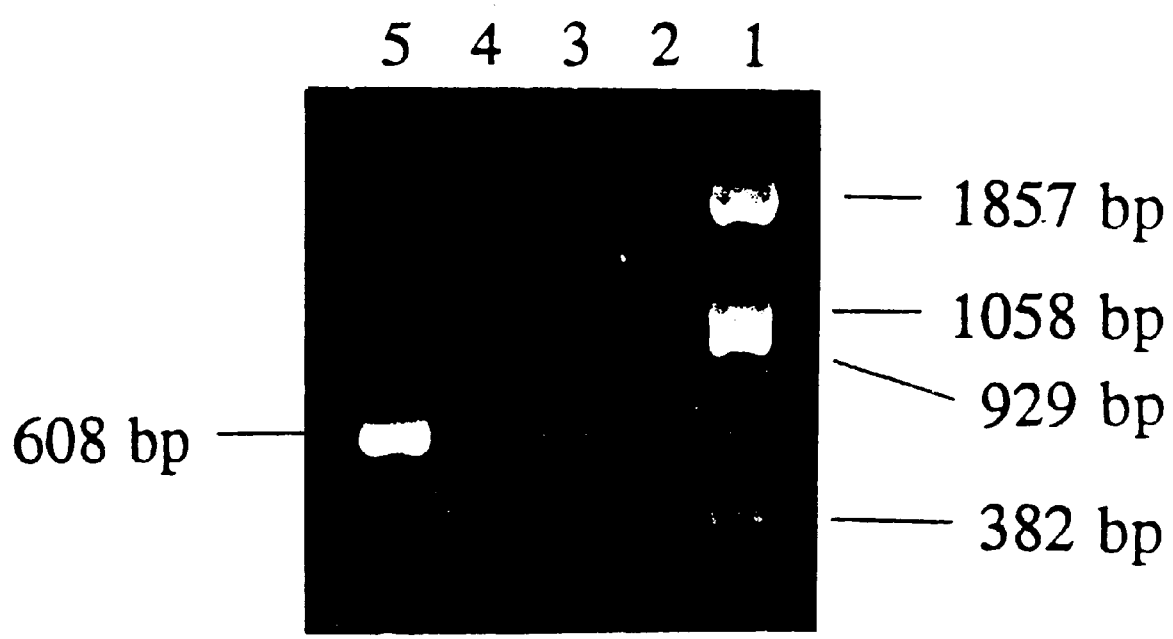
FIG. 12. RT-PCR with RNA isolated from parental and transfected CHO cells. Reverse transcription was performed with total RNA isolated from parental or transfected CHO cells. PCR was carried out with either the reverse-transcribed or the control DNA. The PCR products were separated on an agarose gel, and the gel was stained with ethidium bromide and photographed. Lanes are labeled as following: 1. pBR322 DNA digested with BstNI as the DNA size marker. 2. parental CHO cells; 3. transfected CHO cells; 4. water as a negative control; 5. cDNA clone of the rat μ opioid receptor as a positive control.
Figure 13:
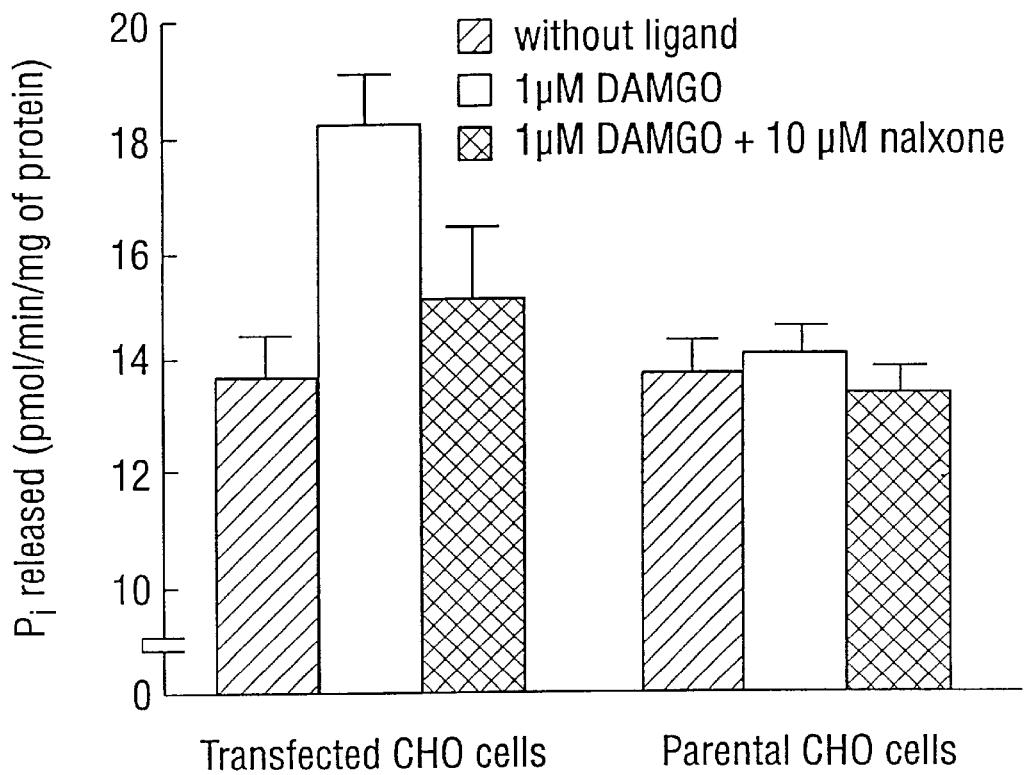
FIG. 13. GTPase activity of both transfected and parental CHO cells..[$^{32}$P]phosphate ($P_i$) release from [$^{32}$P]γ_GTP was measured in the membrane preparation of either the transfected or the nontransfected cells after treatment with opioid ligands as indicated. Data are representative of three experiments and are presented as mean±SEM (n=6 for each group). Analysis of variance shows that only the transfected cell with DAMGO treatment has significantly higher Pi release ($p<0.01$).
Figure 14:
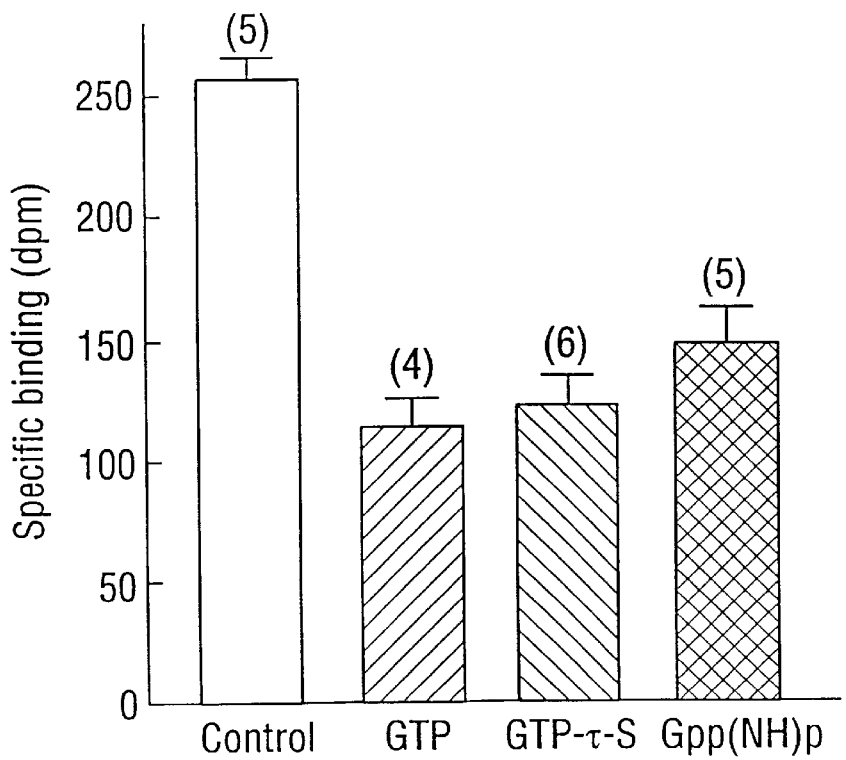
FIG. 14. DAMGO binding of the CHO cells expressing the μ receptor is sensitive to GTP and GTP analogues. Specific [$^3$H]DAMGO binding of the CHO cell membrane was measured without (control group) or with 10 μM GTP, 10 μM GTP-γ-S, or 10 μM Gpp(NH)p. Data are presented as mean±SEM. The bracket on the top of each bar indicates the sample number tested. Analysis of variance indicates significant difference between control group and each of the treatment groups (p<0.01).
Figure 15:
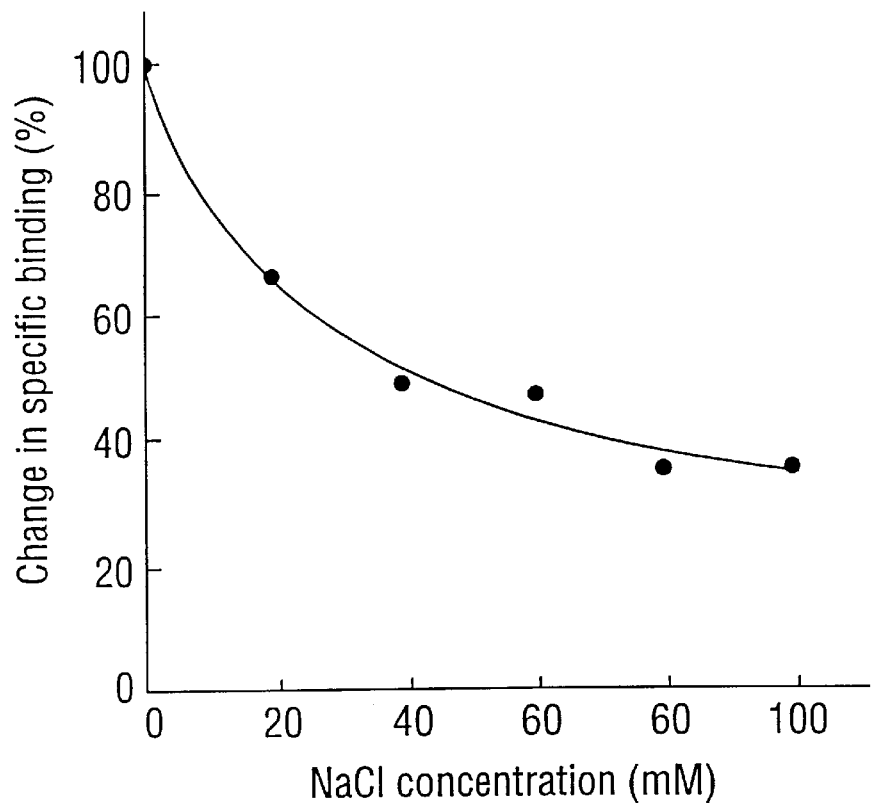
FIG. 15. Effect of sodium on agonist binding. [$^3$H] DAMGO binding to the cell membrane was measured in the presence of different NaCl concentration as indicated. Change in specific binding is shown as a percentage of the value of control (binding without NaCl). Each data point is the average of duplicate measurements with less than 5% variation between the measurements.
Figure 16:
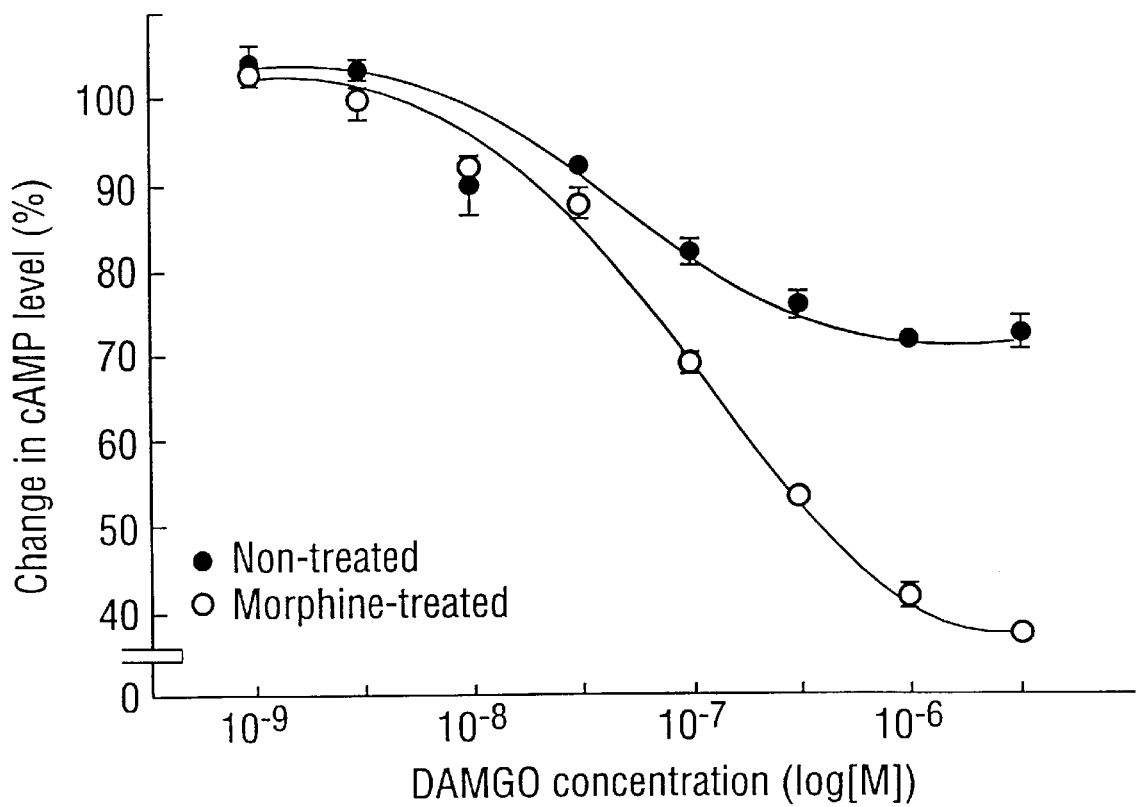
FIG. 16. Dose-dependent inhibition of intracellular cAMP level by DAMGO in naive and chronic morphine-treated CHO cells. The concentration of intracellular cAMP was measured after treatment with different amount of DAMGO in the naive transfected CHO cells (●) and the cells chronically treated with 1 $\mu$M morphine (o). Two micromolar of forskolin was used to elevate the basal level of cellular cAMP level. Triplicate measurements were performed for each DAMGO concentration tested. Data are shown as mean±SEM (n=6) and are expressed as percent changes in cAMP levels compared to the value without DAMGO treatment.
Figure 17:
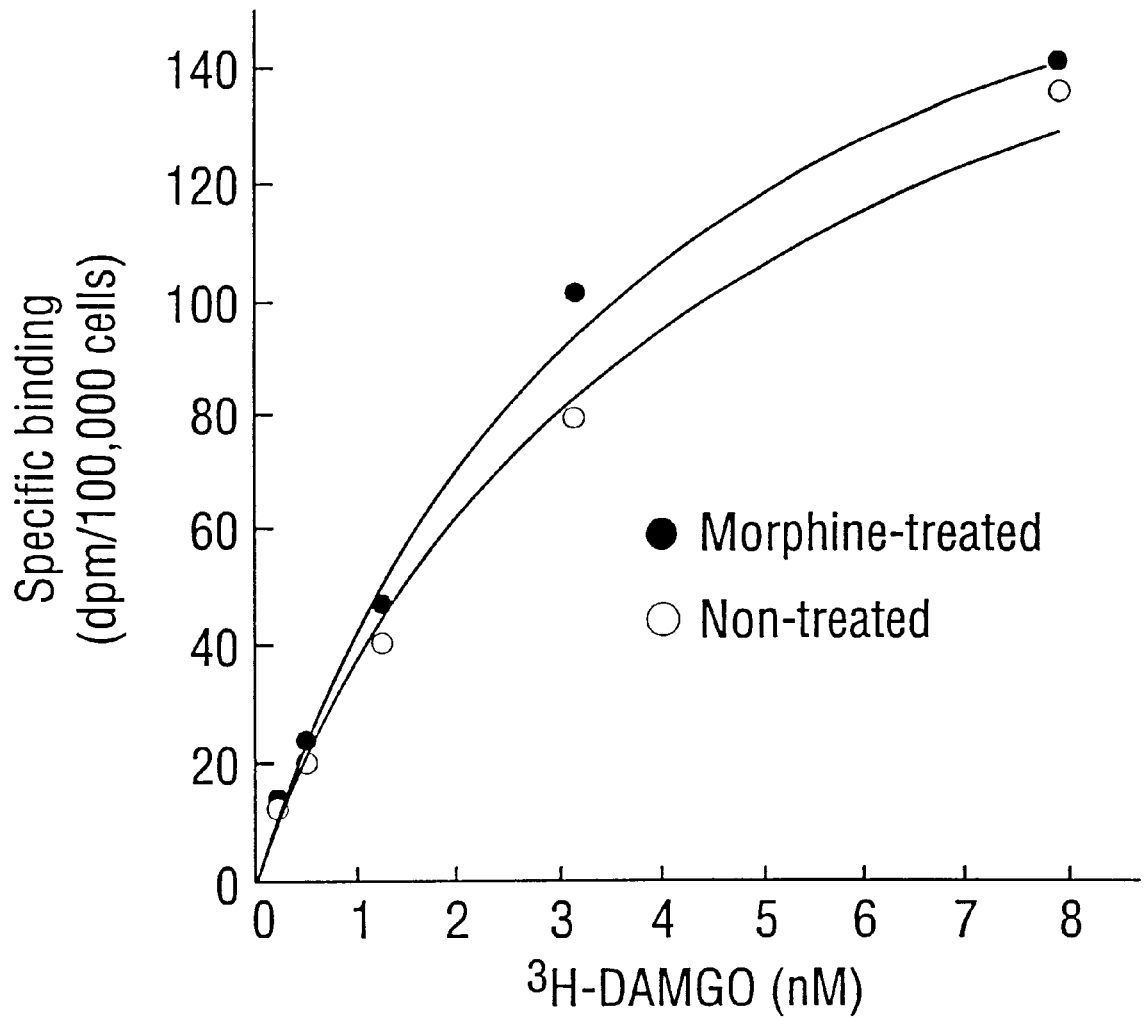
FIG. 17. Whole cell binding to [$^3$H]DAMGO in naive and chronic morphine-treated CHO cells. The whole cell binding with [$^3$H]DAMGO was presented as specific binding in non-treated cells (o) or the cells treated with 1 $\mu$M morphine for 24 hours (●). Duplicate measurements were performed for each [$^3$H]DAMGO concentration used. The measurement variation for each [$^3$H]DAMGO concentration is less than 5%.
Figure 19A:
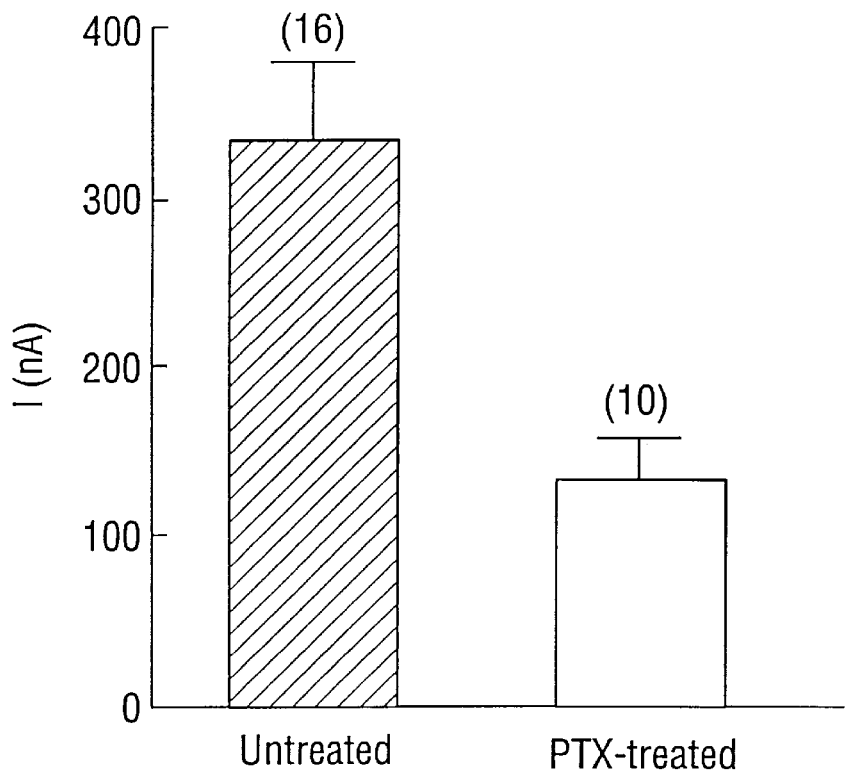
FIG. 19. Panels A and B of FIG. 19 show pertussis toxin (PTX) sensitivity of the $\mu$ opioid receptor-K$^+$ channel coupling. Oocytes injected with both the $\mu$receptor and the K$^+$ channel mRNAs were incubated with 0.5 $\mu$g/ml of PTX for 24 hours before recording. (A) DAMGO-induced currents at holding potential of −80 mV in untreated and PTX-treated oocytes. Data are presented as mean±S.E. with the sample size shown in parenthesis. Student t-test showed a significant difference (p<0.01). (B) Averaged I–V curves of the DAMGO-induced net currents from both groups.
Figure 19B:
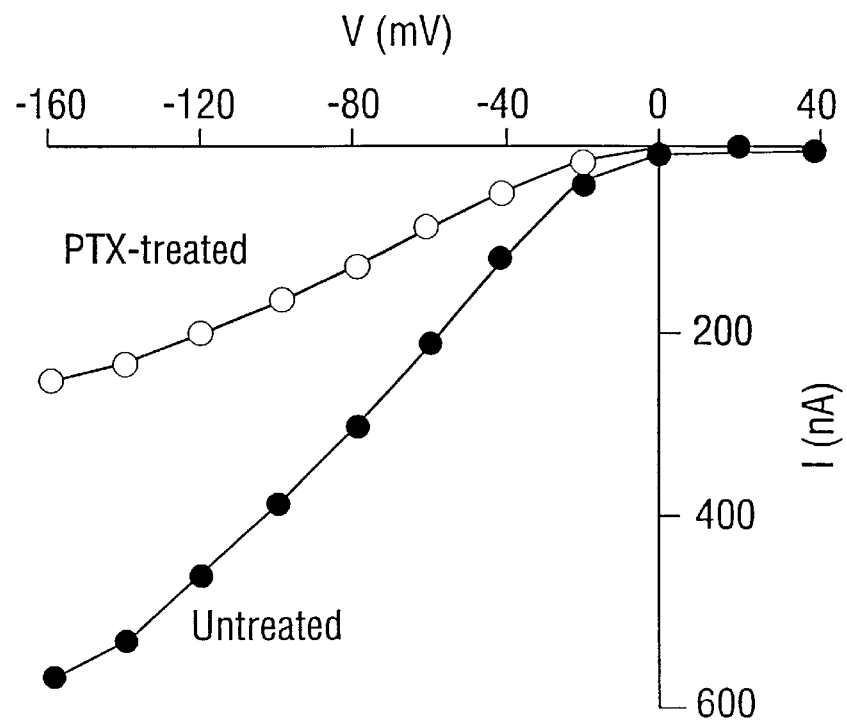
Figure 20A:
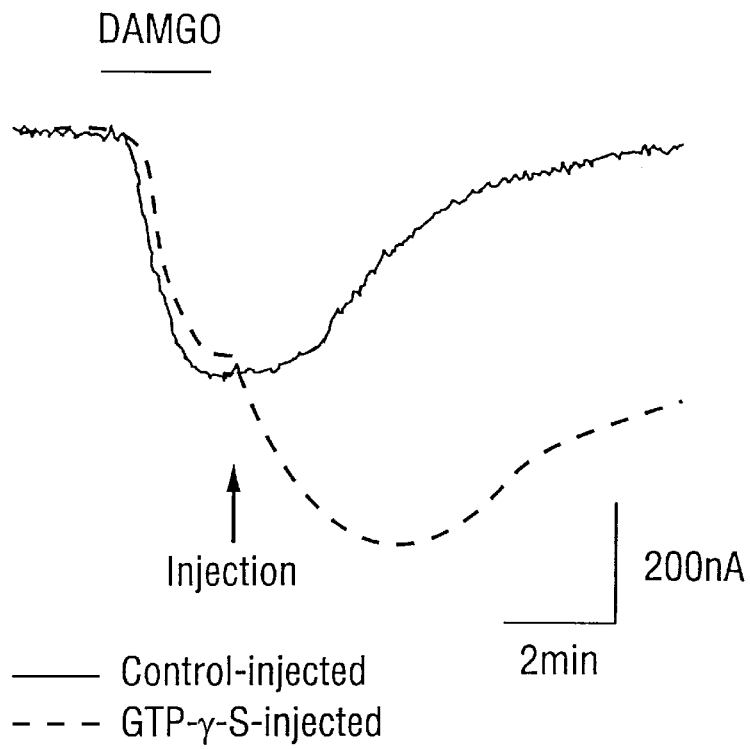
FIG. 20. Panels A and B of FIG. 20 show GTP-γ-S enhancement of the receptor-channel coupling. Fifty nanoliters of 1 mM GTP-γ-S or 10 mM Tris (pH 7.5, used as control) were injected after the membrane current induced by 1 $\mu$M of DAMGO reached plateau in oocytes injected with both the $\mu$ receptor and the K$^+$ channel mRNAs. (A) Two representative current traces recorded with a holding potential at −80 mV. Time point of injection was marked at the bottom of the traces. (B) Time course of the membrane current change after injection as compared to the value immediately before the injection. Data are the average of recordings from three oocytes in each group.
Figure 20B:
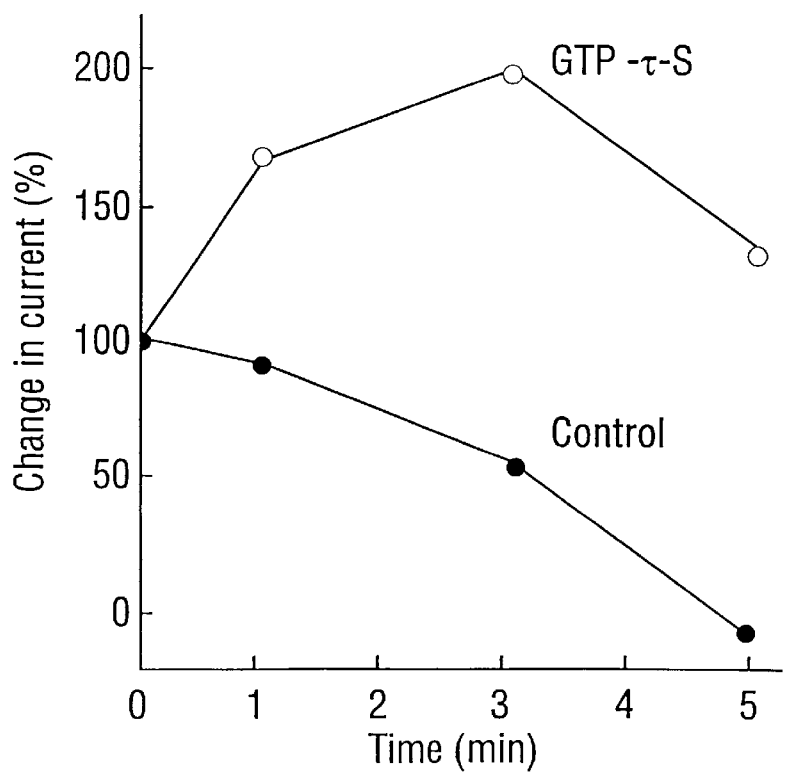
Figure 21A:
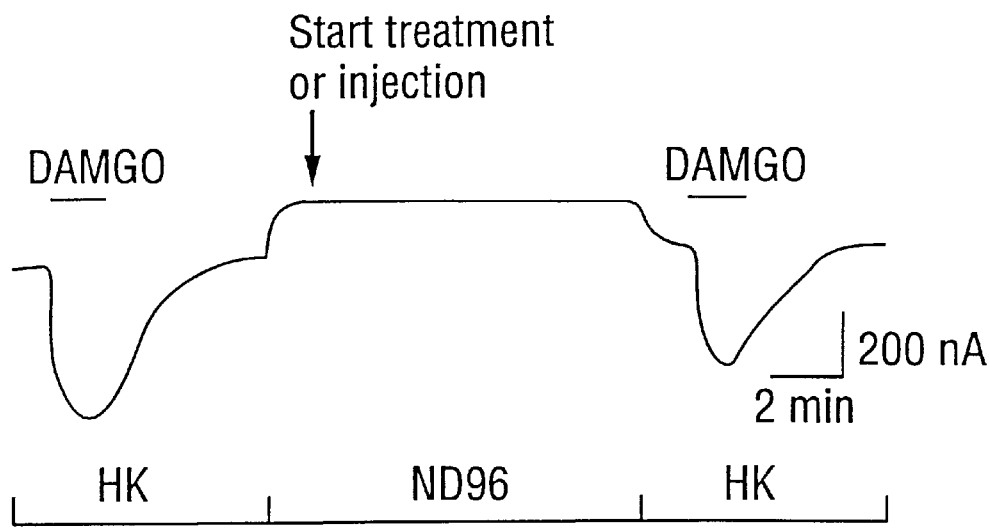
FIG. 21. Panels A and B of FIG. 21 show Differential regulation of the coupling by PKA and PKC. Membrane currents were recorded from oocytes injected with both the $\mu$ receptor and the K$^+$ channel mRNAs. (A) A representative current trace recorded in a oocyte at a holding potential of −80 mV illustrating the experimental protocol. The cell was bathed in a high potassium (HK) solution, and 1 $\mu$M of DAMGO was applied by superfusion to elicit the K$^+$ current. After the first DAMGO stimulation, the superfusate was switched to ND96 containing 6 mM of CaCl$_2$, and the oocyte was either untreated (as in this example) or subjected to drug treatment or enzyme injection (see below). The superfusate was then switched back to HK solution to record the second DAMGO-induced membrane current. (B) Relative response of the DAMGO-induced membrane currents from different treatment groups at a membrane potential of −80 mV. Data are expressed as the percentage of the peak current induced by second DAMGO stimulation over that of the first stimulation, and are presented as mean±S.E. (n=4). Treatment is labeled on the bottom of each bar. Result of variance analysis is shown as (**) with p<0.01 as compared to the untreated group. Different treatments used in this experiment are as follows: 8-CPT-cAMP, incubation with 1 mM of 8-CPT-cAMP for 10 min; PMA, incubation with 100 nM of PMA for 10 min; PKA, injection of the catalytic subunit of PKA (50 fmol/cell).
Figure 21B:
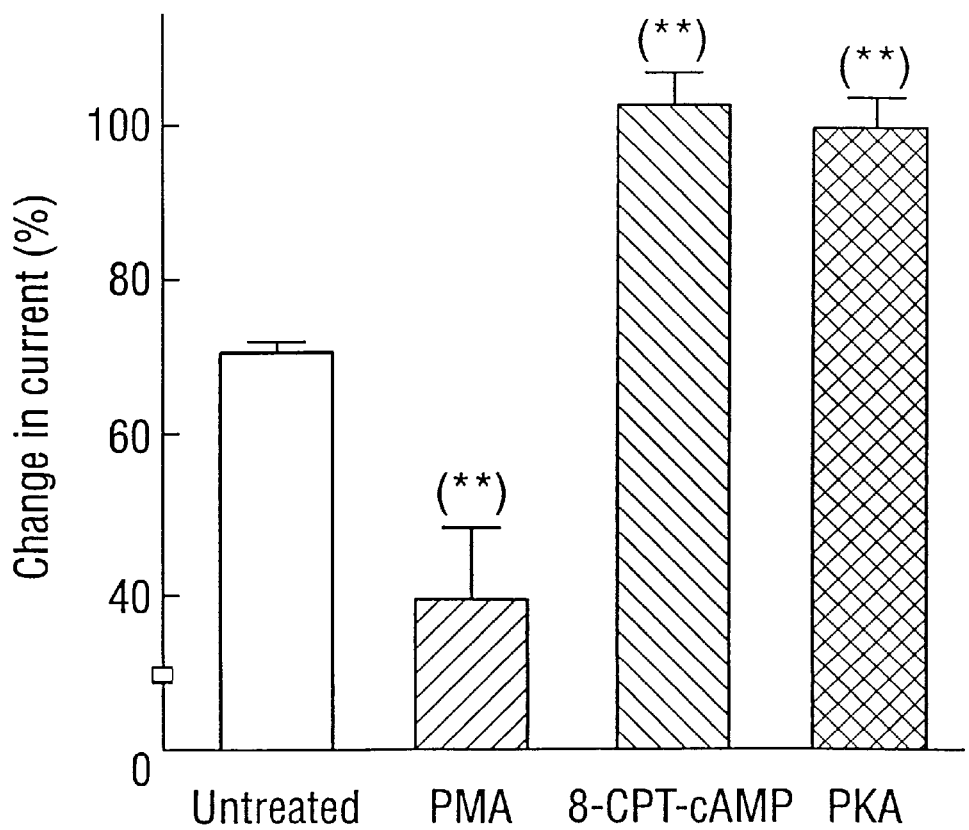
Figure 22:
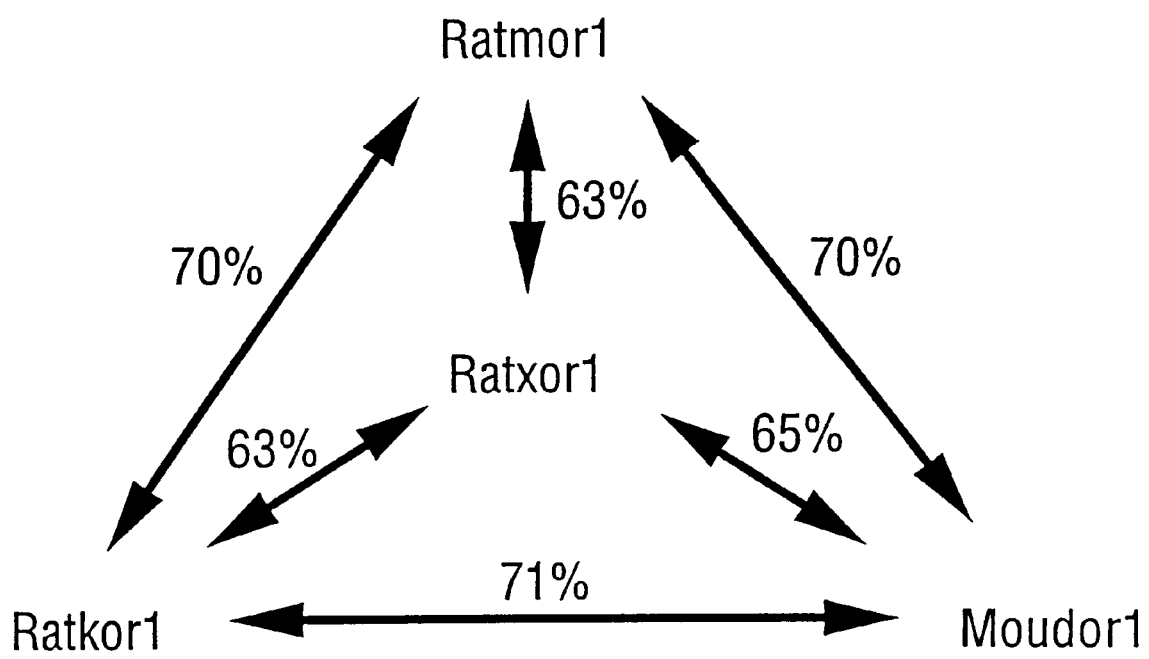
FIG. 22. Homology relationships of the putative opioid receptor with other three opioid receptors. Amino acid homology was calculated by taking into consideration of both identical and similar residues. Symbols used: ratmor1, the rat $\mu$ opioid receptor; ratkor1, the rat κ receptor; moudor1, the mouse δ receptor; ratxor1, the putative opioid receptor.
Figure 23B:
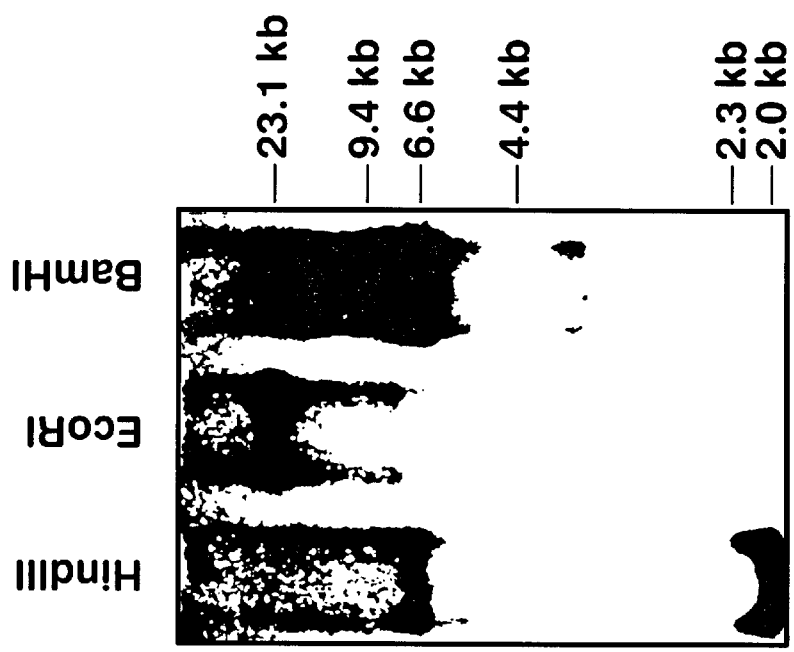
FIG. 23. Panels A and B of FIG. 23 show RNA tissue distribution and Southern blot analysis of the putative opioid receptor. (A) RNAs from eight different rat tissues are labeled above each lane. About 2 $\mu$g of polyA(+) RNA was used for each tissue. The sizes of the RNA size marker are labeled on the left side; (B) Genomic DNA Southern blot analysis. The restriction enzymes used to cut the rat genomic DNA are labeled above the corresponding lanes. λDNA digested with HindIII was used as the size marker with their sizes labeled on the left side.
Figure 23A:
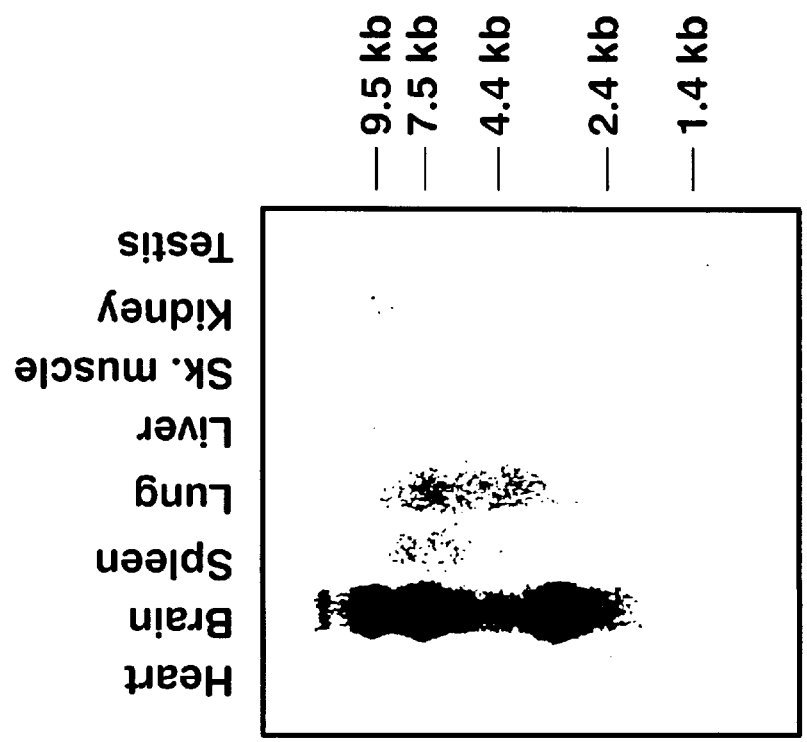
Figure 24A:
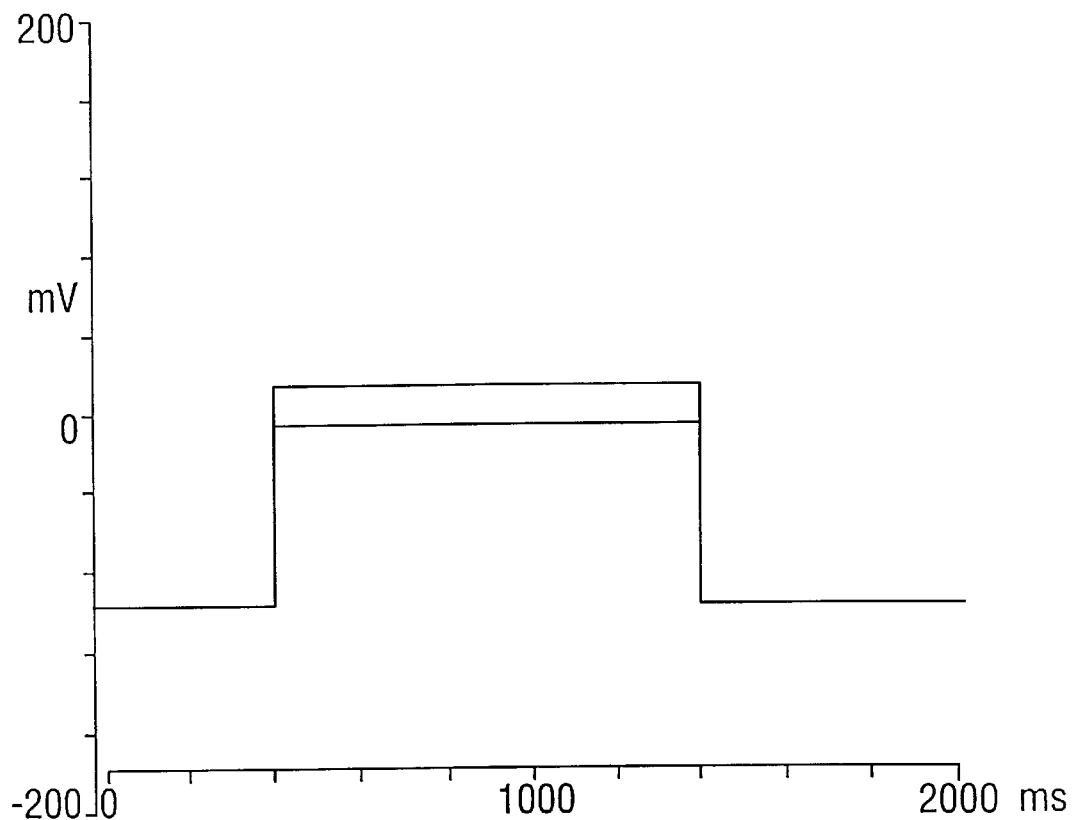
FIG. 24. Expression of a voltage-activated calcium channel. A voltage-activated calcium channel is expressed in Xenopus oocytes by microinjection of a plasmid containing the cDNA for the calcium channel (Soong et al. 1993). Two to three days after injection, oocytes are voltage-clamped and the calcium channel expression is measured using a step protocol. The calcium channel function is determined using a solution of 40 mM barium chloride and shown as barium current through the calcium channel. Top panel: command voltage steps from a holding potential of −100 mV to either −10 mV or +10 mV. Bottom panel: transient currents evoked by the voltage steps.
Figure 24B:
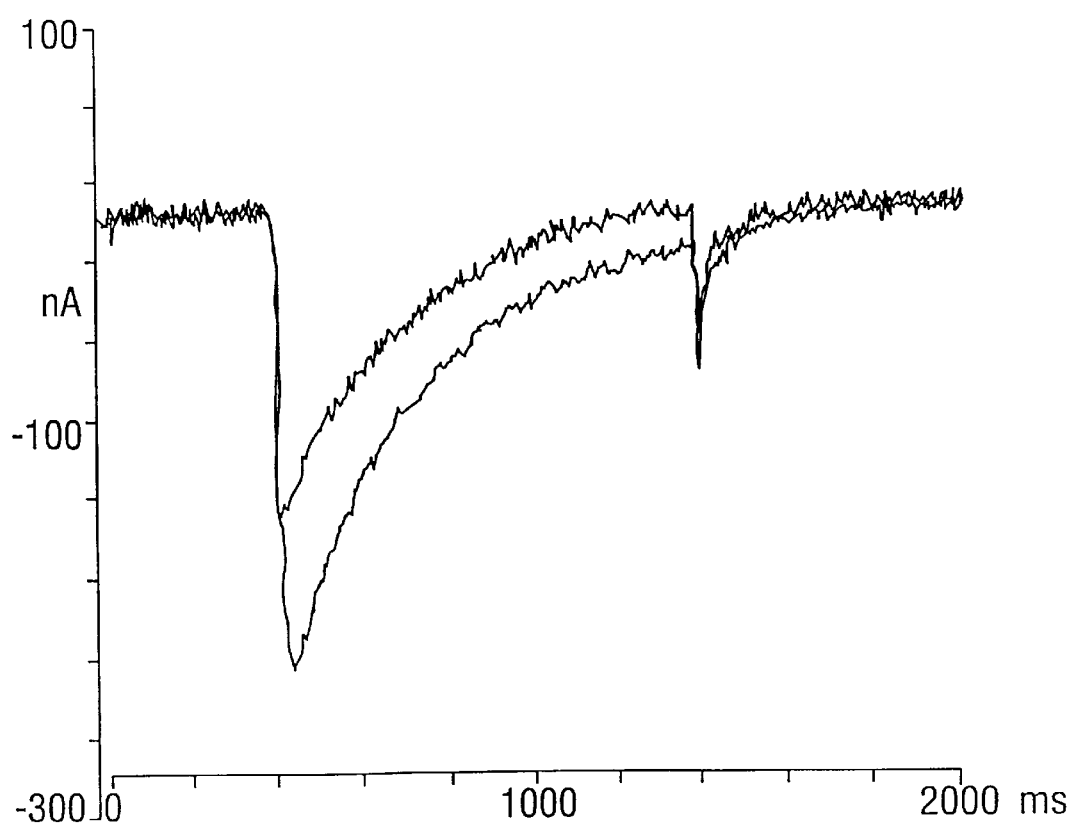
Figure 25:
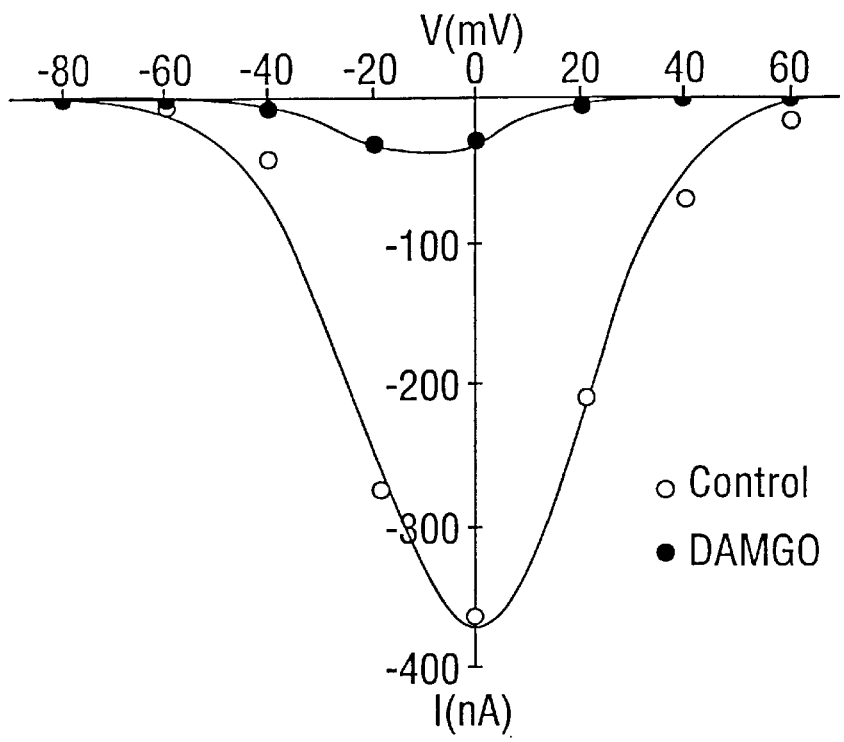
FIG. 25. Current-voltage (I–V) relationship and the effect of mu opioid receptor activation. Oocytes are injected with both a voltage-activated calcium channel plasmid and a mu opioid receptor plasmid. Peak barium currents (see FIG. 24) are measured and are plotted against the corresponding voltage. Open circles: I–V relationship in an oocyte without any treatment. Solid circles: I–V relationship in the same oocyte after the cell is treated with 1 $\mu$M DAMGO for 5 min, indicating a pronounced suppression of the calcium channel function by the activation of mu opioid receptor.
Figure 26:
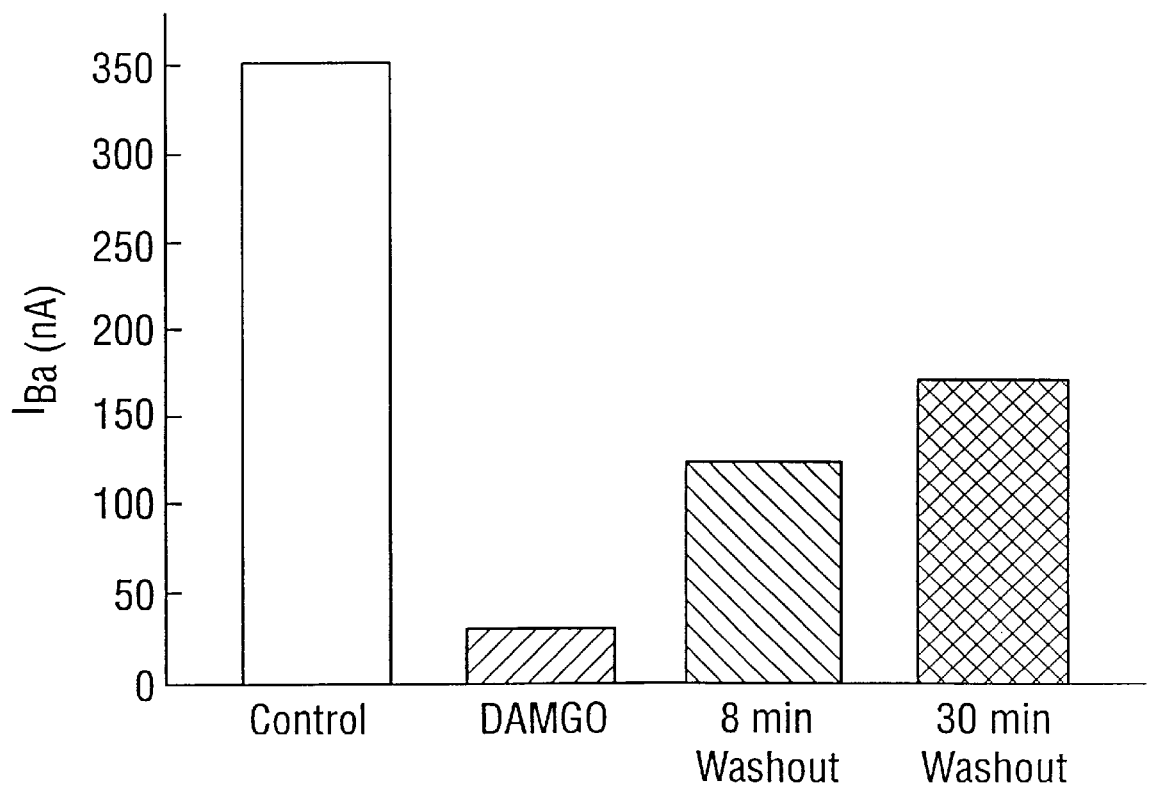
FIG. 26. Time-dependent effect of mu opioid receptor activation on maximum calcium channel activity. The maximum barium current (see FIG. 25) at a given time is indicated. Control: maximum current from an oocyte without any treatment. DAMGO: maximum current from the same oocyte after 5 min treatment with 1 µM DAMGO. 8 min washout: maximum current after DAMGO is washed out for 8 min. 30 min washout: after DAMGO is washed out for 30 min.

Both PKC and CaM kinase II are cellular effectors of a G protein-activated phosphodiesterase, phospholipase C (PLC). The activation of PLC causes the production of diacylglycerol (DAG) and inositol 1,4,5-trisphosphate (IP3), two intracellular second messenger molecules which represent a bifurcation in the signal transduction pathway (Berridge, 1987). Whereas DAG activates PKC, IP3 triggers $Ca^{2+}$ release from intracellular stores. Since CaM kinase II is activated by physiological elevations in cytosolic $Ca^{2+}$ levels (MacNicol and Schulman, 1992b; Schulman and Hanson, 1993), stimulation of receptors linked to PLC may cause activation of both PKC and CaM kinase (FIG. 10). Other neurotransmitter receptors which belong to the family of G protein-coupled receptors influence the steady-state levels of cAMP by either stimulating or inhibiting the activity of adenylyl cyclase as is the case for the β-adrenergic and opioid receptors, respectively (FIG. 10). The widespread distribution of many G protein-coupled receptors suggests that some may be found within similar structures of the brain. In fact, in situ hybridization has shown that messages encoding receptors that use either similar (Lester et al., 1993) or different (Weiner et al., 1990) signaling pathways do co-exist within the same cell. These data suggest that PLC-coupled receptors may potentiate the process of desensitization that is observed as a reduction in receptor-channel coupling upon repeated stimulation of the μ opioid receptor (FIG. 10). Thus, it is plausible that signal transduction mechanisms may affect one another, when the receptors to which they couple are present on the same neuron.

Since opioid receptor activation has been shown to affect cAMP levels, another important kinase in the regulation of opioid receptor activity is protein kinase A (PKA). Opioid receptor activation inhibits adenylyl cyclase, resulting in decreased levels of cAMP and a reduction in basal PKA activity. The inventor has previously demonstrated that an increased PKA activity, either by injection of the catalytic subunit of PKA into the cell or by exposing the cell to a membrane-permeable cAMP-analogue, eliminated desensitization of the μ receptor-$K^+$ channel coupling (Chen and Yu, 1994). Thus, agents that activate PKA would function antagonistically in relation to the μ opioid receptor-mediated channel activity. This presents an interesting control loop whereby the activity of the channel is subject to negative feedback inhibition modulated by the μ opioid receptor via a decrease in PKA activity (FIG. 10).

The inventor has attempted to investigate the role of each kinase in the mechanisms involved in acute desensitization. FIG. 10 depicts the individual effects of these kinases on opioid receptor-mediated $K^+$ channel activity. Although precedents exist for their acting independently, these kinases are subject to "cross-talk" which is the ability of one signal transduction mechanism to affect another (MacNicol and Schulman, 1992a; Yamakawa et al., 1992). Taken together, these data suggest that an intricate network of modulation among receptors, G protein effectors, and protein kinases may exist. It should be noted that although each element in the model has been demonstrated in oocytes and/or neurons, the complete scheme has not yet been confirmed with respect to the cross-modulation that may occur among multiple receptor types. With the cloning of the μ opioid receptor and the $K^+$ channel, future efforts will focus on identifying other key elements involved in this modulatory network. By testing this model, what remains to be discovered will further understanding of the molecular mechanisms that underlie the regulation of receptor-mediated neuronal activity.

Example V: Isolation of Polyclonal Antibodies Immunoreactive with Mu Opioid Receptor Polypeptide Researchers at University of Minnesota, using information provided to them by the inventor on the mu opioid receptor sequence, generated polyclonal antibodies inunnunoreactive with a mu opioid receptor polypeptide. A standard method was used which entailed:

1) synthesizing a 15-amino acid peptide corresponding to the rat mu opioid receptor C terminal end (peptide sequence: NHQLENLEAETAPLP (SEQ ID NO: 9; Asn His Gln Leu Glu Asn Leu Glu Ala Glu Thr Ala Pro Leu Pro according to 37 C.F.R. § 1.822).
2) conjugating with glutaraldehyde to a carrier protein;
3) immunizing rabbits; and
4) collecting serum from immunized animals.

The inventor used this antibody to perform Western blots. These blots demonstrated that with the mu opioid receptor cDNA clone transfected into mammalian cells, the opioid receptor polypeptide can be generated.

A standard procedure was used for Western blot. Membrane proteins were prepared from various cell sources, including parental and transfected (with the mu opioid receptor cDNA clone) Chinese hamster ovary cells, parental and transfected PC12 cells, parental and transfected $GH_3$ cells, human neuroblastoma cell line SH-SY5Y that has endogenous human mu and delta opioid receptors (Yu et al., 1986), and neuroblastoma-glioma hybrid cell line NG108-15 that has only delta, but not mu, opioid receptor (Evans et al., 1992; Kieffer et al., 1992). Aliquots of membrane proteins (20–50 μg) were run in SDS-polyacrylamide gels and blotted onto nitrocellulose papers by the standard protocol for electroblotting. The membranes were stained with diluted primary antisera (1:20,000 dilution) and then with secondary antibody, and the bands were visualized on X-ray films.

This antibody recognized a 55 kD protein. The 55 kD protein recognized by this antibody is indeed the mu opioid receptor. This conclusion is verified by many lines of evidence: the size of the protein agreed with the estimated size of the mu opioid receptor based on the cDNA cloning; the protein was present only in transfected CHO, PC12 and $GH_3$ cells and not in non-transfected parental controls; this protein was also detected in the SH-SY5Y cells known to contain the mu opioid receptor, and was not seen in NG108-15 cells that only contain the delta opioid receptor; and using G protein-specific antibodies from Dr. David Manning at University of Pennsylvania (Mumby et al., 1986; Carlson et al., 1989; Law et al., 1991), the inventor performed imnunoprecipitation of receptor-G protein complex. The inventor demonstrated that the immunoprecipitate displays the mu opioid receptor binding activities, and the anti-mu antibody also identified the same 55 kD protein in immunoprecipitate.

These results indicate that the antibody is selective for the mu opioid receptor and is not cross-reactive with NG-108 cell's delta receptor that shares sequence homology and structural similarity with the mu opioid receptor.

Example VI: Sequence Difference in the Human Mu Opioid Receptor

The human mu opioid receptor cloned by the inventor confers high affinity binding to opioid alkaloids with abuse potential, as well as endogenous opioid peptides. For example, morphine and methadone have $K_i$ values of 3.6 nM and 3.7 nM, respectively. Also, Metenkephalin, β-endorphin, and dynorphin A (1-17) display $K_i$ values of 2.2 nM, 1.8 nM, and 1.6 nM, respectively.

It is of particular interest that dynorphin A (1-17) displays nanomolar affinity at this mu receptor, because a recent publication, following the same methodology described in this invention, also reported the cloning of a human mu receptor (Wang et al. 1994), with virtually identical pharmacology to the results found by the inventor except that for dynorphin A (1-17). While the mu receptor of the present invention has a $K_i$ value of 1.6±0.3 nM, the clone isolated by Wang et al. has a $K_i$ value of 284±110 nM (1994)—a difference of over 100-fold. When the two sequences are compared, there is only a single-base difference at the nucleotide no. 151 (corresponding to codon no. 51 in the amino acid sequence), resulting in the substitution of an aspartate residue in the clone of the present invention to an asparagine—a net loss of one negative charge. See SEQ ID NOS: 7 and 8.

Dynorphin A has the highest affinity at the kappa opioid receptor sites (Goldstein, 1987), and is thus considered a kappa agonist (Chavkin et al. 1982). However, while it binds at the kappa receptors with subnanomolar affinity, it does display reasonably good binding at the mu receptors, with an affinity value in the nanomolar range (Goldstein, 1987; Pasternak, 1993); thus it may also interact with dynorphin A in the body (Akil et al. 1984). Detailed studies of dynorphin A binding in the human brain are very limited. There are some reports, however, on comparative studies using rodent and bovine brain membranes (Pasternak, 1993). For example, using guinea pig brain membranes, it has been shown that dynorphin A (1-17) can displace radiolabeled PL-17, a mu-selective ligand, with a 5 nM affinity (Kawasaki et al. 1990). In another study, dynorphin A (1-17) was found to displace radiolabeled DAMGO, another mu-selective ligand, with 3 nM affinity (Vaughn and Taylor, 1989). When a distinction is made with regard to the putative subtypes for the mu receptor, the $K_i$ values for dynorphin A (1-17) are given as 0.7 nM at $Mu_1$ site and as 2.2 nM at the $Mu_2$ site (Clark et al. 1988). When the cloned murine opioid receptors were compared side-by-side for their ligand binding properties, it was found that dynorphin A (1-17) was very potent in displacing $^3$H-U-69593 binding to the mouse kappa receptor at 0.5 nM affinity, and showed lower affinity at the rat mu receptor with an affinity of 32 nM (Raynor et al. 1994). It appears that species differences may exist regarding the affinity of dynorphin A (1-17) binding at the mu receptor, and clearly more detailed studies are needed to characterize this property, especially for the mu receptor in humans, which may contain considerable sequence polymorphism since experimental laboratory animals are usually inbred.

The single-base difference between the cDNA isolated by the inventor and by Wang et al. may serve as an example of sequence polymorphism in humans, since these two clones were from two independent sources—the inventor used a cDNA library from Clontech, whereas Wang et al. used a cDNA library from Stratagene (Wang et al. 1994a). Neither clone was obtained by PCR, therefore the possibility of PCR error is not a concern. Since both clones give functional receptors, they may represent two different alleles for the mu receptor gene in humans. In an effort to evaluate the prevalence of alleles, two oligonucleotides that flank a region in the receptor cDNA including codon no. 51 were synthesized and used as PCR primers to amplify the mu receptor region containing codon no. 51. DNA samples from nine individuals, three of African-American heritage and six of Caucasian, were used as PCR templates, and the PCR products were analyzed by DNA sequencing. These samples all contained the same codon no. 51 as that in the inventor's clone, predicting an aspartate amino acid residue at this position. The number of individuals tested was small, therefore no conclusion can be drawn regarding the prevalence of allele frequency. This pilot study does suggest, however, that the mu receptor allele bearing an aspartate codon at no. 51 position may be relatively common. A definitive estimation of allele frequency is, however, still not known. It should be pointed out that since the cDNA clone disclosed herein and containing the same codon gave a mu receptor with nanomolar affinity for dynorphin A (1-17), the possibility of dynorphin A acting at the mu receptor in humans, in addition to the kappa receptor, needs to be examined.

Another implication of the codon no. 51 polymorphism is that this position resides in the N-terminal portion of the mu receptor, a region previously considered to be unrelated to the ligand binding capacity of the receptor. This suggests that screening for naturally occurring polymorphisms offers an innovative approach to identify critical domains in receptor function. Using the strategy employed in examining codon no. 51 variations, the entire mu receptor coding sequence can be readily characterized from each individuals, thus providing detailed information on sequence polymorphisms in this receptor gene.

Example VII: Functional Coupling of a Mu Opioid Receptor to G Proteins and Adenylyl Cyclase: Modulation by Chronic Morphine Treatment The inventor has also used a cloned $\mu$ opioid receptor to study its coupling to signal transduction pathways and its involvement in the morphine-induced opioid dependence in stably transfected Chinese hamster ovary (CHO) cells. Membrane binding assays with a $\mu$-selective agonist [$^3$H] DAMGO showed that one cell line expresses a high level of $\mu$ opioid receptors with a $B_{max}$ of ~630 fmol/mg membrane protein and a $K_d$ of 0.47 nM for DAMGO. Reverse transcription PCR using $\mu$ opioid receptor-specific oligonucleotides confirmed the expression of the receptor in the CHO cells. Stimulation of the transfected cells with DAMGO led to an increase in the low $K_m$ GTPase activity, indicative of activation of guanine nucleotide regulatory proteins (G proteins), and this effect was blocked by the opioid antagonist naloxone. In addition, binding of the $\mu$ opioid receptor to DAMGO was affected by GTP and nonhydrolizable GTP analogues, Gp(NH)pp and GTP-γ-S. These results suggest a functional coupling between the $\mu$ opioid receptor and G proteins. Furthermore, DAMGO treatment of the cells produced a dose-dependent inhibition of the intracellular cAMP level, with an $EC_{50}$ value of approximately 30 nM. Chronic treatment of the cells with morphine not only elevated the basal and forskolin-stimulated cAMP levels after morphine withdrawal, but also increased the extent of the DAMGO-induced reduction of intracellular cAMP levels. The whole cell binding assay with [$^3$H]DAMGO, on the other hand, did not detect receptor down-regulation after chronic morphine treatment. These results suggest that chronic morphine treatment may trigger a compensatory mechanism in cellular signaling pathways to offset the inhibitory input from the $\mu$ receptor without down-regulation of the surface receptor number, and that withdrawal of chronic inhibition leads to elevated activities of adenylyl cyclase to provide a basis for system sensitization. The functional coupling of the cloned $\mu$ receptor to G proteins and adenylyl cyclase in CHO cells as well as the cellular changes after chronic morphine treatment indicate that this cell line is useful for studies of the molecular mechanisms underlying the signal transduction and other physiological effects of the $\mu$ opioid receptor.

A. Experimental Procedures

Materials: CHO cells were from the American Type Culture Collection (Rockville, Md., USA). [$^3$H]DAMGO (38 Ci/mmol) was from the National Institute on Drug Abuse. [$^{32}$P](γ)GTP (10 Ci/mmol) was from Amersham (Arlington Heights, Ill., USA). DAMGO ([D-Ala$^2$,MePhe4, Glyol5]enkephalin) was from Bachem (Torrance, Calif., USA). All other chemicals were from Sigma (St. Louis, Mo., USA).

Cell transfection: A plasmid containing a 1.4 kb cDNA for the rat $\mu$ opioid receptor in a mammalian expression vector pRc/CMV has been described (Chen et al., 1993a). CHO cells growing in HAM's F-12 medium supplemented with 10% fatal calf serum were transfected with the supercoiled plasmid DNA using a standard calcium phosphate procedure. The neomycin resistant transfectants were selected by G418 (500 μg/ml) starting one day after transfection. The selection medium was changed every 2–3 days until drug-resistant colonies were formed. Individual colonies were picked and replated after trypsin dissociation. A second round of selection was performed to isolate clonal derivatives. Cells thus isolated were grown up in 100 mM diameter-plate and aliquots of the cells were frozen in liquid nitrogen for long term storage. One clone was isolated from 30 colonies by a preliminary binding assay with [$^3$H] diprenorphine and was subjected to further characterization described in this report.

Membrane preparation: CHO cells were washed in HBSS (Hanks' balanced salt solution), harvested by scraping from the plates with a rubber policeman and centrifuged. Cell pellets were resuspended in 50 mM Tris (pH7.4) and lysed using a Dounce homogenizer. The homogenate was centrifuged at 1,000 g for 10 min and the supernatant was saved. The pellet was resuspended in the same buffer, homogenized and centrifuged as before. The supernatant was combined and centrifuged at 15,000 g for 20 min. The supernatant was discarded, and the pellet was washed once with 50 mM Tris (pH7.4). Membrane pellets were resuspended in 50 mM Tris (pH 7.4) and frozen at −70° C. until use. Protein concentration was determined using γ-globulin as standard.

Membrane and whole cell binding assays: Membrane binding assays were performed in 50 mM Tris (pH 7.4) and 0.2% bovine serum albumin at room temperature for 90 min. Ten microgram of membrane protein was used in each binding assay. A range of 0.2–20 nM of [$^3$H]DAMGO was used in saturation binding and 0.5 nM was used to determine the effect of GTP analogues on DAMGO binding. Binding was terminated by vacuum filtration through Whatman GF/B filters pretreated with 1% polyethylenimine. The filters were washed with 5 ml of ice-cold 50 mM Tris (pH 7.4) for three times before scintillation counting. Specific binding was calculated by subtracting the binding in the presence of 10 μM naloxone from the total binding. For whole cell binding experiments, cells were scraped from the plates with a rubber policeman and washed with PBS buffer (phosphate-buffered saline, pH 7.2). The cells were directly used in binding assays in a half-strength PBS buffer and 0.1% of BSA under the same conditions for the membrane binding assays.

Reverse transcription and PCR (RT-PCR): Total RNA was prepared from both the parental and the transfected CHO cells. Reverse transcription was performed with 2 μg of total RNA and random hexomers in the presence of 50 mM Tris (pH 7.5), 5 mM MgCl$_2$ and 12 units of AMV reverse transcriptase at 37° C. for 90 minutes. The cDNA product was directly used in PCR with two oligonucleotide primers for the rat μ opioid receptor (Chen et al., 1993a): TGAAGACTGCCACCAACA (SEQ ID NO: 10) and GATGACGTAGATGTGGAT (SEQ ID NO: 11). Forty cycles of PCR were performed at 94° C. for 5 sec, 55° C. for 10 sec and 75° C. for 40 sec in an air cycler (Idaho Technology). PCR products were separated in a 1.6% agarose gel and visualized by staining with ethidium bromide.

GTPase assay: The low K$_m$ GTPase activity was determined by the method of Koski and Klee (Koshi and Klee, 1981) with minor modification. Release of [$^{32}$P] was measured in 0.5 μM [$^{32}$P](γ)GTP, 50 mM NaCl, 2.5 mM MgCl$_2$, 30 mM Tris (pH7.4), 1 mM dithiothreitol, 0.5 mM p[NH]ppA, 0.5 mM ATP, 0.5 mM Ouabain, 5 mM of creatine phosphate, and 5 units of creatine phosphokinase in a total volume of 200 μl. Two to three micrograms of membrane proteins were used in each assay. The reaction was performed at 37° C. for 10 min and stopped by addition of 1 ml 5% (w/v) charcoal suspended in 20 mM of phosphoric acid. After centrifugation in a bench-top microcentrifuge for 10 min, the radioactivity was measured using 200 μl aliquot of the supernatant with 5 ml of scintillation solution (CytoScint from ICN, Costa Mesa, Calif., USA). The low K$_m$ GTPase activity was calculated by subtracting the Pi released in the presence of 50 μM of GTP from the total Pi.

Cyclic AMP assay: Transfected CHO cells were harvested from the plates and resuspended in HAM's F12 medium without serum. Cells were treated with the testing compounds either alone or in the presence of 2 μM of forskolin and 1 mM of 3-isobutyl-1-methylzanthine at 37° C. for 10 min. The reaction was terminated by addition of 0.5 volumes of 0.1 N HCl. The mixture was boiled for 5 min, and centrifuged in a bench-top microcentrifuge for 10 min. The supernatant was transferred to a new tube and dried under vacuum. The cAMP content was determined by a nonacetylated protocol using the radioimmunoassay kit from DuPont/NEN (Billerica, Mass., USA).

B. Results

Stable transfection of the rat μ opioid receptor in CHO cells: In order to establish mammalian cell lines that express the cloned rat μ opioid receptor, CHO cells were transfected with the cDNA clone of the receptor in a mammalian cell-expression vector under the control of the human cytomegalovirus promoter. Thirty clones surviving neomycin selection were characterized by binding assays with [$^3$H]diprenorphine, a non-selective opioid ligand that binds to all opioid receptors. One of the colonies showed a high level of diprenorphine binding and was used for further analysis. Saturation binding with the μ-selective agonist [$^3$H]DAMGO indicates that this cell line expressed the μ opioid receptor at a B$_{max}$ of ~630 fmol/mg membrane protein and a K$_d$ of 0.47 μM for DAMGO. The K$_d$ value for DAMGO derived from the saturation assay is comparable to the K$_i$ value calculated from displacement binding assays in transient expression in COS-7 cells (Chen et al., 1993). Parental CHO cells only had residual binding to [$^3$H]DAMGO, suggesting that CHO cells contain negligible levels of endogenous opioid receptors as compared to the exogenously expressed μ opioid receptor.

RT-PCR with RNA from transfected cells: To further confirm the expression of the cloned μ opioid receptor in CHO cells, RT-PCR was performed with the total RNA isolated from both the parental and the transfected CHO cells, using a pair of oligonucleotide primers specific for the μ receptor sequence. A PCR fragment with the expected length of 608 base pairs was obtained from the transfected cells, whereas no PCR fragment was visible from the parental CHO cells. Also shown are both the positive and the negative controls used in the PCR, i.e. the μ opioid receptor cDNA clone and water as the PCR templates, respectively. These results indicate that the transfected CHO cells contain the mRNA for the μ opioid receptor whereas the parental CHO cells do not, further suggesting that there is no endogenous μ receptors in the untransfected CHO cells.

The cloned μ opioid receptor is functionally coupled to G proteins: Molecular cloning of the rat μ opioid receptor showed that it shares the structural feature of seven transmembrane hydrophobic domains with most G protein-coupled receptors (Chen et al., 1993), indicative of this receptor coupling to heterotrimeric GTP-binding proteins (G proteins) as their mediator for signal transduction. Previous studies using cells lines that constitutively express endogenous opioid receptors also suggest that opioid receptors are coupled to G proteins. To test the G protein coupling of the cloned μ opioid receptor, the low K$_m$ GTPase activity was measured in the stably transfected CHO cells. Treatment of the transfected cells with 1 μM of DAMGO elevated the GTPase activity by 33%, and the stimulation was blocked by 10 μM of naloxone, an opioid antagonist. In the untransfected parental CHO cells, on the other hand, the GTPase activity was not affected by DAMGO treatment. Because the α subunit of G proteins possesses an intrinsic GTPase activity and an increase in the low $K_m$ GTPase activity is indicative of G protein activation, these results suggest that the cloned μ opioid receptor is functionally coupled to the endogenous G proteins in CHO cells.

The coupling of the μ opioid receptor to G proteins was further studied using GTP and GTP analogues in the [³H] DAMGO binding assay, since previous work by others indicates that GTP analogues can change the kinetics of G protein coupling and therefore affect the affinity status of the receptor to agonist. To test this theory, GTP and two non-hydrolyzable GTP analogues, GTP-γ-S and Gp(NH)pp, were included in the binding assay. Treatment of the membrane with these GTP analogues can decrease the specific binding of the CHO cell membrane to [³H]DAMGO, suggesting that the expressed μ receptor is physically associated with G proteins and that dissociation of the G protein α subunit from β and γ subunits upon GTP binding affects the conformation of associated receptor and leads to reduced agonist binding. The effect of sodium on the agonist binding was also tested, since early studies using brain membranes suggested that sodium affects opioid agonist binding through interaction with G proteins. Different concentrations of NaCl were included in the membrane binding assays and a dose-dependent inhibition of DAMGO binding by sodium was observed, further indicating the involvement of G proteins in the μ receptor coupling.

Effect of chronic morphine treatment on the μ receptor-mediated inhibition of adenylyl cyclase activity:

Previous studies in cell lines expressing endogenous opioid receptors demonstrated that opioid receptors are coupled to the inhibition of adenylyl cyclase, and that chronic treatment with opioid agonists may modulate such coupling. To test whether the cloned μ receptor is coupled to adenylyl cyclase, intracellular level of cAMP in the transfected cells were measured, and the effect of μ receptor activation by DAMGO was determined. The cAMP level in CHO cells (naive cells) was increased upon forskolin stimulation, and 1 μM DAMGO reduced this level to ~70% of the control. After the cells were chronically treated with morphine, a μ receptor agonist, DAMGO-induced inhibition of cAMP level was enhanced, resulting in a reduction to ~40% of the control. This result suggests that morphine treatment enhanced the effectiveness of the μ receptor-mediated inhibition of adenylyl cyclase activity. It is noteworthy that chronic morphine treatment also elevated the overall level of the cAMP, as reflected in the increased cAMP at both basal and forskolin-stimulated states.

To determine the potency of the DAMGO-induced inhibition on adenylyl cyclase activity, the forskolin-stimulated cAMP level in the naive cells was measured in the presence of different concentrations of DAMGO. The intracellular cAMP level in naive cells was reduced by DAMGO in a dose-dependent fashion. The $EC_{50}$ for DAMGO calculated from the data is about 30 nM. The DAMGO effect is clearly the result of the μ receptor activation, since treatment of the cells with 1 μM DAMGO in the presence of 10 μM naloxone completely abrogated the inhibitory effect of DAMGO on cAMP accumulation, and in non-transfected parental CHO cells DAMGO had no effect on the intracellular cAMP level. Chronic treatment of the cells with morphine for 24 hr enhanced the effectiveness of the DAMGO-induced inhibition of adenylyl cyclase activity. The maximal inhibition of the intracellular cAMP by DAMGO is about 60%, significantly higher than that by DAMGO in naive cells (~25%).

To test whether receptor numbers are changed upon chronic morphine treatment, CHO cells expressing the cloned μ opioid receptors were chronically treated with 1 μM of morphine for 24 hr and the whole-cell binding to [³H]DAMGO was measured to determine the number of the total surface receptors. There was no appreciable change in the number of surface receptors, nor was there noticeable change in the affinity for DAMGO after chronic morphine treatment. These results suggest that unlike the changes in adenylyl cyclase activities upon morphine treatment, receptor down regulation does not occur after chronic morphine treatment in these CHO cells.

C. Discussion

Opioid peptides and opiate alkaloids exert their physiological effects by interacting with at least three distinctive types of opioid receptors, μ, κ and δ. Among them, the μ opioid receptor plays an important role in the mediation of supraspinal analgesia, and is also involved in the development of opioid tolerance and dependence. Chronic use of morphine in clinical practice may result in opioid tolerance and dependence. The underlying biological mechanisms for these usage-induced changes, however, are not well understood. Several cell models have been used to study the cellular mechanisms associated with the complex opioid effects. A human neuroblastoma cell line (SK-N-SH and its derivative SH-5Y5) that expresses a mixture of μ and δ receptor has been widely used for studying the signal transduction mechanisms associated with the μ receptor (Yu et al., 1986). Rat pituitary tumor cells (7315c) were also identified to express predominantly the μ receptor (Frey and Kebabian, 1984). However, characterization of the cellular mechanism in the context of morphine tolerance and dependence was compromised by a lack of knowledge about the molecular identity of opioid receptors in these cells.

Molecular cloning of the μ opioid receptor provides an opportunity to study the opioid effect at both cellular and molecular levels. A cell model with the cloned μ receptor would allow studies on the molecular mechanisms of opioid effects as well as the cellular changes during opioid tolerance and dependence. One of the goals in this study is to establish a cell line that stably expresses the cloned μ opioid receptor. As shown in the saturation studies with [³H] DAMGO and RT-PCR with μ-specific primers, a CHO cell line was obtained with high level expression of the μ opioid receptor. The $K_d$ value derived from the saturation binding is comparable with that identified in transient expression studies in COS cells. Both saturation binding and RT-PCR also demonstrated that there are little endogenous μ receptors present in the parental CHO cells. Thus, expressing the cloned μ receptor in CHO cells provided a model system to study μ receptor-related cellular changes.

The molecular structure of opioid receptors deduced from the nucleotide sequence suggests that they belongs to the family of G protein-coupled receptors. Stimulation of the transfected CHO cells with the μ-selective agonist DAMGO significantly elevates the low $K_m$ GTPase activity. The specificity of this effect is confirmed by the blockade with the opioid antagonist naloxone. Similar to the results from earlier studies using brain homogenate and cultured cells, application of GTP and nonhydralizable GTP analogues affects the opioid agonist binding in the transfected CHO cells. These results suggest that G proteins are associated with the μ opioid receptor in its non-activated resting state, and the receptor activation leads to changes of G protein activities, whereas the conformational state of G proteins also affects receptor binding to ligands. Furthermore, this receptor is functionally coupled to the inhibition of adenylyl cyclase in CHO cells. Treatment of the transfected cells with DAMGO resulted in a dose-dependent change in the forskolin-stimulated cAMP accumulation. The $EC_{50}$ calculated from the dose-response curve of DAMGO effect is about 30 nM, higher than the $IC_{50}$ value derived from the competition binding studies. The discrepancy between the functional activity and the binding affinity values may be due to the presence of spare receptors on the cell, although other possibilities may also exist. It should be noted that the efficacy for adenylyl cyclase inhibition by the $\mu$ opioid receptor in the CHO cells is similar to that in SK-N-SH and 7315c cells. The relative efficacy of $\mu$ opioid receptor to inhibit adenylyl cyclase activity seems to be lower than other G protein-coupling receptors that are linked to the inhibition of adenyly cyclase, e.g. $\alpha$2-adrenergic receptor, serotonin 1A receptor and dopamine receptors. The difference of their ability to inhibit adenylyl cyclase suggests that different G proteins may be involved in coupling distinct receptors to a common effector molecule. Since more than one adenylyl cyclases have been identified in the cell, an alternative explanation may be a differential coupling to different subtypes of adenylyl cyclases by distinctive membrane receptors.

To test if this cell line can serve as a cell model to study morphine tolerance and dependence, chronic treatment with morphine was performed. The protocol the inventors used is similar to that by many investigators and involves first chronically treating the cells with a moderate concentration of agonist (morphine), washing out the agonist, and then acutely stimulating the cells with various concentrations of agonist. Because the presence of the agonist during the chronic treatment represents a continued inhibitory input, agonist wash-out before acute treatment is equivalent to a disinhibition, and has been compared to a withdrawal paradigm after establishing opioid tolerance. In this cell line, the inventors also observed that both the basal and forskolin-stimulated cAMP levels are elevated after chronic morphine treatment and withdrawal, suggesting that a compensatory mechanism of adenylyl cyclase may have taken place and that upon removal of $\mu$ receptor-mediated inhibition, the increased adenylyl cyclase would lead to higher levels of cAMP. It is interesting to note that chronic morphine treatment displays a differential effect on cAMP levels: while the basal cAMP level after morphine treatment was increased about 60% over the naive cells, the forskolin-stimulated cAMP level was more than doubled by morphine treatment. It is tantalizing to speculate that the differential increase between basal and forskolin-stimulated cAMP levels during chronic morphine treatment reflects a differential sensitivity of two populations of adenylyl cyclase molecules: those present before morphine treatment commenced and that synthesized as the compensatory mechanism takes effect during morphine treatment. It is conceivable that these two populations of adenylyl cyclases may have different composition with regard to cyclase subtypes. With the molecular cloning of multiple cyclases, it should be possible to test this hypothesis.

Another noteworthy phenomenon of morphine treatment is that the DAMGO-induced cAMP inhibition in the morphine-treated cells is more robust, resulting in a doubling in the percentage inhibition of cAMP from about 25–30% inhibition in naive cells to almost 65–70% inhibition in morphine-treated cells. These results suggest that morphine treatment "sensitized" the system, making further inhibition upon acute $\mu$ receptor activation more effective. This is in contrast to the studies with cell lines expressing endogenous $\mu$ receptors, where chronic morphine treatment caused a decrease in the receptor's ability to inhibit adenylyl cyclase. The lack of receptor desensitization in CHO cells suggests a difference in receptor modulation of adenylyl cyclase in different cell types. This may reflect the different composition of endogenous G proteins and/or adenylyl cyclases in CHO cells versus other cell types. Also of interest is that chronic morphine treatment of the transfected CHO cells did not cause down regulation of surface receptors. In the morphine-treated cells, the cell surface receptor number as well as the $K_d$ value for DAMGO was not significantly different from the non-treated naive cells. This is in contrast to agonist-induced down regulation in $\beta_2$-adrenergic receptors. The differential effect of chronic morphine treatment on the adenylyl cyclase activity and the receptor numbers makes this cell line a useful cellular model to study the molecular mechanisms linking the $\mu$ opioid receptor to its effector systems and the changes associated with morphine tolerance and dependence.

Table 4. Effect of chronic morphine treatment on the basal and forskolin-stimulated intracellular cAMP level

| | Intracellular cAMP levels (fmol/1 × $10^3$cells)[1] | | | |
|---|---|---|---|---|
| | Basal | Forskolin | Forskolin + DAMGO | DAMGO/ control |
| Naive cells | 8.0 ± 0.5 | 35.6 ± 0.3 | 25.6 ± 0.3 | 71.9% |
| Morphine-treated | 12.7 ± .02 | 92.0 ± 1.7 | 38.9 ± 1.4 | 42.4% |
| Morphine/naive | 158.7% | 258.4% | | |

[1]Intracellular cAMP levels were measured in naive cells and cells treated with 1 $\mu$M morphine for 24 hours. Forskolin (2 $\mu$M) or DAMGO (1 $\mu$M) was used to determine their effect on the intracellular cAMP level. Data are presented as fmol/1 × $10^3$ cells (meam ± SEM). The effect of morphine is presented as the ratio between the results from the morphine-treated cells and those from naive cells (morphine/naive). Also shown is the ratio between the results from cells treated with forskolin plus DAMGO and those from only forskolin-treated cells (DAMGO/control).

Example VIII: Differential Regulation by cAMP-Dependent Protein Kinase and Protein Kinase C of the Mu Opioid Receptor Coupling to a G Protein-Activated Potassium Channel The inventor has also coexpressed a mu opioid receptor and a G protein-activated $K^+$ channel in Xenopus oocytes. Stimulation of the $\mu$ opioid receptor induced an inwardly rectifying current that was blocked by opioid receptor antagonist naloxone, indicating that the $\mu$ opioid receptor is functionally coupled to the $K^+$ channel. The coupling is mediated by G proteins, since pertussis toxin treatment reduced the $K^+$ current and injection of GTP-$\gamma$-S enhanced it. Repeated stimulation of the $\mu$ receptor leads to desensitization, as the $K^+$ current from the second stimulation was reduced to 70% of that from the first one. Both cAMP-dependent protein kinase (PKA) and protein kinase C (PKC) regulate this process, but in opposite direction. Activation of PKC by treatment of the oocyte with phorbal ester potentiated the desensitization of the $\mu$ receptor-induced current. However, incubation of the cell with a membrane permeable cAMP analog, 8-chlorophenylthio-cAMP, completely abolished the desensitization. The cAMP effect appears to be mediated by PKA, since injection of a PKA catalytic subunit showed the same effect as cAMP incubation. These results suggest that PKA and PKC differentially regulate the $\mu$ opioid receptor coupling to the G protein-activated $K^+$ channel.

A. Material and Methods

Chemicals: $^3$H-DAMGO (38 Ci/mmol) was from National Institute of Drug Abuse. DAMGO was from Bachem. Naloxone was from Research Biochemicals International. All other chemicals were from Sigma.

Complementary DNA clones for the μ opioid receptor and the G protein-activated K$^+$ channel: A cDNA clone, MOR-1, containing the protein coding region of a rat μ opioid receptor has been described (Chen et al., 1993a). Based on the cDNA sequence for the rat G protein-activated K$^+$ channel (Kubo et al., 1993; Dascal et al., 1993), two oligonucleotide primers were synthesized corresponding to the 5'- and 3'-untranslated regions respectively: CTCG-GATCCGTATTATGTCTG (SEQ ID NO: 12) and ATAGTC-GACTAAAACTAAATC (SEQ ID NO: 13). PCR was performed in an air cycler (Idaho Technology) with 10 sec at 94° C., 20 sec at 56° C. and 1 min at 75° C. for 35 cycles, using the two primers and the purified lambda DNA from a rat brain cDNA library (Snutch et al., 1990). A Deep Vent$_R$ DNA polymerase (New England Biolabs) was used to reduce PCR errors. The 1.7 kb PCR product was cloned into a TA-cloning vector (Invitrogen). Both cDNA clones were used to synthesize mRNA by in vitro transcription.

Oocyte injection and binding assay: Xenopus oocytes were prepared. In vitro transcribed RNA (1–2 ng/oocyte) was injected into oocytes with a Drummond microinjector. Oocytes were incubated in L-15 medium supplemented with 0.8 mM of glutamine and 10 μg/ml of gentamycin at 20° C. for 3–4 days before analysis. Binding of the injected oocytes was carried out in regular ND96 (96 mM NaCl, 2 mM KCl, 1 mM MgCl$_2$ and 1.5 mM CaCl$_2$) solution at 20° C. for 90 min, using 1 nM of $^3$H-DAMGO. Binding was terminated by vacuum filtration through a Whatman GF/B filter pretreated with 1% polyethylenimine. Three milliliters of ND96 was used to wash the oocytes, and nonspecific binding was determined using 1 μM of naloxone. The radioactivity of the oocytes were determined in 6 ml of Scintiverse (Fisher) with a Beckman LS5801 scintillation counter.

Electrophysiology: Oocytes were voltage-clamped at −80 mV with two electrodes filled with 3 M of potassium chloride and having a resistance of 0.5–2 MΩ, using an Axoclamp-2A and the pCLAMP software (both from Axon Instruments). Oocytes were superfused with either ND96 containing 6 mM of CaCl$_2$ or a high potassium solution (96 mM KCl, 2 mM NaCl, 1 mM MgCl$_2$ and 1.5 mM CaCl$_2$). Analysis of variance and student t-test were used to determine the statistic significance among different groups.

B. Results

Coupling of the μ opioid receptor to the G protein-activated K$^+$ channel: To determine whether the μ opioid receptor couples to the G protein-activated K$^+$ channel, the inventors expressed both proteins in Xenopus oocytes. Messenger RNAs of these two clones were generated by in vitro transcription, and oocytes were microinjected with each mRNA alone or both mRNAs. $^3$H-DAMGO, a highly selective ligand for μ opioid receptors, was used in whole-cell binding assay to determine the expression of the μ opioid receptor, and nonspecific binding was the residual binding not blocked by naloxone. Oocytes injected with mRNAs for both the μ opioid receptor and the K$^+$ channel displayed a specific binding of about 1 fmol/oocyte, whereas oocytes injected only with the K$^+$ channel mRNA did not show any appreciable binding to $^3$H-DAMGO.

Coupling of the μ opioid receptor to the K$^+$ channel was studied by two-electrode voltage clamp. In the oocytes injected with either the μ receptor mRNA or the K$^+$ channel mRNA alone, no membrane current was observed with the μ_receptor agonist DAMGO (data not shown), indicating that there are no endogenous currents in oocytes that are activated by DAMGO, and that either the μ receptor or the K$^+$ channel alone is not sufficient to generate DAMGO-induced currents. However, coexpression of both proteins gave rise to membrane currents upon DAMGO stimulation. Exposure of the oocytes to 1 μM of DAMGO produced an inward membrane current that was completely blocked by the opioid receptor antagonist naloxone. In agreement with the inwardly rectifying nature of this G protein-activated K$^+$ channel, the current-voltage relationship of the DAMGO-induced membrane current showed a characteristic inward rectification, as the current magnitude increased with progressive membrane hyperpolarization whereas there was little current when the membrane was depolarized above 0 mV. As expected for a K$^+$ channel, membrane current was completely blocked by 100 μM of Ba$^{2+}$.

G protein involvement in the coupling: Previous studies in neurons suggested that the coupling of opioid receptors to the membrane K$^+$ conductance involves a pertussis toxin (PTX)-sensitive G protein, To test whether the coupling between the μ opioid receptor and the K$^+$ channel in oocytes is affected by PTX, cells injected with both mRNAs were incubated with 0.5 μg/ml of PTX for 24 hours. PTX treatment reduced the DAMGO-induced membrane current by 60%, and this reduction was proportionally uniform across the voltage range. These data indicate that a PTX-sensitive G protein(s) is needed for the μ receptor activation of the K$^+$ channel, accounting for at least 60% of the coupling.

The involvement of heterotrimeric G proteins in the coupling was further studied using GTP-γ-S, a nonhydrolizable GTP analog that interacts with G protein and keeps it in an activated state. After DAMGO-induced current reached a plateau, intracellular injection of GTP-γ-S elicited a further increase of the current. When the time course of the normalized current is plotted using the peak current value before GTP-γ-S injection as the standard, GTP-γ-S injection resulted in a gradual rise of the current which, after reaching the maximum, decreased toward the baseline following a similar time course as that of control oocytes. However, injection of GTP-γ-S itself without stimulation of the μ receptor by DAMGO did not induce appreciable membrane current change (data not shown), indicating that the GTP-γ-S mediated enhancement of the K$^+$ conductance is dependent on the activation of the receptor.

Differential regulation of the coupling by PKA and PKC: To determine whether the coupling between the μ opioid receptor and the K$^+$ channel is regulated by PKA- and PKC-mediated phosphorylation, the inventors used a special protocol. The oocyte was superfused with high-potassium solution (HK) while DAMGO-induced response was measured. Then the superfusate was switched to ND96 solution and the cell was either treated with a chemical to stimulate a kinase or microinjected with the catalytic subunit of PKA. The cell was allowed to recover after the treatment, and DAMGO-induced response was measured again in HK solution. Comparison between the maximum responses before and after the treatment thus reveals how much desensitization has occurred after the first DAMGO stimulation. The DAMGO-induced membrane current recorded approximately 15 min after primary exposure was only about 70% of the first response, indicating that desensitization has taken place. Treatment of the oocytes with phorbal ester PMA, a PKC activator, further reduced the second response, suggesting a negative regulation by PKC of the μ opioid receptor-activated K$^+$ current.

Surprisingly, treatment of the oocyte with 8-CPT-cAMP, a membrane permeable cAMP analog that can diffuse into the cell and stimulate PKA, completely abolished the desensitization observed in untreated oocytes. To determine whether the 8-CPT-cAMP effect on preventing desensitization is mediated by PKA, the catalytic subunit of PKA was injected into the oocytes after the first DAMGO stimulation. This resulted in the same effect as 8-CPT-cAMP incubation. The current-voltage relation was determined at the peak of both the first and the second DAMGO-induced response. Activation of PKC by PMA treatment enhanced desensitization over the entire voltage range, whereas either activation of PKA by cAMP or direct enzyme injection prevented desensitization across the voltage range (data not shown). These data suggest that the two kinases have opposite effect on the μ opioid receptor-activated $K^+$ current, exerting differential regulation on this process.

C. Discussion

Neurotransmitters modulate the excitability of neurons by affecting ion channels, $K^+$ channel being one of the primary targets of such modulation. In fact, many neurotransmitters have been shown to couple to a $K^+$ conductance in neurons. The effect of neurotransmitters on $K^+$ channel involves a receptor-mediated mechanism, and opioids are no exception. In both locus coeruleus and hippocampus, μ opioid receptors have been shown to regulate a $K^+$ conductance, leading to membrane hyperpolarization and a decrease in neuronal firing rate. The recent cloning of a μ opioid receptor as well as a G protein-activated $K^+$ channel provided the opportunity to examine the molecular mechanism of this coupling. The $K^+$ channel was isolated from the heart atrial cells, where it is mainly involved in the heart beat regulation mediated by muscarinic receptors. However, both RNA blot analysis and cloning effort suggested that the same channel also exists in the brain (Kubo et al., 1993: Dascal et al., 1993), thus it may mediate the neuronal effect of various neurotransmitters. In this report, the inventors showed that the μ opioid receptor and the G protein-coupled $K^+$ channel, when coexpressed in Xenopus oocytes, are functionally coupled. Although the inventors can not exclude the possibility that other $K^+$ channels may be involved in the coupling to the μ opioid receptor, the data suggest that this G protein-coupled inward rectifier may be the long-sought $K^+$ channel that is linked to the μ opioid receptor and other neurotransmitter receptors. Kubo et al. showed that this channel can be activated by injection of purified G protein Gαi2, $β_1$ and $γ_2$ subunits (Kubo et al., 1993). The experiments with PTX and GTP-γ-S suggested the involvement of a PTX-sensitive G-protein(s) in the coupling. It has been shown that opioid receptors are associated with G proteins of the $G_i$ and $G_o$ subtypes. Therefore, it is not surprising that similar PTX-sensitive G proteins of the $G_i$ and/or $G_o$ subtypes in Xenopus oocyte can mediate the coupling between the μ opioid receptor and the $K^+$ channel. However, the fact that PTX treatment did not completely block the DAMGO-induced $K^+$ current suggests that other G proteins not sensitive to PTX may also be involved in the μ receptor coupling.

Phosphorylation by kinases is one of the most important mechanisms for functional regulation of many cellular proteins including neurotransmitter receptors and ion channels, and PKA and PKC are two of the most widely studied kinases. Phosphorylation of $β_2$-adrenergic receptor by either PKA or PKC leads to its uncoupling from G proteins, resulting in desensitization to further agonist stimulation. In the case of voltage-dependent $Ca^{2+}$ channels such as the endogenous oocyte $Ca^{2+}$ channel, PKA and PKC mediated phosphorylation is able to potentiate channel activity. CFTR, a $Cl^-$ channel associated with cystic fibrosis, is also regulated by cAMP through PKA pathway. Regulation of the inwardly rectifying $K^+$ channels by either PKA or PKC, however, is not clear. Molecular cloning has shown that the μ opioid receptor and the G protein-activated $K^+$ channel possess multiple putative sites for PKA and PKC phosphorylation. In this study, the inventors found that the coupling of the μ opioid receptor to the $K^+$ channel desensitizes upon repeated stimulation by the μ receptor agonist DAMGO, as the peak current by the second DAMGO application is reduced to 70% of that by the first one. Treatment of the cells with phorbal ester enhanced this desensitization, suggesting PKC-mediated phosphorylation. Surprisingly, treatment with 8-CPT-cAMP or injection of the catalytic subunit of PKA completely abolished the desensitization. Thus, PKA and PKC appear to exert opposite effects on this μ receptor-induced $K^+$ current. These results, however, do not reveal the molecular entities of PKA- and PKC-mediated phosphorylation. Further studies using mutagenesis are needed to determine the correlation between specific phosphorylation sites on these membrane proteins and the regulation by PKA and PKC.

Example IX: Molecular Cloning of a Novel Member of the Opioid Receptor Gene Family The inventor has also isolated a cDNA (SEQ ID NO: 16) from rat brain by low stringency hybridization with the rat μ opioid receptor cDNA. Sequence analysis of this clone indicated that it contains an open reading frame capable of encoding a 367 amino acid protein (SEQ ID NO: 17). The deduced amino acid sequence of this protein shows high degrees of homology to all three opioid receptors, μ, κ, and δ, suggesting that it is a member of the opioid receptor gene family. RNA blot analysis detected high level expression of the receptor mRNA in the brain. Using a PCR-based method, the relative mRNA abundance of all four members of the opioid receptor gene family in the rat brain was estimated. The results suggest that the μ receptor mRNA has the highest abundance of ~68%, followed by ~14% for δ, ~10% for κ and ~8% for this new member. Despite the high sequence homologies between this protein and the other opioid receptors, expression studies of this clone in COS-7 cells did not show binding to [$^3$H]diprenorphine, a ligand that binds to the other three opioid receptors. Furthermore, coexpression of this receptor with a G protein-activated potassium channel in Xenopus oocytes did not show functional coupling upon stimulation with μ, κ and δ agonists. Given the similar degrees of high homology to the μ, κ and δ opioid receptors and the lack of apparent affinity for their ligands, this receptor does not appear to belong to any of the three known classes of opioid receptors. Rather, it represents a novel member of the opioid receptor gene family, not identified from previous pharmacological studies.

A. Materials and Methods

Library screening: 1.4 kb HindIII cDNA fragment containing the complete protein coding region of the rat μ opioid receptor (Chen et al., 1993a) was used to screen a rat brain cDNA library under low stringency. Hybridization and the final wash were performed at 55° C. Sequence analysis of 24 isolated clones showed that four identical cDNA clones were similar to the three opioid receptors, μ, κ and δ. One of four isolates was used for subsequent sequence analysis using double stranded DNA and sequenase version 2 (USB). Hydropathy analyses were performed and putative post-translational modification sites of the receptor protein were identified using the PCGENE program. Sequence comparisons of this clone with other three opioid receptors as well as other G protein-coupled receptors were performed by the BLAST program available from NIH.

RNA and DNA blot analysis: A rat multiple tissue ploy(+) RNA blot (Clontech) was used to study the tissue distribution of the putative opioid receptor under the company recommended conditions. The RNA blot was hybridized with a 2.0 kb HindIII fragment containing the entire protein encoding region of the putative opioid receptor clone. The final wash was performed in 0.2×SSC and 0.1% SDS at 55° C. For Southern analysis, 30 μg of rat genomic DNA was digested with BamHI, EcoRI and HindIII respectively and separated on a 0.8% agarose gel. The DNA was transferred to a Hybond-N membrane (Amersham) as described. The hybridization and wash condition was the same as for the RNA blotting.

Reverse transcription and PCR: Total RNA was prepared from rat brain. Reverse transcription was performed with 2 μg of total RNA and random hexomers in the presence of 50 mM Tris (pH 7.5), 5 mM $MgCl_2$ and 12 units of AMV reverse transcriptase at 37° C. for 90 minutes. The cDNA product was directly used in PCR with two degenerate oligonucleotide primers: AC(C/T)GC(A/C)ACCAACATCTACAT (SEQ ID NO: 14, ACYGCMAC-CAACATCTACAT under rules of 37 C.F.R. § 1.822) and GCT(G/A)GT(A/G)AACATGTTGTAGTA (SEQ ID NO: 15, GCTRGTRAACATGTTGTAGTA under rules of 37 C.F.R. § 1.827). Forty-four cycles of PCR were performed at 94° C. for 5 sec, 55° C. for 10 sec and 75° C. for 1 min in an air cycler (Idaho Technology). PCR products were directly cloned into a TA-cloning vector (Invitrogene). Seventy-four clones were randomly chosen for sequence analysis.

Transient expression in COS-7 cells: A 2.0 kb HindIII fragment encompassing the entire protein coding region of the putative opioid receptor was cloned downstream of the human cytomegalovirus promoter in a mammalian cell expression vector, pRC/CMV (Invitrogen). The recombinant plasmid was introduced into COS-7 cells by electroporation. Membrane preparation and binding assays were performed. One nalomolar [$^3$H]diprenorphine was used in the binding assay.

Expression and electrophysiological studies in Xenopus oocytes: Xenopus oocytes were prepared as described (Chen and Yu, 1994). The putative receptor mRNA was synthesized using T7 polymerase under the condition described before (Chen and Yu, 1994). The receptor mRNA was coinjected with a G protein-activated potassium channel mRNA into the oocytes. Electrophysiological analysis of the oocytes was carried out by a two-electrode voltage clamping method in a solution with high potassium concentration (Chen and Yu, 1994). One micromolar of different opioid agonists was used for the oocyte recording assay.

B. Results and Discussion

A cDNA clone was isolated by screening a rat brain cDNA library under low stringency using the protein-coding region of the rat μ opioid receptor cDNA (Chen et al., 1993a) as the radiolabeled probe. Sequence analysis of the clone (SEQ ID NO: 16) showed an open reading frame capable of encoding a protein with 367 amino acids (SEQ ID NO: 17). Hydropathy plot analysis showed that the protein contains seven hydrophobic domains, a structural signature common to most G protein-coupled receptors. Sequence comparison of this clone with the three cloned opioid receptors suggests that it is closely related to these opioid receptors in structure. The overall similarity of this receptor with the three opioid receptors is around 65%, and a higher level of homology is found in the putative transmembrane domains as well as in the intracellular loop between transmembrane domains 5 and 6, a region that has been proposed to interact with G proteins. Similar to other opioid receptors, it possesses many sequence signatures that are conserved among many G protein-coupled receptors. The two aspartic acids in transmembrane domains 2 and 3 may be crucial for ligand binding of the receptor, because a recent mutagenesis study on the δ receptor has found this site to be involved in determining the ligand binding specificity. The two cysteine residues may form a disulfide bond that is important in restraining the conformation of the receptor protein. A cysteine residue after the seventh putative transmembrane domain is also conserved between this receptor and other three opioid receptors, and it may form a palmitoylation site for anchoring part of the C-terminus of the receptor to the membrane to form a fourth intracellular loop. Studies on the β-adrenergic receptor have found that palmitoylation at this site is involved in receptor desensitization. Besides these conserved structural features with other opioid receptors, this receptor also has one putative protein phosphorylation site by cAMP-dependent protein kinase and two sites for protein kinase C. Phosphorylation at these sites may be of importance in regulating receptor-G protein coupling.

Sequence comparison of this protein with other G-protein coupled receptors also detected homology to other receptors, including somatostatin receptors, angiotensin receptors and formyl peptide receptor. However, the degree of similarity of this receptor to these non-opioid receptors is considerably lower than that to the three opioid receptors, suggesting its structural similarity with opioid receptors. It is noteworthy that this clone has an almost equal degree of similarity to other three opioid receptors. This receptor has a ~65% similarity to each of the μ, κ and δ receptors, whereas the similarity between any of the two opioid receptors is ~70%. These homology values suggest that this receptor is likely a novel member of the opioid receptor gene family, and it does not appear to be a subtype within one the three receptor classes, i.e., μ, κ and δ.

To determine the tissue distribution pattern of this novel receptor, RNA blot analysis was performed using RNA isolated from various rat tissues. Hybridization of the RNA blot with the protein coding region sequence of this receptor showed a high level expression in the brain. Three major transcription products were detected, with molecular sizes of about 10 kb, 7.5 kb and 3.4 kb, respectively. The different sizes of mRNAs may result from differential splicing of the same primary transcript, a phenomenon found in many other mammalian genes including opioid receptors or from multiple polyadenylation sites.

Southern blot analysis was also performed. Rat genomic DNA was digested with HindIII, EcoRI or BamHI and hybridized with the same radiolabeled probe as used in the RNA blot analysis. The simple pattern of hybridizing bands in each of the restriction digestions suggests that the gene for this receptor may be a single-copy one. It is noteworthy that the strongly hybridizing band in HindIII is about 2 kb. Since that restriction analysis of the cDNA clone detected an internal HindIII site in its 3'-untranslated region (data not shown) and that the protein coding region is about 1.1 kb, this result suggests that this receptor gene is likely a compact one with small or no introns in its protein coding region.

In an effort to estimate the relative mRNA abundance of this receptor and the other three opioid receptors in the brain, RT-PCR was performed using the total brain RNA. Two degenerate PCR primers were used that would amplify all four receptor sequences. PCR products were cloned and characterized by sequence analysis. The μ receptor mRNA constitutes about two-thirds of the PCR clones, suggesting that the highest abundance in the brain among opioid receptors. The other three receptors, δ, κ and this novel receptor, display comparable levels of abundance, suggesting that the expression level of this receptor in the brain is similar to that of κ and δ receptors. Using crude membrane preparations from animal brain, binding studies suggest multiple receptor subtypes within each of the μ, κ, and δ opioid receptor type. The inventors designed the degenerate primers to detect all three opioid receptors and this novel receptor in their most conserved regions, and yet the inventors did not obtain previously unidentified sequences. These results suggest that other subtypes of opioid receptors, if any, may either have considerable sequence divergence in the PCR primer regions, or are expressed at much lower abundance than these four receptors.

In attempt to determine the pharmacological profile of this novel receptor, the inventors expressed the cDNA clone in both COS-7 cells and Xenopus oocytes. A HindIII fragment encompassing the entire protein coding region of this receptor was subcloned in pRC/CMV vector downstream from the cytomegalovirus promoter, and this construct was used in transient expression studies in COS-7 cells. As positive controls for COS-7 expression, the rat μ opioid receptor cDNA in the same vector (Chen et al., 1993a) was used in parallel transfection (data not shown). Binding assays using the COS-7 cell membranes transfected with this receptor clone and [$^3$H]diprenorphine, a ligand with high affinity for the three opioid receptors, did not detect any specific binding (data not shown). Furthermore, mRNA of this clone was synthesized by in vitro transcription and coinjected into Xenopus oocytes with the mRNA for a G protein-activated potassium channel. It has been shown that this inwardly rectifying potassium channel is functionally coupled to both δ and μ opioid receptors. However, no potassium conductance was induced by stimulation of the oocytes with a broad range of opioid agonists including DAMGO, morphine, DPDPE, U-50488 and U-62066 (data not shown). These results further suggest that this receptor may not belong to any of the three opioid receptors.

Thus, the inventors have isolated a novel seven-helix receptor cDNA. The high degrees of sequence homology with all three types of opioid receptors and a lack of apparent affinity for many opioid ligands suggest that it encodes a novel member of the opioid receptor gene family, with previously unknown pharmacological characteristics.

Example X: Sequence Polymorphism in Human Mu Opioid Receptor Effecting Pharmacology The inventor has transfected the human mu receptor cDNA into COS cells. The expressed receptor protein confers high affinity binding to opioid alkaloids with abuse potential, as well as endogenous opioid peptides. For example, morphine and methadone have $K_i$ values of 3.6 nM and 3.7 nM, respectively. Also, Met-enkephalin, β-endorphin, and dynorphin A (1-17) display $K_i$ values of 2.2 nM, 1.8 nM, and 1.6 nM, respectively.

It is of particular interest that dynorphin A (1-17) displays nanomolar affinity at the mu receptor the inventors have cloned, because a recent publication also reported the cloning of a human mu receptor cDNA (Wang et al., 1994), with virtually identical pharmacology to these results except that for dynorphin A (1-17). While the inventors see a $K_i$ value of 1.6±0.3 nM, the clone isolated by Wang et al. gives a $K_i$ value of 284±110 nM (Wang et al., 1994)—a difference of over 100-fold. When the two sequences are compared, there is only a single-base difference at the nucleotide no. 151 (corresponding to codon no. 51 in the amino acid sequence), resulting in the substitution of an aspartate residue for an asparagine—a net loss of one negative charge.

Dynorphin A has the highest affinity at the kappa opioid receptor sites (Goldstein, 1987), and is thus considered a kappa agonist (Chavkin et al., 1982). However, while it binds at the kappa receptors with subnanomolar affinity, it does display reasonably good binding at the mu receptors, with affinity value in the nanomolar range (Goldstein, 1987; Pasternak, 1993); thus it may also interact with dynorphin A in the body. Detailed studies of dynorphin A binding in the human brain is very limited. There are some reports, however, on the comparative studies using rodent and bovine brain membranes (Pasternak, 1993). For example, using guinea pig brain membranes, it has been shown that dynorphin A (1-17) can displace radiolabeled PL-17, a mu-selective ligand, with a 5 nM affinity (Kawasaki et al., 1990). In another study, dynorphin A (1-17) was found to displace radiolabeled DAMGO, another mu-selective ligand, with 3 nM affinity (Vaughn and Taylor, 1989). When a distinction is made with regard to the putative subtypes for the mu receptor, the $K_i$ values for dynorphin A (1-17) are given as 0.7 nM at $Mu_1$ site and as 2.2 nM at the $Mu_2$ site (Clark et al., 1988). When the cloned murine opioid receptors were compared side-by-side for their ligand binding properties, it was found that dynorphin A (1-17) was very potent in displacing $^3$H-U-69593 binding to the mouse kappa receptor at 0.5 nM affinity, and showed lower affinity at the rat mu receptor with affinity of 32 nM (Raynor et al., 1994). It appears that species differences may exist regarding the affinity of dynorphin A (1-17) binding at the mu receptor, and clearly more detailed studies are needed to characterize this property, especially for the mu receptor in humans, which may contain considerable sequence polymorphism since experimental laboratory animals are usually inbred.

The single-base difference between the cDNA the inventors isolated and that by Wang et al. may serve as an example of sequence polymorphism in humans, since these two clones were from two independent sources—the inventors used a cDNA library from Clontech (Mestek et al., 1994), whereas Wang et al. used a cDNA library from Stratagene (Wang et al., 1994). Neither clone was obtained by PCR, therefore the possibility of PCR error is not a concern. Since both clones give functional receptors, they may represent two different alleles for the mu receptor gene in humans. In an effort to start to evaluate the prevalence of alleles, the inventors synthesized two oligonucleotides that flank codon no. 51, and used them as PCR primers to amplify the mu receptor region containing codon no. 51. DNA samples from five individuals, three of African-American heritage and two of Caucasian, were used as PCR templates, and the PCR products were analyzed by DNA sequencing. These samples all contain the same codon no. 51 as that in the Inventor's clone, predicting an aspartate amino acid residue at this position. The number of individuals the inventors tested is small, therefore no conclusion can be drawn regarding the prevalence of allele frequency. This pilot study does suggest, however, that the mu receptor allele bearing an aspartate codon at no. 51 position may be relatively common. A definitive estimation of allele frequency will not be known until more work is completed from this proposal. It should be pointed out that since the Inventor's cDNA clone containing the same codon gives a mu receptor with nanomolar affinity for dynorphin A (1-17), the possibility of dynorphin A acting at the mu receptor in humans, in addition to the kappa receptor, needs to be examined.

Another implication of the codon no. 51 polymorphism is that this position resides in the N-terminal portion of the mu receptor, a region previously considered to be unrelated to the ligand biding capacity of the receptor. This suggests that screening for naturally occurring polymorphisms offers an innovative approach to identify critical domains in receptor function. Using the strategy the inventors have employed in examining codon no. 51 variations, the entire mu receptor coding sequence can be readily characterized from each individuals, thus providing detailed information on sequence polymorphisms in this receptor gene.

Example XI: Functional Modulation by a Mu Opioid Receptor of a Voltage-Activated Calcium Channel The inventor has also studied the functional modulation of voltage-activated calcium channels by mu opioid receptor. Using the cDNA clone for a voltage-activated calcium channel (Soong et al., 1993), the voltage-activated calcium channel is expressed in Xenopus oocytes by microinjection of the plasmid containing the cDNA for the calcium channel. A plasmid containing the mu opioid receptor (Chen et al., 1993a) is also co-injected for co-expression. Two to three days after injection, oocytes are voltage-clamped and the calcium channel expression is measured using a step protocol. The calcium channel function is determined using a barium solution (in mM: 40 $BaCl_2$, 10 NaCl, 2 KCl, 5 HEPES pH 7.5, 36 TEA-Cl, 5 4-amino pyridine, 0.4 niflumic acid) and shown as barium current through the calcium channel. Command voltage steps from a holding potential of −100 mV to various potentials elicited barium currents. The current-voltage (I–V) relationship is expected of the calcium channel (Soong et al., 1993) and the maximum peak currents are near 0 mV.

Oocytes injected with both a voltage-activated calcium channel plasmid and a mu opioid receptor plasmid express both proteins; activation of the mu opioid receptor results in a pronounced suppression of the calcium channel function as indicated by an over 80% reduction in the currents across the entire activation voltage range. After wash out of the mu opioid receptor agonist DAMGO, the currents gradually recover, suggesting that the mu opioid receptor effect on the calcium channel may be mediated by a modification of the channel such as protein phosphorylation or dephosphorylation.

Example XII: Characterization of the Cloned Human Mu Opioid Receptor

The pharmacological properties of the cloned human μ opioid receptor and the distribution of message encoding the μ receptor in human brain have been examined by Bell and Reisine (1994).

A. Materials and Methods
Abbreviations:

| | |
|---|---|
| β-FNA | β-funaltrexamine |
| CTOP | D-Phe-Cys-Tyr-D-Trp-Orn-Thr-Pen-Thr-NH2 (SEQ ID NO: 16 (SEQ ID NO: 18, Phe Cys Tyr Trp Orn Thr Xaa Thr pursuant to rules of 37 C.F.R. § 1.822). |
| DAMGO | [D-Ala2,MePhe4,Gly-o15]enkephalin |
| GTPgS | guanosine-5'-O-(3-thiotriphosphate) |
| IBMX | isobutylmethylxanthine |
| PTX | pertussis toxin |

Cloning: To clone the human μ opioid receptor, a cDNA library was constructed from human caudate nucleus mRNA was screened under reduced stringency with the rat μ opioid receptor cDNA (Chen et al., 1993) and complete sequence analysis of one cDNA revealed an open reading frame of 1200 bp, predicting a protein of 400 amino acids. For receptor expression, the cDNA containing the open reading frame of the receptor was cloned downstream of the human cytomegalovirus promoter in the mammalian expression vector pcDNA3 (Invitrogen). Details concerning the isolation of the human μ opioid receptor cDNA will be reported elsewhere (Mestek et al., submitted). The cDNA sequence has been submitted to GenBank (accession number L29301).

Radioligand Binding Studies: Receptor binding assays were performed using membranes from COS-7 cells transiently expressing the human μ receptor 48 hours after transfection as previously described (Raynor et al., 1994). For radioligand binding assays, cells were harvested in 50 mM Tris-HCl (pH 7.8) containing 1 mM ethylene glycol bis(b-aminoethyl ether)-N,N'-tetraacetic acid, 5 mM $MgCl_2$, 10 mg/ml leupeptin, 10 mg/ml pepstatin, 200 mg/ml bacitracin and 0.5 mg/ml aprotinin (buffer 1) and centrifuged at 24,000×g for 7 min at 4° C. The pellet was homogenized in buffer 1 using a Polytron (Brinkmann, setting 2.5, 30 sec). The homogenate was then centrifuged at 48,000×g for 20 min at 4° C. The pellet was homogenized in buffer 1 and this membrane preparation was used for the radioligand binding studies. Cell membranes (10–20 mg protein) were incubated with the μ agonist [$^3$H]DAMGO (2 nM, specific activity 55 Ci/mmol) or the antagonist [$^3$H]naloxone (4 nM, specific activity 55 Ci/mmol)(NEN/Dupont, Wilmington, Del.) in a final volume of 200 mL for 40 min at 25° C. in the presence or absence of competing agents. For saturation experiments, cell membranes were incubated with increasing concentrations (0.25–15 nM) of [$^3$H]DAMGO. Nonspecific binding was defined as the radioactivity remaining bound in the presence of 1 mM naloxone. The binding reaction was terminated by the addition of ice-cold 50 mM Tris-HCl buffer (pH 7.8) and rapid filtration over Whatman GF/B glass fiber filters which were pretreated with 0.5% polyethyleneimine/0.1% BSA for at least 1 hour. The filters were then washed with 12 mL of ice-cold Tris-HCl buffer and the bound radioactivity counted in a scintillation counter. Data from radioligand binding studies were used to generate inhibition curves. $IC_{50}$ values were obtained from curve-fitting performed by the mathematical modeling program FITCOMP (Perry and McGonigle, 1988) and saturation data was analyzed using FITSAT (McGonigle et al., 1988) available on the National Institutes of Health-sponsored PROPHET system. The inhibitory binding constant ($K_i$) was calculated from the $IC_{50}$ values using the Cheng-Prusoff equation (Cheng and Prusoff, 1973).

The effect of pretreatment of cells expressing the human μ receptor with morphine or with pertussis toxin on subsequent agonist binding to membranes was also investigated. Cells were treated with either control medium, 1 mM morphine for 4 hr, or 100 ng/ml pertussis toxin for 18 hr prior to radioligand binding studies.

cAMP Accumulation Studies: Studies examining the abilities of compounds to inhibit forskolin-stimulated adenylyl cyclase activity were performed as previously described (Kong et al., 1993). Briefly, cells used for cAMP accumulation studies were subcultured in 12-well culture plates. The following day, cells were transfected and cAMP experiments were conducted 48 hr subsequently. Culture medium was removed from wells and replaced with 500 mL fresh medium containing 0.5 mM isobutylmethylxanthine (IBMX). Cells were incubated for 20 min at 37° C. Medium was then removed and replaced with fresh medium containing 0.5 mM IBMX, with or without 10 mM forskolin and various concentrations of drugs. Cells were incubated for 30 min at 37° C. Medium was then removed and cells sonicated in the wells in 250 mL 1M HCl and frozen for subsequent determination of cAMP content by RIA. Samples were thawed and diluted in cAMP RIA buffer before analysis of cAMP content using the commercially available assay kit from NEN/Dupont (Wilmington, Del.).

RNA blotting analysis: RNA blotting analysis was performed as previously described (Kong et al., 1994, *Neuroscience*; Delfs et al., in press). The human brain RNA blot was obtained from CLONTECH laboratories (Palo Alto, Calif.). Each lane contained 2 mg of poly A-selected mRNA. The blot was hybridized at 42° C. for 24 hours with random-primed 32P-labelled DNA (Prime-It, Stratagene) corresponding to a 1.6 kilobase (kB) fragment isolated after digestion with EcoRV and Xba I. This fragment includes the entire coding region of the human $\mu$ opioid receptor. The blots were washed at 65° C. in 2×SSC/0.5% SDS (0.3 M sodium chloride/0.03 M sodium citrate) for 20 minutes and in 0.2×SSC/0.2% SDS for 20 minutes before exposure to X-ray film for 5–7 days to detect signal.

B. Discussion

To characterize pharmacologically the cloned human $\mu$ receptor, Bell and Reisine transiently expressed the cDNA encoding this receptor in COS-7 cells as previously described (Yasuda et al., 1993; Kong et al., 1993). For comparative purposes, the rat $\mu$ receptor was also expressed in parallel experiments. The binding of [$^3$H]DAMGO to the human $\mu$ receptor was saturable and of high affinity. Scatchard analysis of the saturation experiments demonstrated that [$^3$H]DAMGO bound to the cloned human $\mu$ receptors with a KD of 1.0 nM and a $B_{max}$ of 232 fmol/mg. All data were best fit by single-site analysis. The inventors previously reported that [$^3$H]DAMGO bound to the cloned rat $\mu$ receptor with a KD of 0.57 nM and a $B_{max}$ of 444 fmol/mg protein. No specific radioligand binding was detectable in nontransfected or vector-transfected COS-7 cells.

To identify the pharmacological profile of the cloned human $\mu$ opioid receptor, a number of opioid ligands were tested for their abilities to inhibit [$^3$H]DAMGO binding to this receptor (Table 5).

TABLE 5

Binding potencies ($K_i$-nM) of ligands for the cloned human $\mu$ opioid receptor

| | $\mu$ RECEPTOR [$^3$H]DAMGO |
|---|---|
| Leu-enkephalin | 6.6 (1.2) |
| β-endorphin | 0.94 (0.06) |
| des-Tyr$^1$-β-endorphin | >1000 |
| (−)naloxone | 1.4 (0.4) |
| (+)naloxone | >1000 |
| (−)buprenorphine | 0.51 (0.09) |
| (+)buprenorphine | >1000 |
| levorphanol | 1.9 (0.6) |
| dextrorphan | >1000 |
| DAMGO | 1.4 (0.04) |
| morphine | 2.0 (0.6) |
| methadone | 5.6 (0.4) |
| codeine | 65 (13) |
| fentanyl | 1.9 (0.4) |
| sufentanil | 0.3 (0.08) |
| CTOP | 3.9 (0.4) |
| SMS 201-995 | 12 (3) |
| etorphine | 0.18 (0.04) |
| β-FNA | 0.29 (0.02) |
| nalorphine | 6.6 (1.2) |
| (±)bremazocine | 1.4 (0.3) |
| naltrexone | 1.5 (0.05) |
| diprenorphine | 0.18 (0.04) |

These ligands included a variety of compounds which have been previously characterized as $\mu$-selective including both peptide and non-peptide agonists and antagonists (Lutz and Pfister, 1992; Goldstein and Naidu, 1989; Raynor et al., 1994). As expected, most of these compounds bound to the cloned $\mu$ receptor with $K_i$ values in the low nM range (Table 8). The endogenous opioid peptides leu-enkephalin and β-endorphin bound potently to $\mu$ receptors whereas des-Tyr1-β-endorphin did not bind. The binding was stereoselective, being inhibited by (−)naloxone, (−)buprenorphine, and levorphanol but not by their respective isomers (+)naloxone, (+)buprenorphine, or dextrorphan. The $\mu$-selective compounds DAMGO, morphine, methadone, fentanyl, and sufentanil bound with affinities in the low nanomolar range, whereas the affinity of codeine was somewhat lower. The $\mu$-selective peptide antagonists CTOP and SMS 201-995 also bound with high affinities. Other relatively nonselective compounds tested were etorphine, β-FNA, nalorphine, (+)bremazocine, naltrexone, and diprenorphine, and all bound with high affinities. The δ-selective agonists DPDPE and D-Ala2 deltorphin II and the κ-selective compounds U-50,488 and U-69,593 did not bind to the human δ receptor at concentrations as high as 1 mM.

Comparisons of the affinities of all of these ligands for the human and rat $\mu$ receptors showed that most, but not all, of these drugs bind to these receptors with similar affinities. The affinities of morphine, methadone, and codeine were significantly higher for the human $\mu$ receptor than for the rat $\mu$ receptor (Table 6). All other drugs tested demonstrated indistinguishable affinities for the human and rat $\mu$ receptors, as exemplified in Table 5.

TABLE 6

Binding potencies ($K_i$-nM) of ligands for the cloned human and rat $\mu$ opioid receptor

| | [$^3$H]DAMGO | |
|---|---|---|
| | human | rat |
| morphine | 2.0 (0.6) | 22 (6.8) |
| methadone | 5.6 (0.4) | 19 (1.4) |
| codeine | 65 (13) | 168 (4) |
| fentanyl | 1.9 (0.4) | 1.3 (0.5) |
| etorphine | 0.18 (0.04) | 0.27 (0.6) |
| β-endorphin | 0.94 (0.06) | 1.7 (0.4) |
| (−)buprenorphine | 0.51 (0.09) | 0.42 (0.03) |

To investigate the association of the human $\mu$ receptor with guanine-nucleotide binding proteins (G proteins), the effects of nonhydrolyzable analogues of GTP and of pertussis toxin treatment of COS-7 cells transiently expressing the receptor on the binding of radiolabeled agonist to the receptor was also examined. Inclusion of 100 mM GTPgS in the [$^3$H]DAMGO binding assay decreased specific labelling of the human and rat $\mu$ receptors by 65+/−1.5% and by 55+/−7%, respectively. In addition, PTX-pretreatment of cells expressing the receptor substantially decreased [$^3$H]DAMGO labelling of human and rat $\mu$ receptors by 79+/−8% and by 42+/−5%, respectively. These results are consistent with coupling of both human and rat $\mu$ receptors to G-proteins.

The cloned rat $\mu$ receptor functionally couples to the inhibition of adenylyl cyclase (Chen et al., 1993). To determine whether the human $\mu$ receptor is also coupled to adenylyl cyclase, the effects of agonists to decrease cAMP accumulation in cells expressing the receptor were examined. Forskolin-stimulated cAMP accumulation was significantly reduced by leu-enkephalin and the effect was antagonized by (−)naloxone. The effect was stereoselective in that levorphanol also decreased cAMP accumulation, but dextrorphan was without effect.

A potential cellular mechanism of tolerance to opioids could be related to desensitization/down-regulation of specific receptors for these drugs. To determine whether agonist causes regulation of the $\mu$ receptor, cells expressing the human and rat $\mu$ receptors were exposed to 1 $\mu$M morphine for four hours. The inventors have previously demonstrated that the cloned mouse $\delta$ and $\kappa$ receptors undergo significant desensitization and/or downregulation after four hour exposures to high concentrations of selective agonists (Raynor et al., submitted; K. R. and T. R., unpublished observations). No significant changes in either radiolabeled agonist or antagonist binding were detectable. These results suggest that the $\mu$ receptor is not as readily regulated by agonist exposure as are the $\delta$ and $\kappa$ receptors.

RNA blotting using a probe against the full length coding region of the human $\mu$ opioid receptor detected multiple transcripts including a prominent mRNA of approximately 13.5 kB. This is of similar size to $\mu$ opioid receptor mRNA that the inventors and others have reported for the rat $\mu$ receptor mRNA (Fukuda et al., 1993; Delfs et al., 1994). Smaller size bands of 11, 4.3, and 2.8 were also detected. The highest levels of $\mu$ opioid receptor mRNA in human brain were detected in the hypothalamus, thalamus and subthalamic nuclei. High levels were also detected in the amygdala and caudate nucleus. Much lower levels were detected in the hippocampus, corpus callosum and substantia nigra. The 11 kB RNA was most abundant in the amygdala and subthalamic nucleus, whereas the 4.3 kB RNA was found in high abundance also in the corpus callosum.

In the present example, the pharmacological profile, regulation and cellular effector coupling of the cloned human $\mu$ receptor are examined. The characteristics of the receptor are very similar to those of the cloned rat $\mu$ receptor, consistent with the high degree of structural homology found between the receptors in these species. The pharmacological profile of the human $\mu$ receptor is similar to that which the inventors have previously reported for the rat $\mu$ receptor (Chen et al., 1993) with the notable exceptions of the affinities of several clinically-employed opioids such as morphine, methadone, and codeine. These compounds bound to the human $\mu$ receptor with higher affinities than to the rat $\mu$ receptor. The human and rat receptors are most divergent in the N-terminus, and these amino acid substitutions may contribute to the differing pharmacological properties of the rat and human $\mu$ receptors. Interestingly, the endogenous opioid peptides $\beta$-endorphin and leu-enkephalin bound with high affinities to the $\mu$ receptor, suggesting these peptides may be act at this receptor under physiological conditions. Likewise, as has been found for the rat $\mu$ receptor, the present findings indicate that opioid agents with abuse liabilities, such as morphine, fentanyl, and methadone, possess high affinities for the human $\mu$ receptor, whereas they demonstrate little or no affinity for the mouse $\delta$ or $\kappa$ receptors (Raynor et al., 1994). Development of analgesic agents which are $\kappa$- or $\delta$-selective may obviate this concern of $\mu$-selective analgesics, as well as other serious side effects including respiratory depression.

Another problem associated with the chronic use of opioids is the development of tolerance to these agents. While desensitization/downregulation of the opioid receptor (s) has been suggested as a potentially causal underlying mechanism of this phenomenon, a large body of evidence suggests that this is not the case for the $\mu$ opioid receptor with chronic in vivo exposures (reviewed in Zukin et al., 1993). These present results with the human $\mu$ opioid receptor expressed in cultured cells also suggest that downregulation at the receptor level does not readily occur, as it does for the cloned $\kappa$ and $\delta$ receptors (Raynor et al., submitted; K. R. and T. R., unpublished observations), and that other mechanisms must be involved in tolerance development to $\mu$-selective opioids.

In general, the distribution of the $\mu$ opioid receptor mRNA was similar in rat and human brain with highest levels detected in thalamic regions and lower levels in the striatum. The high levels of mRNA expression in the subthalamic region is unusual and suggests that this important relay nuclei involved in motor control may have high $\mu$ opioid receptor expression.

The RNA blotting revealed multiple $\mu$ receptor transcripts expressed in human brain. The size of the largest transcript (~13.5 kB) is similar to that reported for rat $\mu$ opioid receptor mRNA (Fukuda et al., 1993; Delfs et al., 1994). However, the smaller discrete RNA species detected in human brain differ from that detected in rat tissues. The identity of the multiple RNA species detected by RNA blot is not clear. They could represent the same RNA with different polyA+ tails or processing intermediaries. Pharmacological evidence suggests that subtypes of $\mu$ receptors are expressed in the nervous system. One intriguing possibility is that some of the distinct transcripts encode $\mu$ receptor subtypes.

The ability to study individually the pharmacological properties of the cloned opioid receptor subtypes will allow for identification of structural features of ligands which permit selective interactions. Identification of the pharmacological interactions of drugs with the individual opioid receptors could lead to the identification of therapeutic agents less burdened with the potential to produce undesirable side effects.

REFERENCES CITED

The references listed below as well as all references cited in the specification are incorporated herein by reference to the extent that they supplement, explain, provide a background for or teach methodology, techniques and/or compositions employed herein.

Adelman et al. (1983) *DNA* 2:183.
Akasu and Tokimasa (1992) *Can. J. Physiol. Pharmacol.* 70:S51–S55.
Akil et al. (1984) *Annu. Rev. Neurosci.* 7:223.
Alreja and Aghajanian (1993) *J. Neuroscience* 13:3525–3532.
Attali et al. (1991) *J. Neurochem.* 57:1803–1806.
Attali et al. (1989) *J. Neurochem.* 52:360.
Barrett and Vaught (1983) *Life Sci.* 33:2439.
Benovic et al. (1988) *Annu. Rev. Cell Biol.* 4:405–428.
Berg (1988) *Proc. Natl. Acad. Sci. U.S.A.* 85:99–102.
Berridge (1987) *Annu. Rev. Biochem.* 56:159–193.
Bertin et al. (1992) *J. Biol. Chem.* 267(12):8200.
Bero et al. (1988) *Mol. Pharmacol.* 34:614.
Bertolucci et al. *Neurosci. Abstr.* 18:L1368.
Blumberg et al. (1984) *Biochem. Pharmacol.* 33:933–940.
Bolivar et al. (1977) *Gene*, 2:95.
Boshart et al. (1985) *Cell* 41:521.
Bouvier et al. (1988) *Mol. Phannacol.* 33:133.
Bradford (1976) *Anal. Biochem.* 72:248–254.
Bradbury et al. (1976) *Nature* 260:165.
Breder et al. (1992). *J. Neurosci.* 12:3920.
Butt et al. (1990) *Biophys. J.* 58:1473.
Carlson et al. (1989) *J. Biol. Chem.* 264:13298–13305.
Chang et al. (1978) *Nature*, 375:615.
Chavkin et al. (1982) *Science* 215:413–415.
Chavkin (1988) In *The Opiate Receptors*, Pasternak, ed. (New Jersey: Humana Press), pp. 273–303.
Chen et al. (1993a) *Mol. Pharmacol.* 44:8–12.
Chen et al. (1993b) *Biochem. J.* 295:625–628.

Chen and Yu (1994) *J. Biol. Chem.* 269:7839–7842.
Cheng and Prusoff (1973) *Biochem. Pharmacol.* 22:3099–3108.
Childers (1993) In *Handbook of Experimental Pharmacology: Opioids I*, Herz ed. (Berlin: Springer-Verlag), 104:189–216.
Clark et al. (1989) *J. Pharmacol. Expt. Therapeut.* 251:461.
Clark et al. (1988) *Mol. Pharmacol.*, 34:308–317.
Collin and Cesselin (1991) *Clin. Neuropharmacol.* 14:465–488.
Collins et al. (1991) *Vitam. Horm.* 46:1–39.
Corbett et al. (1993). In *Handbook of Experimental Pharmacology: Opioids I*, Herz, ed. (Berlin: Springer-Verlag), 104:645–679.
Cotecchia et al. (1988) *Proc. Natl. Acad. Sci. USA* 85:7159.
Cotecchia et al. (1990) *Proc. Natl. Acad. Sci. USA* 87:2896.
Cox (1993) *Handb. Exp. Pharmacol. Sci.* 104:145.
Crea et al. (1978) *Proc. Natl. Acad. Sci. U.S.A,* 75:5765.
Cruciani et al. (1987) *J. Pharmacol. Exp. Ther.* 24215.
Danboldt et al. (1990) *Biochemistry* 29(28):6734.
Dascal et al. (1993) *Proc. Natl. Acad. Sci. USA* 90:6596–6600.
Delfs et al. (1994) *J. Comp. Neurol.* 343:2–24.
Devereux et al. (1984) *Nuc. Acid Res.* 12:387–395.
Di Chiara and North (1992) *Trends Pharmacol. Sci.* 13:185–193.
Dixon et al. (1988) *Cold Spring Harbor Symp. Quant. Biol.* 53:487–497.
Doerner et al. (1988) *J. Neuroscience* 8:4069–4078.
Dohlman et al. (1991) *Annu. Rev. Biochem.* 60:653–688.
Dohlman (1987) *Biochemistry* 26:2657.
Dohlman (1991) *Annu. Rev. Biochem.* 60:166–170; 174–s176.
Drake et al. (1989) *Science* 243:1586.
Durbin and Carlson (1992) *J. Crystal Growth* 122:71.
Edstrom et al. (1990) *Biophys. J.* 58:1437.
Evans et al. (1992) *Science* 258:1952–1955.
Evans and Hollenberg (1988) *Cell* 52:1–3.
Ferruti and Tanzi, (1986) *Cris. Rev. Ther. Drug Carrier Syst.* 2:117.
Fiers et al. (1978) *Nature* 273:113.
Frey and Kebabian (1984) *Endocrinology* 115:1797.
Frielle et al. (1988) *Proc. Natl. Acad. Sci. USA* 85:9484.
Fukuda et al. (1993) *FEBS Lett.* 327:311–314.
Gabizon et al. (1990) *Cancer Res.* 50:6371–6378
Gioannini et al. (1989) *J. Mol. Recogn.* 2:44.
Goeddel et al. (1979) *Nature*, 281:544.
Goeddel et al. (1980) *Nucleic Acids Res.*, 8:4057.
Goldstein (1987) *Trends Pharmacol. Sci.* 8:456–459.
Goldstein and Naidu (1989) *Mol. Pharmacol.* 36:265–272.
Graham and Van Der Eb (1973) *Virology* 52:456.
Gransch et al. (1988) *J. Biol. Chem.* 263:5853.
Gulya et al. (1986) *Life Sci.* 38:2221.
Gurdon and Wickens (1983) *Meth. Enzym.* 101:370–386.
Guitart and Nestler (1993) *Neurochemical Res.* 18:5–13.
Hansma et al. (1992) *Science* 256:1180.
Harlow and Lane (1988) *Antibodies: "A Laboratory Manual,"* Cold Spring Harbor Laboratory.
Harris and Williams (1991) *J. Neuroscience* 11:2574–2581.
Henderson et al. (1992) *Science* 257:1944.
Herz ed. (1993) *Opioids I, Handbook of Experimental Therapeutics* 104 Springer-Verlag, New York.
Hess et al. (1968) *J. Adv. Enzyme Reg.* 7:149.
Hitzeman et al. (1980) *J. Biol. Chem.* 255:2073.
Hoh et al (1991) *Science* 253:1405.
Holland et al. (1978) *Biochemistry* 17:4900.
Horstman et al. (1990) *J. Biol. Chem.* 265:21590.
Hsia et al. (1984) *J. Biol. Chem.* 259:1086.
Hughes et al. (1975) *Nature* 258:577.
Itakura et al. (1977) *Science* 198:1056.
Itzhak and Pasternak (1987) *Life Sci.* 40:307.
Jaffe and Martin (1990) in *The Pharmacological Basis of Therapeutics*, 8th Ed. Gilman, Rall, Nies, and Taylor, eds. Pergamon Press, New York, 485–573.
Johnson et al. (1990) *Mol. Pharm.*, 38:289.
Johnson and Fleming (1989) *Pharmacological Rev.* 41:435–488.
Jones (1977) *Genetics* 85:12.
Kanaho et al. (1984) *J. Biol. Chem.* 259:7378.
Kawasaki et al. (1990) *J. Med. Chem.* 33:1874–1879.
Kennelly et al. (1991) *J. Biol. Chem.* 266:15555.
Kieffer et al. (1992) *Proc. Natl. Acad. Sci. USA* 89:12048–12052.
King et al. (1990) *Science* 250:121.
Kingsman et al. (1979) *Gene* 7:141.
Klug and Rhodes (1987) *Trends Biochem. Sci.* 12:464–469.
Kluxen et al. (1992) *Proc. Natl. Acad. Sci. USA* 89:4618.
Kobilka et al. (1987) *J. Biol. Chem.* 262:7321.
Kobilka et al. (1988) *Science* 240:1310.
Kong et al. (1993) *J. Biol. Chem.* 268:23055–23058.
Kong et al. (1994) *Neuroscience* 59:175–184.
Koob et al. (1992) *Trends Neurosci.* 15:186.
Koshi and Klee (1981) *Proc. Natl. Acad. Sci. USA* 78:4185.
Kozasa et al. (1988) *Proc. Natl. Acad. Sci USA* 85:2081.
Kruse and Patterson, eds. (1973) *Tissue Culture*, Academic Press.
Kubo et al. (1993) *Nature* 364:802–806.
Kyte and Doolittle (1982) *J. Mol. Biol.* 157:105.
Lal et al. (1993) *Am. J. Physiol.* in press.
Lal, R. and L. Yu (1993) *Proc. Natl. Acad. Sci. USA,* 90:7280.
Lane et al. (1992) *Proc. Natl. Acad. Sci. USA* 89:11234–11238.
Law et al. (1991) *J. Biol. Chem.* 266:17885–17897.
Lester et al. (1993) *Brain Res.* 621:106–110.
Li et al. (1993) *Biochemical J.* 295:629–633.
Lippman et al. (1992) *Gene* 117:249–254.
Loh et al. (1988) *Synapse* 2:457–462.
Loh et al. (1990) *Annu. Rev. Pharmacol. Toxicol.* 30:123.
Lomasney et al. (1990) *Proc. Natl. Acad. Sci. USA* 87:5094.
Louie et al. (1990) *J. Pharmacol. Exp. Ther.* 253:401–407.
Lutz et al. (1992) *J. Receptor Res.* 12:267–286.
MacNicol and Schulman (1992a) *J. Biol. Chem.* 267:12197–12201.
MacNicol and Schulman (1992b) *FEBS Lett.* 304:237–240.
Magnan et al. (1982) *Naunyn-Schmiedebergs Arch. Pharmacol.* 319:197.
Mansour et al. (1987) *J. Neuroscience* 7:2445–2464.
Mansour et al. (1988) *Trends Neurosci.* 11:308–314.
Marullo et al. (1988) *Proc. Natl. Acad. Sci. USA* 85:7551.
McGonigle et al. (1988) in *PROPHET Public Procedures Notebook* Bolt, Berabek and Newman, Inc. Cambridge, Mass., 215–218.
Meng et al. (1993) *Proc. Natl. Acad. Sci. USA* 90:9954–9958.
Messing et al. (1981) In *Third Cleveland Symposium on Macromolecules and Recombinant DNA*, Walton, ed. (Elsevier:Amsterdam).
Mestek et al. submitted for publication.
Meryerhof et al. (1991) *DNA Cell Biol.* 10:689.
Miller et al. (1985) *IAMB J.* 4:1609–1614.
Minami et al. (1993) *FEBS Lett.* 329:291–295.
Miyake et al. (1989) *Proc. Natl. Acad. Sci. USA* 86:3419–3422.

Mumby et al. (1986) *Proc. Natl. Acad. Sci. USA* 83:265–269.
Munson (1983) *Meth. Enzymol.* 92:543–576.
Nathans et al. (1986 A) *Science* 232:193.
Nathans et al. (1986 B) *Science* 232:203
Nestler et al. (1993) *Neuron* 11:995–1006.
Nishimura et al. (1984) *Mol. Pharmacol.* 25:29.
Nock et al. (1988) *Eur. J. Pharmacol.* 154:27–34.
North (1986) *Trends Neurosci.* 9:114–117.
North et al. (1987) *Proc. Natl. Acad. Sci. USA* 84:5487–5491.
North (1993) In *Handbook of Experimental Pharmacology: Opioids I*, Herz, ed. (Berlin: Springer-Verlag), 104:773–797.
Okayama et al. (1983) *Mol. Cell Biol.* 3:280.
Olson, G. A. et al. (1989) *Peptides* 10:1253.
Ott, S. et al. (1988) *J. Biol. Chem.* 263:10524.
Parker, E. and E. M. Ross (1991) *J. of Biol. Chem.* 266:15.
Pasternak (1988) *The Opiate Receptors* (New Jersey: Humana Press).
Pasternak (1993) *Clin. Neuropharmacol.* 16:1–18.
Payette et al. (1990) *FEBS Lett.* 266:21.
Payre, F. and A. Vincent (1988) *FEBS Lett.* 234:245–250.
Perry and McGonigle (1988) In *PROPHET Public Procedures Notebook* Bolt, Berabek and Newman, Inc. Cambridge, Mass., 187–192.
Pert, C. G. et al. (1973) *Science* 179:1011.
Pert, C. B. et al. (1974) *Mol. Pharmacol.* 10:868.
Pfeiffer et al. (1986) *Science* 223:774.
Pfeiffer et al. (1982) *Brain Res.* 248:87–96.
Pilapil et al. (1987) *Brain Res. Bull.* 19:611–615.
Porreca et al. (1984) *J. Pharmacol. Exp. Ther.* 230:341–348.
Puttfarcken et al. (1988) *Mol. Pharmacol.* 33:520.
Ranade (1989) *J. Clin. Pharmacol.* 29:685–694
Raynor et al. (1994) *Mol. Pharmacol.* 45:330–334.
Regan et al. (1988) *Proc. Natl. Acad. Sci. USA* 85:6301.
Sambrook et al. (1989) *Molecular Cloning: A Laboratory Manual* (Cold Spring Harbor Laboratory Press, Cold Spring Harbor, N.Y.).
Schmidhammer et al. (1990) *Prog. Clin. Biol. Res.* 328:37.
Schulman (1984) *J. Cell Biol.* 99:11–19.
Schulman and Hanson (1993) *Neurochemical Res.* 18:65–77.
Seeburg (1982) *DNA* 1:239.
Sharma et al. (1975) *Proc. Natl. Acad. Sci. USA* 72:590.
Shearman et al. (1989) *Pharmacol. Rev.* 41:211–237.
Shook et al. (1990) *Am. Rev. Respir. Dis.* 142:895.
Siebwenlist et al. (1980) *Cell*, 20:269.
Simon (1991) *Medicinal Res. Rev.* 11:357.
Snutch et al. (1990) *Proc. Natl. Acad. Sci. USA* 87:3391.
Stinchcomb et al. (1979) *Nature*, 282:39.
Stratford-Perricaudet et al. (1992).
Strotchman and Simon (1991).
Sumikawa and Miledi (1989) *Mol. Brain Res.* 5:183.
Thompson et al. (1993) *Neuron* 11:903–913.
Thomsen et al. (1984) *PNAS* 81:659.
Tschemper et al. (1980) *Gene* 10:157.
Unterwald et al. (1991) *Brain Res.* 562:57–65.
Unterwald et al. (1987) *Eur. J. Pharmacol.* 133:275.
Vaughn and Taylor (1989) *Biochim. Biophys. Acta* 999:135–146.
Waldmann et al. (1990) *Biochemistry* 29:1679–1684.
Wang et al. (1993) *Proc. Natl. Acad. USA* 90:10230–10234.
Wang et al. (1994) *FEBS Lett.* 338:217–222.
Ward et al. (1985) *Eur. J. Pharmacol* 107:323.
Weiner et al. (1990) *Proc. Natl. Acad. Sci. USA* 87:7050–7054.
Weisenhorn et al. (1990) *Biophys. J.* 58:1251.
Wimpey and Chavkin (1991) *Neuron* 6:281–289.
Wood (1988) *Peptides* 9(Suppl 1):49–55.
Wood and Iyengar (1988) In *The Opiate Receptors* Pasternak, ed. (New Jersey: Humana Press), pp. 307–356.
Xie et al. (1992) *Proc. Natl. Acad. Sci. USA* 89:4124.
Yaksh (1981) *Pain* 11:293–346.
Yamada et al. (1992) *Proc. Natl. Acad. Sci. USA* 89:251.
Yamakawa et al. (1992) *Brain Res.* 597:220–226.
Yasuda et al. (1993) *Proc. Natl. Acad. Sci. USA* 90:6736–6740.
Yasuda et al. (1992) *J. Biol Chem.* 267:20422.
Yokota et al. (1992) *IAMB J.* 11:3585.
Yu et al. (1986) *J. Biol. Chem.* 261:1065.
Zukin et al. (1988) *Proc. Natl. Acad. Sci. USA* 85:4061.
Zukin et al. (1993) in *Opioids I, Handbook of Experimental Therapeutics* Herz, ed., Springer-Verlag, New York, 104/I:107–123.

What is claimed is:

1. An isolated nucleic acid molecule that comprises a segment of at least 35 contiguous nucleotides of SEQ ID NO:7, wherein said segment comprises at least the guanine nucleotide at position 151 of SEQ ID NO:7.

2. The nucleic acid molecule of claim 1, comprising a segment of at least 40 contiguous nucleotides of SEQ ID NO:7, wherein said segment comprises at least the guanine nucleotide at position 151 of SEQ ID NO:7.

3. The nucleic acid molecule of claim 2, comprising a segment of at least 45 contiguous nucleotides of SEQ ID NO:7, wherein said segment comprises at least the guanine nucleotide at position 151 of SEQ ID NO:7.

4. The nucleic acid molecule of claim 3, comprising a segment of at least 50 contiguous nucleotides of SEQ ID NO:7, wherein said segment comprises at least the guanine nucleotide at position 151 of SEQ ID NO:7.

5. The nucleic acid molecule of claim 4, comprising a segment of at least 55 contiguous nucleotides of SEQ ID NO:7, wherein said segment comprises at least the guanine nucleotide at position 151 of SEQ ID NO:7.

6. An isolated nucleic acid molecule that encodes a polypeptide comprising the amino acid sequence of SEQ ID NO:8.

7. The nucleic acid molecule of claim 6, wherein said nucleic acid molecule is DNA.

8. The nucleic acid molecule of claim 6, wherein said nucleic acid molecule is operably linked to a promoter.

9. The nucleic acid molecule of claim 8, wherein said nucleic acid molecule is operably linked to a prokaryotic promoter.

10. The nucleic acid molecule of claim 8, wherein said nucleic acid molecule is operably linked to an eukaryotic promoter.

11. The nucleic acid molecule of claim 6, comprising a nucleotide sequence of at least 35 contiguous nucleotides of SEQ ID NO:7 that includes at least the guanine nucleotide corresponding to guanine nucleotide 151 of SEQ ID NO: 7.

12. The nucleic acid molecule of claim 11, comprising a nucleotide sequence of at least 40 contiguous nucleotides of SEQ ID NO:7 that includes at least the guanine nucleotide corresponding to guanine nucleotide 151 of SEQ ID NO:7.

13. The nucleic acid molecule of claim 12, comprising a nucleotide sequence of at least 45 contiguous nucleotides of SEQ ID NO:7 that includes at least the guanine nucleotide corresponding to guanine nucleotide 151 of SEQ ID NO:7.

14. The nucleic acid molecule of claim 13, comprising a nucleotide sequence of at least 50 contiguous nucleotides of SEQ ID NO:7 that includes at least the guanine nucleotide corresponding to guanine nucleotide 151 of SEQ ID NO:7.

15. The nucleic acid molecule of claim 14, comprising a nucleotide sequence of at least 75 contiguous nucleotides of SEQ ID NO:7 that includes at least the guanine nucleotide corresponding to guanine nucleotide 151 of SEQ ID NO:7.

16. The nucleic acid molecule of claim 15, comprising a nucleotide sequence of at least 100 contiguous nucleotides of SEQ ID NO:7 that includes at least the guanine nucleotide corresponding to guanine nucleotide 151 of SEQ ID NO:7.

17. The nucleic acid molecule of claim 16, comprising the nucleotide sequence of SEQ ID NO:7.

18. A vector comprising a nucleic acid molecule that encodes the amino acid sequence of SEQ ID NO:8.

19. A vector comprising a nucleic acid molecule that encodes a nucleotide sequence of at least 40 contiguous nucleotides of SEQ ID NO:7 that includes at least the guanine residue corresponding to guanine residue 151 of SEQ ID NO:7.

20. The vector of claim 18 or 19, wherein said nucleic acid molecule is operatively linked to a promoter.

21. The vector of claim 20, wherein said nucleic acid molecule is operatively linked to a prokaryotic promoter.

22. The vector of claim 20, wherein said nucleic acid molecule is operatively linked to an eukaryotic promoter.

23. A host cell transformed with a nucleic acid molecule that encodes a polypeptide comprising the amino acid sequence of SEQ ID NO:8.

24. The host cell of claim 23, wherein said nucleic acid molecule comprises the nucleic acid sequence of SEQ ID NO:7.

25. The host cell of claim 23, wherein said host cell is an eukaryotic cell.

26. The host cell of claim 25, wherein said eukaryotic host cell is a COS cell.

27. The host cell of claim 23, wherein said host cell is a prokaryotic cell.

28. The host cell of claim 27, wherein said prokaryotic host cell is *E. coli.*

29. The host cell of claim 23, wherein said host cell is cultured under conditions that permit the expression of said nucleic acid molecule to produce the encoded polypeptide.

30. The host cell of claim 23, comprising the vector of claim 18 or claim 19.

31. A method of expressing a polypeptide in a host cell comprising:
  (a) culturing a host cell that comprises a nucleic acid molecule that encodes a polypeptide comprising the amino acid sequence of SEQ ID NO:8 under conditions sufficient for expression of the polypeptide; and
  (b) expressing said polypeptide in said cell.

32. The method of claim 31, wherein said nucleic acid molecule comprises a segment identical to at least 35 contiguous nucleotides from SEQ ID NO:7.

33. The method of claim 32, wherein said nucleic acid molecule comprises a segment identical to at least 40 contiguous nucleotides from SEQ ID NO:7.

34. The method of claim 33, wherein said nucleic acid molecule comprises a segment identical to at least 45 contiguous nucleotides from SEQ ID NO:7.

35. The method of claim 34, wherein said nucleic acid molecule comprises a segment identical to at least 50 contiguous nucleotides from SEQ ID NO:7.

36. The method of claim 35, wherein said nucleic acid molecule comprises the sequence of SEQ ID NO:7.

37. A method of expressing a polypeptide in a host cell comprising:
  (a) culturing a host cell that comprises a nucleotide sequence comprising SEQ ID NO: 16 and encoding a polypeptide comprising the amino acid sequence of SEQ ID NO:17 under conditions sufficient for expression of the polypeptide; and
  (b) expressing said polypeptide in said cell.

* * * * *

UNITED STATES PATENT AND TRADEMARK OFFICE
CERTIFICATE OF CORRECTION

PATENT NO.  : 6,103,492
DATED       : August 15, 2000
INVENTOR(S) : Lei Yu

It is certified that error appears in the above-identified patent and that said Letters Patent is hereby corrected as shown below:

Column 62,
Line 59, delete "151" and insert therefor -- 389 --.

Column 111,
Claim 1,
Line 26, delete "151" and insert therefor -- 389 --.

Claim 2,
Line 30, delete "151" and insert therefor -- 389 --.

Claim 3,
Line 34, delete "151" and insert therefor -- 389 --.

Claim 4,
Line 38, delete "151" and insert therefor -- 389 --.

Claim 5,
Line 42, delete "151" and insert therefor -- 389 --.

Claim 11,
Line 59, delete "151" and insert therefor -- 389 --.

Claim 12,
Line 63, delete "151" and insert therefor -- 389 --.

Claim 13,
Line 67, delete "151" and insert therefor -- 389 --.

Column 112,
Claim 14,
Line 25, delete "151" and insert therefor -- 389 --.

Claim 15,
Line 29, delete "151" and insert therefor -- 389 --.

UNITED STATES PATENT AND TRADEMARK OFFICE
CERTIFICATE OF CORRECTION

PATENT NO. : 6,103,492
DATED : August 15, 2000
INVENTOR(S) : Lei Yu

It is certified that error appears in the above-identified patent and that said Letters Patent is hereby corrected as shown below:

Column 112, contd.
Claim 16,
Line 33, delete "151" and insert therefor -- 389 --.

Claim 19,
Line 41, delete "151" and insert therefor -- 389 --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 1618 base pairs
      (B) TYPE: nucleic acid
      (C) STRANDEDNESS: single
      (D) TOPOLOGY: linear (ii) MOLECULE TYPE: DNA (cDNA)

(ix) FEATURE:
      (A) NAME/KEY: CDS
      (B) LOCATION: 214..1410

(xi) SEQUENCE DESCRIPTION: SEQ ID NO:1:

```
CGTGGAAGGG GGCTACAAGC AGAGGAGAAT ATCAGACGCT CAGACGTTCC CTTCTGCCTG      60

CCGCTCTTCT CTGGTTCCAC TAGGGCTGGT CCATGTAAGA ATCTGACGGA GCCTAGGGCA     120

GCTGTGAGAG GAAGAGGCTG GGGCGCGTGG AACCCGAAAA GTCTGAGTGC TCTCAGTTAC     180

AGCCTACCTA GTCCGCAGCA GGCCTTCAGC ACC ATG GAC AGC AGC ACC GGC CCA     234
                                    Met Asp Ser Ser Thr Gly Pro
                                     1               5

GGG AAC ACC AGC GAC TGC TCA GAC CCC TTA GCT CAG GCA AGT TGC TCC      282
Gly Asn Thr Ser Asp Cys Ser Asp Pro Leu Ala Gln Ala Ser Cys Ser
         10              15              20

CCA GCA CCT GGC TCC TGG CTC AAC TTG TCC CAC GTT GAT GGC AAC CAG      330
Pro Ala Pro Gly Ser Trp Leu Asn Leu Ser His Val Asp Gly Asn Gln
     25              30              35

TCC GAT CCA TGC GGT CTG AAC CGC ACC GGG CTT GGC GGG AAC GAC AGC      378
Ser Asp Pro Cys Gly Leu Asn Arg Thr Gly Leu Gly Gly Asn Asp Ser
 40              45              50                          55

CTG TGC CCT CAG ACC GGC AGC CCT TCC ATG GTC ACA GCC ATT ACC ATC      426
Leu Cys Pro Gln Thr Gly Ser Pro Ser Met Val Thr Ala Ile Thr Ile
                 60              65              70

ATG GCC CTC TAC TCT ATC GTG TGT GTA GTG GGC CTC TTC GGA AAC TTC      474
Met Ala Leu Tyr Ser Ile Val Cys Val Val Gly Leu Phe Gly Asn Phe
             75              80              85

CTG GTC ATG TAT GTG ATT GTA AGA TAC ACC AAA ATG AAG ACT GCC ACC      522
Leu Val Met Tyr Val Ile Val Arg Tyr Thr Lys Met Lys Thr Ala Thr
         90              95             100

AAC ATC TAC ATT TTC AAC CTT GCT CTG GCA GAC GCC TTA GCG ACC AGT      570
Asn Ile Tyr Ile Phe Asn Leu Ala Leu Ala Asp Ala Leu Ala Thr Ser
105             110             115

ACA CTG CCC TTT CAG AGT GTC AAC TAC CTG ATG GGA ACA TGG CCC TTC      618
Thr Leu Pro Phe Gln Ser Val Asn Tyr Leu Met Gly Thr Trp Pro Phe
120             125             130             135

GGA ACC ATC CTC TGC AAG ATC GTG ATC TCA ATA GAT TAC TAC AAC ATG      666
Gly Thr Ile Leu Cys Lys Ile Val Ile Ser Ile Asp Tyr Tyr Asn Met
             140             145             150

TTC ACC AGC ATA TTC ACC CTC TGC ACC ATG AGC GTG GAC CGC TAC ATT      714
Phe Thr Ser Ile Phe Thr Leu Cys Thr Met Ser Val Asp Arg Tyr Ile
         155             160             165

GCT GTC TGC CAC CCA GTC AAA GCC CTG GAT TTC CGT ACC CCC CGA AAT      762
Ala Val Cys His Pro Val Lys Ala Leu Asp Phe Arg Thr Pro Arg Asn
     170             175             180

GCC AAA ATC GTC AAC GTC TGC AAC TGG ATC CTC TCT TCT GCC ATC GGT      810
Ala Lys Ile Val Asn Val Cys Asn Trp Ile Leu Ser Ser Ala Ile Gly
185             190             195

CTG CCT GTA ATG TTC ATG GCA ACC ACA AAA TAC AGG CAG GGG TCC ATA      858
Leu Pro Val Met Phe Met Ala Thr Thr Lys Tyr Arg Gln Gly Ser Ile
200             205             210             215

GAT TGC ACC CTC ACG TTC TCC CAC CCA ACC TGG TAC TGG GAG AAC CTG      906
Asp Cys Thr Leu Thr Phe Ser His Pro Thr Trp Tyr Trp Glu Asn Leu
             220             225             230

CTC AAA ATC TGT GTC TTT ATC TTC GCT TTC ATC ATG CCG ATC CTC ATC      954
Leu Lys Ile Cys Val Phe Ile Phe Ala Phe Ile Met Pro Ile Leu Ile
         235             240             245

ATC ACT GTG TGT TAC GGC CTG ATG ATC TTA CGA CTC AAG AGC GTT CGC     1002
Ile Thr Val Cys Tyr Gly Leu Met Ile Leu Arg Leu Lys Ser Val Arg
     250             255             260

ATG CTA TCG GGC TCC AAA GAA AAG GAC AGG AAT CTG CGC AGG ATC ACC     1050
Met Leu Ser Gly Ser Lys Glu Lys Asp Arg Asn Leu Arg Arg Ile Thr
265             270             275

CGG ATG GTG CTG GTG GTC GTG GCT GTA TTT ATC GTC TGC TGG ACC CCC     1098
```

```
Arg Met Val Leu Val Val Ala Val Phe Ile Val Cys Trp Thr Pro
280                 285                 290                 295

ATC CAC ATC TAC GTC ATC ATC AAA GCG CTG ATC ACG ATT CCA GAA ACC      1146
Ile His Ile Tyr Val Ile Ile Lys Ala Leu Ile Thr Ile Pro Glu Thr
            300                 305                 310

ACA TTT CAG ACC GTT TCC TGG CAC TTC TGC ATT GCT TTG GGT TAC ACG      1194
Thr Phe Gln Thr Val Ser Trp His Phe Cys Ile Ala Leu Gly Tyr Thr
        315                 320                 325

AAC AGC TGC CTG AAT CCA GTT CTT TAC GCC TTC CTG GAT GAA AAC TTC      1242
Asn Ser Cys Leu Asn Pro Val Leu Tyr Ala Phe Leu Asp Glu Asn Phe
        330                 335                 340

AAG CGA TGC TTC AGA GAG TTC TGC ATC CCA ACC TCG TCC ACG ATC GAA      1290
Lys Arg Cys Phe Arg Glu Phe Cys Ile Pro Thr Ser Ser Thr Ile Glu
345                 350                 355

CAG CAA AAC TCC ACT CGA GTC CGT CAG AAC ACT AGG GAA CAT CCC TCC      1338
Gln Gln Asn Ser Thr Arg Val Arg Gln Asn Thr Arg Glu His Pro Ser
360                 365                 370                 375

ACG GCT AAT ACA GTG GAT CGA ACT AAC CAC CAG CTA GAA AAT CTG GAG      1386
Thr Ala Asn Thr Val Asp Arg Thr Asn His Gln Leu Glu Asn Leu Glu
                380                 385                 390

GCA GAA ACT GCT CCA TTG CCC TAACTGGGTC TCACACCATC CAGACCCTCG         1437
Ala Glu Thr Ala Pro Leu Pro
                395

CTAAGCTTAG AGGCCGCCAT CTACGTGGAA TCAGGTTGCT GTCAGGGTGT GTGGGAGGCT    1497

CTGGTTTCCT GAGAAACCAT CTGATCCTGC ATTCAAAGTC ATTCCTCTCT GGCTACTTCA    1557

CTCTGCACAT GAGAGATGCT CAGACTGATC AAGACCAGAA GAAAGAAGAG ACTACCGGAC    1617

A                                                                    1618

(2) INFORMATION FOR SEQ ID NO:2:

(i) SEQUENCE CHARACTERISTICS:
        (A) LENGTH: 398 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Ser Ser Thr Gly Pro Gly Asn Thr Ser Asp Cys Ser Asp Pro
1               5                   10                  15

Leu Ala Gln Ala Ser Cys Ser Pro Ala Pro Gly Ser Trp Leu Asn Leu
                20                  25                  30

Ser His Val Asp Gly Asn Gln Ser Asp Pro Cys Gly Leu Asn Arg Thr
            35                  40                  45

Gly Leu Gly Gly Asn Asp Ser Leu Cys Pro Gln Thr Gly Ser Pro Ser
        50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
                100                 105                 110

Ala Asp Ala Leu Ala Thr Ser Thr Leu Pro Phe Gln Ser Val Asn Tyr
            115                 120                 125

Leu Met Gly Thr Trp Pro Phe Gly Thr Ile Leu Cys Lys Ile Val Ile
        130                 135                 140

Ser Ile Asp Tyr Tyr Asn Met Phe Thr Ser Ile Phe Thr Leu Cys Thr
```

```
145                 150                 155                 160
Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
            195                 200                 205

Lys Tyr Arg Gln Gly Ser Ile Asp Cys Thr Leu Thr Phe Ser His Pro
        210                 215                 220

Thr Trp Tyr Trp Glu Asn Leu Leu Lys Ile Cys Val Phe Ile Phe Ala
225                 230                 235                 240

Phe Ile Met Pro Ile Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Thr Arg Val Arg Gln
        355                 360                 365

Asn Thr Arg Glu His Pro Ser Thr Ala Asn Thr Val Asp Arg Thr Asn
    370                 375                 380

His Gln Leu Glu Asn Leu Glu Ala Glu Thr Ala Pro Leu Pro
385                 390                 395

(2) INFORMATION FOR SEQ ID NO:3:

(i) SEQUENCE CHARACTERISTICS:
        (A) LENGTH: 1618 base pairs
        (B) TYPE: nucleic acid
        (C) STRANDEDNESS: single
        (D) TOPOLOGY: linear (ii) MOLECULE TYPE: DNA (cDNA)

(ix) FEATURE:
        (A) NAME/KEY: CDS
        (B) LOCATION: 339..1235

(xi) SEQUENCE DESCRIPTION: SEQ ID NO:3:

CGTGGAAGGG GGCTACAAGC AGAGGAGAAT ATCAGACGCT CAGACGTTCC CTTCTGCCTG      60

CCGCTCTTCT CTGGTTCCAC TAGGGCTGGT CCATGTAAGA ATCTGACGGA GCCTAGGGCA     120

GCTGTGAGAG GAAGAGGCTG GGGCGCGTGG AACCCGAAAA GTCTGAGTGC TCTCAGTTAC     180

AGCCTACCTA GTCCGCAGCA GGCCTTCAGC ACCATGGACA GCAGCACCGG CCCAGGGAAC     240

ACCAGCGACT GCTCAGACCC CTTAGCTCAG GCAAGTTGCT CCCCAGCACC TGGCTCCTGG     300

CTCAACTTGT CCCACGTTGA TGGCAACCAG TCCGATCC ATG CGG TCT GAA CCG         353
                                          Met Arg Ser Glu Pro
                                            1               5

CAC CGG GCT TGG CGG GAA CGA CAG CCT GTG CCC TCA GAC CGG CAG CCC      401
```

```
                His Arg Ala Trp Arg Glu Arg Gln Pro Val Pro Ser Asp Arg Gln Pro
                         10                  15                  20

TTC CAT GGT CAC AGC CAT TAC CAT CAT GGC CCT CTA CTC TAT CGT GTG          449
Phe His Gly His Ser His Tyr His His Gly Pro Leu Leu Tyr Arg Val
             25                  30                  35

TGT AGT GGG CCT CTT CGG AAA CTT CCT GGT CAT GTA TGT GAT TGT AAG          497
Cys Ser Gly Pro Leu Arg Lys Leu Pro Gly His Val Cys Asp Cys Lys
         40                  45                  50

ATA CAC CAA AAT GAA GAC TGC CAC CAA CAT CTA CAT TTT CAA CCT TGC          545
Ile His Gln Asn Glu Asp Cys His Gln His Leu His Phe Gln Pro Cys
 55                  60                  65

TCT GGA AGA CGC CTT AGC GAC CAG TAC ACT GCC CTT TCA GAG TGT CAA          593
Ser Gly Arg Arg Leu Ser Asp Gln Tyr Thr Ala Leu Ser Glu Cys Gln
 70                  75                  80                  85

CTA CCT GAT GGG AAC ATG GCC CTT CGG AAC CAT CCT CTG CAA GAT CGT          641
Leu Pro Asp Gly Asn Met Ala Leu Arg Asn His Pro Leu Gln Asp Arg
                 90                  95                 100

GAT CTC AAT AGA TTA CTA CAA CAT GTT CAC CAG CAT ATT CAC CCT CTG          689
Asp Leu Asn Arg Leu Leu Gln His Val His Gln His Ile His Pro Leu
             105                 110                 115

CAC CAT GAG CGT GGA CCG CTA CAT TGC TGT CTG CCA CCC AGT CAA AGC          737
His His Glu Arg Gly Pro Leu His Cys Cys Leu Pro Pro Ser Gln Ser
         120                 125                 130

CCT GGA TTT CCG TAC CCC CCG AAA TGC CAA AAT CGT CAA CGT CTG CAA          785
Pro Gly Phe Pro Tyr Pro Pro Lys Cys Gln Asn Arg Gln Arg Leu Gln
135                 140                 145

CTG GAT CCT CTC TTC TGC CAT CGG TCT GCC TGT AAT GTT CAT GGC AAC          833
Leu Asp Pro Leu Phe Cys His Arg Ser Ala Cys Asn Val His Gly Asn
150                 155                 160                 165

CAC AAA ATA CAG GCA GGG GTC CAT AGA TTG CAC CCT CAC GTT CTC CCA          881
His Lys Ile Gln Ala Gly Val His Arg Leu His Pro His Val Leu Pro
                 170                 175                 180

CCC AAC CTG GTA CTG GGA GAA CCT GCT CAA AAT CTG TGT CTT TAT CTT          929
Pro Asn Leu Val Leu Gly Glu Pro Ala Gln Asn Leu Cys Leu Tyr Leu
             185                 190                 195

CGC TTT CAT CAT GCC GAT CCT CAT CAT CAC TGT GTG TTA CGG CCT GAT          977
Arg Phe His His Ala Asp Pro His His His Cys Val Leu Arg Pro Asp
         200                 205                 210

GAT CTT ACG ACT CAA GAG CGT TCG CAT GCT ATC GGG CTC CAA AGA AAA         1025
Asp Leu Thr Thr Gln Glu Arg Ser His Ala Ile Gly Leu Gln Arg Lys
     215                 220                 225

GGA CAG GAA TCT GCG CAG GAT CAC CCG GAT GGT GCT GGT GGT CGT GGC         1073
Gly Gln Glu Ser Ala Gln Asp His Pro Asp Gly Ala Gly Gly Arg Gly
230                 235                 240                 245

TGT ATT TAT CGT CTG CTG GAC CCC CAT CCA CAT CTA CGT CAT CAT CAA         1121
Cys Ile Tyr Arg Leu Leu Asp Pro His Pro His Leu Arg His His Gln
                 250                 255                 260

AGC GCT GAT CAC GAT TCC AGA AAC CAC ATT TCA GAC CGT TTC CTG GCA         1169
Ser Ala Asp His Asp Ser Arg Asn His Ile Ser Asp Arg Phe Leu Ala
             265                 270                 275

CTT CTG CAT TGC TTT GGG TTA CAC GAA CAG CTG CCT GAA TCC AGT TCT         1217
Leu Leu His Cys Phe Gly Leu His Glu Gln Leu Pro Glu Ser Ser Ser
         280                 285                 290

TTA CGC CTT CCT GGA TGAAACTTC AAGCGATGCT TCAGAGAGTT CTGCATCCCA         1272
Leu Arg Leu Pro Gly
         295

ACCTCGTCCA CGATCGAACA GCAAAACTCC ACTCGAGTCC GTCAGAACAC TAGGGAACAT       1332

CCCTCCACGG CTAATACAGT GGATCGAACT AACCACCAGC TAGAAAATCT GGAGGCAGAA       1392
```

```
ACTGCTCCAT TGCCCTAACT GGGTCTCACA CCATCCAGAC CCTCGCTAAG CTTAGAGGCC    1452

GCCATCTACG TGGAATCAGG TTGCTGTCAG GGTGTGTGGG AGGCTCTGGT TTCCTGAGAA    1512

ACCATCTGAT CCTGCATTCA AAGTCATTCC TCTCTGGCTA CTTCACTCTG CACATGAGAG    1572

ATGCTCAGAC TGATCAAGAC CAGAAGAAAG AAGAGACTAC CGGACA                   1618
```

(2) INFORMATION FOR SEQ ID NO:4:

(i) SEQUENCE CHARACTERISTICS:
        (A) LENGTH: 298 amino acids
        (B) TYPE: amino acid
        (D) TOPOLOGY: linear (ii) MOLECULE TYPE: protein (xi) SEQUENCE DESCRIPTION: SEQ ID NO:4:

```
Met Arg Ser Glu Pro His Arg Ala Trp Arg Glu Arg Gln Pro Val Pro
  1               5                  10                  15

Ser Asp Arg Gln Pro Phe His Gly His Ser His Tyr His His Gly Pro
             20                  25                  30

Leu Leu Tyr Arg Val Cys Ser Gly Pro Leu Arg Lys Leu Pro Gly His
         35                  40                  45

Val Cys Asp Cys Lys Ile His Gln Asn Glu Asp Cys His Gln His Leu
     50                  55                  60

His Phe Gln Pro Cys Ser Gly Arg Arg Leu Ser Asp Gln Tyr Thr Ala
 65                  70                  75                  80

Leu Ser Glu Cys Gln Leu Pro Asp Gly Asn Met Ala Leu Arg Asn His
                 85                  90                  95

Pro Leu Gln Asp Arg Asp Leu Asn Arg Leu Leu Gln His Val His Gln
            100                 105                 110

His Ile His Pro Leu His His Glu Arg Gly Pro Leu His Cys Cys Leu
        115                 120                 125

Pro Pro Ser Gln Ser Pro Gly Phe Pro Tyr Pro Pro Lys Cys Gln Asn
    130                 135                 140

Arg Gln Arg Leu Gln Leu Asp Pro Leu Phe Cys His Arg Ser Ala Cys
145                 150                 155                 160

Asn Val His Gly Asn His Lys Ile Gln Ala Gly Val His Arg Leu His
                165                 170                 175

Pro His Val Leu Pro Pro Asn Leu Val Leu Gly Glu Pro Ala Gln Asn
            180                 185                 190

Leu Cys Leu Tyr Leu Arg Phe His His Ala Asp Pro His His His Cys
        195                 200                 205

Val Leu Arg Pro Asp Asp Leu Thr Thr Gln Glu Arg Ser His Ala Ile
    210                 215                 220

Gly Leu Gln Arg Lys Gly Gln Glu Ser Ala Gln Asp His Pro Asp Gly
225                 230                 235                 240

Ala Gly Gly Arg Gly Cys Ile Tyr Arg Leu Leu Asp Pro His Pro His
                245                 250                 255

Leu Arg His His Gln Ser Ala Asp His Asp Ser Arg Asn His Ile Ser
            260                 265                 270

Asp Arg Phe Leu Ala Leu Leu His Cys Phe Gly Leu His Glu Gln Leu
        275                 280                 285

Pro Glu Ser Ser Ser Leu Arg Leu Pro Gly
    290                 295
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (cDNA)

(xi) SEQUENCE DESCRIPTION: SEQ ID NO:5:

ATCTTCACCC TCACCATGAT G                                              21

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (cDNA)

(xi) SEQUENCE DESCRIPTION: SEQ ID NO:6:

CGGTCCTTCT CCTTGGAACC                                                20

(2) INFORMATION FOR SEQ ID NO:7:

(i) SEQUENCE CHARACTERISTICS:
        (A) LENGTH: 1610 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CGGATGAGCC TCTGTGAACT ACTAAGGTGG GAGGGGGCTA TACGCAGAGG AGAATGTCAG      60
ATGCTCAGCT CGGTCCCCTC CGCCTGACGC TCCTCTCTGT CTCAGCCAGG ACTGGTTTCT     120
GTAAGAAACA GCAGGAGCTG TGGCAGCGGC GAAAGGAAGC GGCTGAGGCG CTTGGAACCC     180
GAAAAGTCTC GGTGCTCCTG GCTACCTCGC ACAGCGTGCC CGCCCGGCCG TCAGTACCAT     240
GGACAGCAGC GCTGCCCCCA CGAACGCCAG CAATTGCACT GATGCCTTGG CGTACTCAAG     300
TTGCTCCCCA GCACCCAGCC CCGGTTCCTG GGTCAACTTG TCCCACTTAG ATGGCAACCT     360
GTCCGACCCA TGCGGTCCGA ACCGCACCGA CCTGGGCGGG AGAGACAGCC TGTGCCCTCC     420
GACCGGCAGT CCCTCCATGA TCACGGCCAT CACGATCATG GCCCTCTACT CCATCGTGTG     480
CGTGGTGGGG CTCTTCGGAA ACTTCCTGGT CATGTATGTG ATTGTCAGAT ACACCAAGAT     540
GAAGACTGCC ACCAACATCT ACATTTTCAA CCTTGCTCTG GCAGATGCCT TAGCCACCAG     600
TACCCTGCCC TTCCAGAGTG TGAATTACCT AATGGGAACA TGGCCATTTG GAACCATCCT     660
TTGCAAGATA GTGATCTCCA TAGATTACTA TAACATGTTC ACCAGCATAT TCACCCTCTG     720
CACCATGAGT GTTGATCGAT ACATTGCAGT CTGCCACCCT GTCAAGGCCT TAGATTTCCG     780
TACTCCCCGA AATGCCAAAA TTATCAATGT CTGCAACTGG ATCCTCTCTT CAGCCATTGG     840
TCTTCCTGTA ATGTTCATGG CTACAACAAA ATACAGGCAA GGTTCCATAG ATTGTACACT     900
AACATTCTCT CATCCAACCT GGTACTGGGA AAACCTGCTG AAGATCTGTG TTTTCATCTT     960
CGCCTTCATT ATGCCAGTGC TCATCATTAC CGTGTGCTAT GGACTGATGA TCTTGCGCCT    1020
CAAGAGTGTC CGCATGCTCT CTGGCTCCAA AGAAAAGGAC AGGAATCTTC GAAGGATCAC    1080
CAGGATGGTG CTGGTGGTGG TGGCTGTGTT CATCGTCTGC TGGACTCCCA TTCACATTTA    1140

```
CGTCATCATT AAAGCCTTGG TTACAATCCC AGAAACTACG TTCCAGACTG TTTCTTGGCA      1200

CTTCTGCATT GCTCTAGGTT ACACAAACAG CTGCCTCAAC CCAGTCCTTT ATGCATTTCT      1260

GGATGAAAAC TTCAAACGAT GCTTCAGAGA GTTCTGTATC CCAACCTCTT CCAACATTGA      1320

GCAACAAAAC TCCACTCGAA TTCGTCAGAA CACTAGAGAC CACCCCTCCA CGGCCAATAC      1380

AGTGGATAGA ACTAATCATC AGCTAGAAAA TCTGGAAGCA GAAACTGCTC CGTTGCCCTA      1440

ACAGGGTCTC ATGCCATTCC GACCTTCACC AAGCTTAGAA GCCACCATGT ATGTGGAAGC      1500

AGGTTGCTTC AAGAATGTGT AGGAGGCTCT AATTCTCTAG GAAAGTGCCT GCTTTTAGGT      1560

CATCCAACCT CTTTCCTCTC TGGCCACTCT GCTCTGCACA TTAGAGGCCG                 1610
```

(2) INFORMATION FOR SEQ ID NO:8:

(i) SEQUENCE CHARACTERISTICS:
        (A) LENGTH: 400 amino acids
        (B) TYPE: amino acid
        (D) TOPOLOGY: linear (ii) MOLECULE TYPE: protein (xi) SEQUENCE DESCRIPTION: SEQ ID NO:8:

```
Met Asp Ser Ser Ala Ala Pro Thr Asn Ala Ser Asn Cys Thr Asp Ala
1               5                   10                  15

Leu Ala Tyr Ser Ser Cys Ser Pro Ala Pro Ser Pro Gly Ser Trp Val
            20                  25                  30

Asn Leu Ser His Leu Asp Gly Asn Leu Ser Asp Pro Cys Gly Pro Asn
        35                  40                  45

Arg Thr Asp Leu Gly Gly Arg Asp Ser Leu Cys Pro Pro Thr Gly Ser
50                  55                  60

Pro Ser Met Ile Thr Ala Ile Thr Ile Met Ala Leu Tyr Ser Ile Val
65                  70                  75                  80

Cys Val Val Gly Leu Phe Gly Asn Phe Leu Val Met Tyr Val Ile Val
                85                  90                  95

Arg Tyr Thr Lys Met Lys Thr Ala Thr Asn Ile Tyr Ile Phe Asn Leu
            100                 105                 110

Ala Leu Ala Asp Ala Leu Ala Thr Ser Thr Leu Pro Phe Gln Ser Val
        115                 120                 125

Asn Tyr Leu Met Gly Thr Trp Pro Phe Gly Thr Ile Leu Cys Lys Ile
    130                 135                 140

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
                165                 170                 175

Ala Leu Asp Phe Arg Thr Pro Arg Asn Ala Lys Ile Ile Asn Val Cys
            180                 185                 190

Asn Trp Ile Leu Ser Ser Ala Ile Gly Leu Pro Val Met Phe Met Ala
        195                 200                 205

Thr Thr Lys Tyr Arg Gln Gly Ser Ile Asp Cys Thr Leu Thr Phe Ser
    210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270
```

```
Lys Asp Arg Asn Leu Arg Arg Ile Thr Arg Met Val Leu Val Val
        275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
                340                 345                 350

Cys Ile Pro Thr Ser Ser Asn Ile Glu Gln Gln Asn Ser Thr Arg Ile
            355                 360                 365

Arg Gln Asn Thr Arg Asp His Pro Ser Thr Ala Asn Thr Val Asp Arg
    370                 375                 380

Thr Asn His Gln Leu Glu Asn Leu Glu Ala Glu Thr Ala Pro Leu Pro
385                 390                 395                 400

(2) INFORMATION FOR SEQ ID NO:9:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:9:

Asn His Gln Leu Glu Asn Leu Glu Ala Glu Thr Ala Pro Leu Pro
1               5                   10                  15

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TGAAGACTGC CACCAACA                                              18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GATGACGTAG ATGTGGAT                                              18

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:12:

CTCGGATCCG TATTATGTCT G                                           21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ATAGTCGACT AAAACTAAAT C                                           21

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

ACYGCMACCA ACATCTACAT                                             20

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GCTRGTRAAC ATGTTGTAGT A                                           21

(2) INFORMATION FOR SEQ ID NO:16:

(i) SEQUENCE CHARACTERISTICS:
        (A) LENGTH: 1567 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 173..1273

(xi) SEQUENCE DESCRIPTION: SEQ ID NO:16:

CCATTCCCAG CCGCAGCAGA CCCCAATCTA GAGTGAGAGT CATTGCTCAG TCCACTGTGC   60

TCCTGCCTGC CCGCCTTTCT GCTAAGCATT GGGGTCTATT TTGGCCCAGC TTCTGAAGAG  120

GCTGTGTGTG CCGTTGGAGG AACTGTACTG AGTGGCTTTG CAGGGTGACA GC ATG      175
                                                                                                        Met
                                                                                                        1

GAG TCC CTC TTT CCT GCT CCA TAC TGG GAG GTC TTG TAT GGC AGC CAC   223
Glu Ser Leu Phe Pro Ala Pro Tyr Trp Glu Val Leu Tyr Gly Ser His
        5                   10                 15

```
TTT CAA GGG AAC CTG TCC CTC CTA AAT GAG ACC GTA CCC CAC CAC CTG      271
Phe Gln Gly Asn Leu Ser Leu Leu Asn Glu Thr Val Pro His His Leu
         20                  25                  30

CTC CTC AAT GCT AGT CAC AGC GCC TTC CTG CCC CTT GGA CTC AAG GTC      319
Leu Leu Asn Ala Ser His Ser Ala Phe Leu Pro Leu Gly Leu Lys Val
     35                  40                  45

ACC ATC GTG GGG CTC TAC TTG GCT GTG TGC ATC GGG GGG CTC CTG GGG      367
Thr Ile Val Gly Leu Tyr Leu Ala Val Cys Ile Gly Gly Leu Leu Gly
 50                  55                  60                  65

AAC TGC CTC GTC ATG TAT GTC ATC CTC AGG CAC ACC AAG ATG AAG ACA      415
Asn Cys Leu Val Met Tyr Val Ile Leu Arg His Thr Lys Met Lys Thr
                 70                  75                  80

GCT ACC AAC ATT TAC ATA TTT AAT CTG GCA CTG GCT GAT ACC CTG GTC      463
Ala Thr Asn Ile Tyr Ile Phe Asn Leu Ala Leu Ala Asp Thr Leu Val
             85                  90                  95

TTG CTA ACA CTG CCC TTC CAG GGC ACA GAC ATC CTA CTG GGC TTC TGG      511
Leu Leu Thr Leu Pro Phe Gln Gly Thr Asp Ile Leu Leu Gly Phe Trp
         100                 105                 110

CCA TTT GGG AAT GCA CTC TGC AAG ACT GTC ATT GCT ATC GAC TAC TAC      559
Pro Phe Gly Asn Ala Leu Cys Lys Thr Val Ile Ala Ile Asp Tyr Tyr
     115                 120                 125

AAC ATG TTT ACC AGC ACT TTT ACT CTG ACC GCC ATG AGC GTA GAC CGC      607
Asn Met Phe Thr Ser Thr Phe Thr Leu Thr Ala Met Ser Val Asp Arg
130                 135                 140                 145

TAT GTG GCT ATC TGC CAC CCT ATC CGT GCC CTT GAT GTT CGG ACA TCC      655
Tyr Val Ala Ile Cys His Pro Ile Arg Ala Leu Asp Val Arg Thr Ser
                 150                 155                 160

AGC AAA GCC CAG GCT GTT AAT GTG GCC ATA TGG GCC CTG GCT TCA GTG      703
Ser Lys Ala Gln Ala Val Asn Val Ala Ile Trp Ala Leu Ala Ser Val
             165                 170                 175

GTT GGT GTT CCT GTT GCC ATC ATG GGT TCA GCA CAA GTG GAA GAT GAA      751
Val Gly Val Pro Val Ala Ile Met Gly Ser Ala Gln Val Glu Asp Glu
         180                 185                 190

GAG ATC GAG TGC CTG GTG GAG ATC CCT GCC CCT CAG GAC TAT TGG GGC      799
Glu Ile Glu Cys Leu Val Glu Ile Pro Ala Pro Gln Asp Tyr Trp Gly
     195                 200                 205

CCT GTA TTC GCC ATC TGC ATC TTC CTT TTT TCC TTC ATC ATC CCT GTG      847
Pro Val Phe Ala Ile Cys Ile Phe Leu Phe Ser Phe Ile Ile Pro Val
210                 215                 220                 225

CTG ATC ATC TCT GTC TGC TAC AGC CTC ATG ATT CGA CGA CTT CGT GGT      895
Leu Ile Ile Ser Val Cys Tyr Ser Leu Met Ile Arg Arg Leu Arg Gly
                 230                 235                 240

GTC CGT CTG CTT TCA GGC TCC CGG GAG AAG GAC CGA AAC CTG CGG CGT      943
Val Arg Leu Leu Ser Gly Ser Arg Glu Lys Asp Arg Asn Leu Arg Arg
             245                 250                 255

ATC ACT CGA CTG GTG CTG GTA GTG GTG GCT GTG TTT GTG GGC TGC TGG      991
Ile Thr Arg Leu Val Leu Val Val Val Ala Val Phe Val Gly Cys Trp
         260                 265                 270

ACG CCT GTG CAG GTG TTT GTC CTG GTT CAA GGA CTG GGT GTT CAG CCA     1039
Thr Pro Val Gln Val Phe Val Leu Val Gln Gly Leu Gly Val Gln Pro
     275                 280                 285

GGT AGT GAG ACT GCA GTT GCC ATC CTG CGC TTC TGC ACA GCC CTG GGC     1087
Gly Ser Glu Thr Ala Val Ala Ile Leu Arg Phe Cys Thr Ala Leu Gly
290                 295                 300                 305

TAT GTC AAC AGT TGT CTC AAT CCC ATT CTC TAT GCT TTC CTG GAT GAG     1135
Tyr Val Asn Ser Cys Leu Asn Pro Ile Leu Tyr Ala Phe Leu Asp Glu
                 310                 315                 320

AAC TTC AAG GCC TGC TTT AGA AAG TTC TGC TGT GCT TCA TCC CTG CAC     1183
Asn Phe Lys Ala Cys Phe Arg Lys Phe Cys Cys Ala Ser Ser Leu His
             325                 330                 335
```

```
CGG GAG ATG CAG GTT TCT GAT CGT GTG CGG AGC ATT GCC AAG GAT GTT       1231
Arg Glu Met Gln Val Ser Asp Arg Val Arg Ser Ile Ala Lys Asp Val
            340                 345                 350

GGC CTT GGT TGC AAG ACT TCT GAG ACA GTA CCA CGG CCA GCA               1273
Gly Leu Gly Cys Lys Thr Ser Glu Thr Val Pro Arg Pro Ala
        355                 360                 365

TGACTAGGCG TGGACCTGCC CATGGTGCCT GTCAGCCCAC AGAGCCCATC TACACCCAAC     1333

ACGGAGCTCA CACAGGTCAC TGCTCTCTAG GTTGACCCTG AACCTTGAGC ATCTGGAGCC     1393

TTGAATGGCT TTTCTTTTGG ATCAGGATGC TCAGTCCTAG AGGAAGACCT TTTAGCACCA     1453

TGGGACAGGT CAAAGCATCA AGGTGGTCTC CATGGCCTCT GTCAGATTAA GTTCCCTCCC    1513

TGGTATAGGA CCAGAGAGGA CCAAAGGAAC TGAATAGAAA CATCCACAAC ACAG          1567

(2) INFORMATION FOR SEQ ID NO:17:

(i) SEQUENCE CHARACTERISTICS:
        (A) LENGTH: 367 amino acids
        (B) TYPE: amino acid
        (D) TOPOLOGY: linear (ii) MOLECULE TYPE: protein (xi) SEQUENCE DESCRIPTION: SEQ ID NO:17:

Met Glu Ser Leu Phe Pro Ala Pro Tyr Trp Glu Val Leu Tyr Gly Ser
 1               5                  10                  15

His Phe Gln Gly Asn Leu Ser Leu Leu Asn Glu Thr Val Pro His His
            20                  25                  30

Leu Leu Leu Asn Ala Ser His Ser Ala Phe Leu Pro Leu Gly Leu Lys
        35                  40                  45

Val Thr Ile Val Gly Leu Tyr Leu Ala Val Cys Ile Gly Gly Leu Leu
    50                  55                  60

Gly Asn Cys Leu Val Met Tyr Val Ile Leu Arg His Thr Lys Met Lys
65                  70                  75                  80

Thr Ala Thr Asn Ile Tyr Ile Phe Asn Leu Ala Leu Ala Asp Thr Leu
                85                  90                  95

Val Leu Leu Thr Leu Pro Phe Gln Gly Thr Asp Ile Leu Leu Gly Phe
            100                 105                 110

Trp Pro Phe Gly Asn Ala Leu Cys Lys Thr Val Ile Ala Ile Asp Tyr
        115                 120                 125

Tyr Asn Met Phe Thr Ser Thr Phe Thr Leu Thr Ala Met Ser Val Asp
    130                 135                 140

Arg Tyr Val Ala Ile Cys His Pro Ile Arg Ala Leu Asp Val Arg Thr
145                 150                 155                 160

Ser Ser Lys Ala Gln Ala Val Asn Val Ala Ile Trp Ala Leu Ala Ser
                165                 170                 175

Val Val Gly Val Pro Val Ala Ile Met Gly Ser Ala Gln Val Glu Asp
            180                 185                 190

Glu Glu Ile Glu Cys Leu Val Glu Ile Pro Ala Pro Gln Asp Tyr Trp
        195                 200                 205

Gly Pro Val Phe Ala Ile Cys Ile Phe Leu Phe Ser Phe Ile Ile Pro
    210                 215                 220

Val Leu Ile Ile Ser Val Cys Tyr Ser Leu Met Ile Arg Arg Leu Arg
225                 230                 235                 240

Gly Val Arg Leu Leu Ser Gly Ser Arg Glu Lys Asp Arg Asn Leu Arg
                245                 250                 255
```

-continued

```
Arg Ile Thr Arg Leu Val Leu Val Val Ala Val Phe Val Gly Cys
            260             265             270

Trp Thr Pro Val Gln Val Phe Val Leu Val Gln Gly Leu Gly Val Gln
            275             280             285

Pro Gly Ser Glu Thr Ala Val Ala Ile Leu Arg Phe Cys Thr Ala Leu
    290             295             300

Gly Tyr Val Asn Ser Cys Leu Asn Pro Ile Leu Tyr Ala Phe Leu Asp
305             310             315             320

Glu Asn Phe Lys Ala Cys Phe Arg Lys Phe Cys Cys Ala Ser Ser Leu
            325             330             335

His Arg Glu Met Gln Val Ser Asp Arg Val Arg Ser Ile Ala Lys Asp
            340             345             350

Val Gly Leu Gly Cys Lys Thr Ser Glu Thr Val Pro Arg Pro Ala
            355             360             365
```